US010548624B2

(12) United States Patent
Mirza et al.

(10) Patent No.: US 10,548,624 B2
(45) Date of Patent: Feb. 4, 2020

(54) COMPACT ENDOSCOPIC SURGICAL BLADE ASSEMBLY AND METHOD OF USE THEREOF

(71) Applicant: A.M. SURGICAL, INC., Smithtown, NY (US)

(72) Inventors: Romi Mirza, Smithtown, NY (US); Ather Mirza, Smithtown, NY (US)

(73) Assignee: A.M. SURGICAL, INC., Smithtown, NY (US)

( * ) Notice: Subject to any disclaimer, the term of this patent is extended or adjusted under 35 U.S.C. 154(b) by 10 days.

(21) Appl. No.: 15/661,968

(22) Filed: Jul. 27, 2017

(65) Prior Publication Data

US 2017/0333066 A1 Nov. 23, 2017

Related U.S. Application Data

(63) Continuation of application No. 15/239,557, filed on Aug. 17, 2016, now Pat. No. 9,808,274, which is a
(Continued)

(51) Int. Cl.
*A61B 17/32* (2006.01)
*A61B 1/00* (2006.01)
(Continued)

(52) U.S. Cl.
CPC .... *A61B 17/32002* (2013.01); *A61B 1/00087* (2013.01); *A61B 1/00128* (2013.01);
(Continued)

(58) Field of Classification Search
CPC .............. A61B 1/00128; A61B 1/3132; A61B 2017/320064; A61B 17/320016;
(Continued)

(56) References Cited

U.S. PATENT DOCUMENTS 5,273,024 A 12/1993 Menon et al.
5,322,055 A 6/1994 Davison et al.
(Continued)

FOREIGN PATENT DOCUMENTS

WO 2012/096746 A1 7/2012

OTHER PUBLICATIONS

File history of U.S. Appl. No. 13/790,016, filed Mar. 8, 2013.
(Continued)

*Primary Examiner* — Erich G Herbermann
(74) *Attorney, Agent, or Firm* — Ping Wang; Morris, Manning & Martin, LLP

(57) ABSTRACT

An endoscopic surgical device having a slotted clear cannula, a blade and a housing, wherein the cannula is attached to the housing, and wherein the blade is enclosed in the housing and is slidable into the cannula is disclosed. The blade is enclosed within the housing and cannula, and has a horizontally-oriented pushing component and a vertically-oriented cutting component that protrudes through the slot of the cannula. The device further has a device for locking a viewing device in place relative to other components of the device. A method for a performing an operative procedure on a target tissue in a subject using the endoscopic surgical device is also described.

12 Claims, 46 Drawing Sheets

Related U.S. Application Data continuation of application No. 14/736,904, filed on Jun. 11, 2015, now Pat. No. 9,445,830, which is a continuation of application No. 14/013,746, filed on Aug. 29, 2013, now Pat. No. 9,066,746, which is a continuation-in-part of application No. 13/790,016, filed on Mar. 8, 2013, now Pat. No. 8,911,470, which is a continuation-in-part of application No. 13/602,968, filed on Sep. 4, 2012.

(51) Int. Cl.
*A61B 1/313* (2006.01)
*A61B 17/3205* (2006.01)
*A61B 1/018* (2006.01)
*A61B 17/00* (2006.01)

(52) U.S. Cl.
CPC .......... *A61B 1/00135* (2013.01); *A61B 1/018* (2013.01); *A61B 1/3132* (2013.01); *A61B 17/3205* (2013.01); *A61B 17/320016* (2013.01); *A61B 17/320036* (2013.01); *A61B 2017/00353* (2013.01); *A61B 2017/320008* (2013.01); *A61B 2017/320064* (2013.01)

(58) Field of Classification Search
CPC ........ A61B 17/320036; A61B 17/3205; A61B 17/320064; A61B 17/32002; A61B 1/00087; A61B 1/00135; A61B 1/018; A61B 17/00353; A61B 17/32008; A61B 2017/00353; A61B 2017/320008
USPC ......... 606/170–172, 1, 79–85, 167; 600/564, 600/106, 104, 570; 7/158; 81/439, 440; 30/162, 163, 152
See application file for complete search history.

(56) References Cited

U.S. PATENT DOCUMENTS

| | | | |
|---|---|---|---|
| 5,447,513 A | 9/1995 | Davison et al. | |
| 5,569,283 A | 10/1996 | Green et al. | |
| 5,595,410 A | 1/1997 | Wilson et al. | |
| 5,755,713 A * | 5/1998 | Bilof | A61B 17/00234 600/104 |
| 6,589,231 B1 | 7/2003 | Gobron et al. | |
| 6,869,112 B2 * | 3/2005 | Guidetti | F16B 2/246 280/823 |
| 2004/0098005 A1 | 5/2004 | Mirza et al. | |
| 2004/0230155 A1 | 11/2004 | Blanco et al. | |
| 2006/0264994 A1* | 11/2006 | Schomer | A61B 10/0275 606/170 |
| 2007/0288043 A1 | 12/2007 | Rehnke | |
| 2008/0045989 A1 | 2/2008 | Welborn | |
| 2008/0065124 A1 | 3/2008 | Olson | |
| 2009/0043270 A1* | 2/2009 | Noyce | A61F 17/00 604/327 |
| 2009/0306541 A1* | 12/2009 | Kano | A61B 10/0266 600/564 |
| 2010/0228083 A1 | 9/2010 | Mirza et al. | |
| 2010/0228085 A1 | 9/2010 | Mirza et al. | |
| 2011/0046652 A1* | 2/2011 | Rehnke | A61B 1/313 606/170 |
| 2011/0130779 A1* | 6/2011 | Mirza | A61B 1/018 606/170 |

OTHER PUBLICATIONS

File history of U.S. Appl. No. 13/602,968, filed Sep. 4, 2012.
File history of U.S. Appl. No. 14/013,746, filed Aug. 29, 2013.
File history of U.S. Appl. No. 14/736,904, filed Jun. 11, 2015.
File history of U.S. Appl. No. 15/239,557, filed Aug. 17, 2016.

* cited by examiner

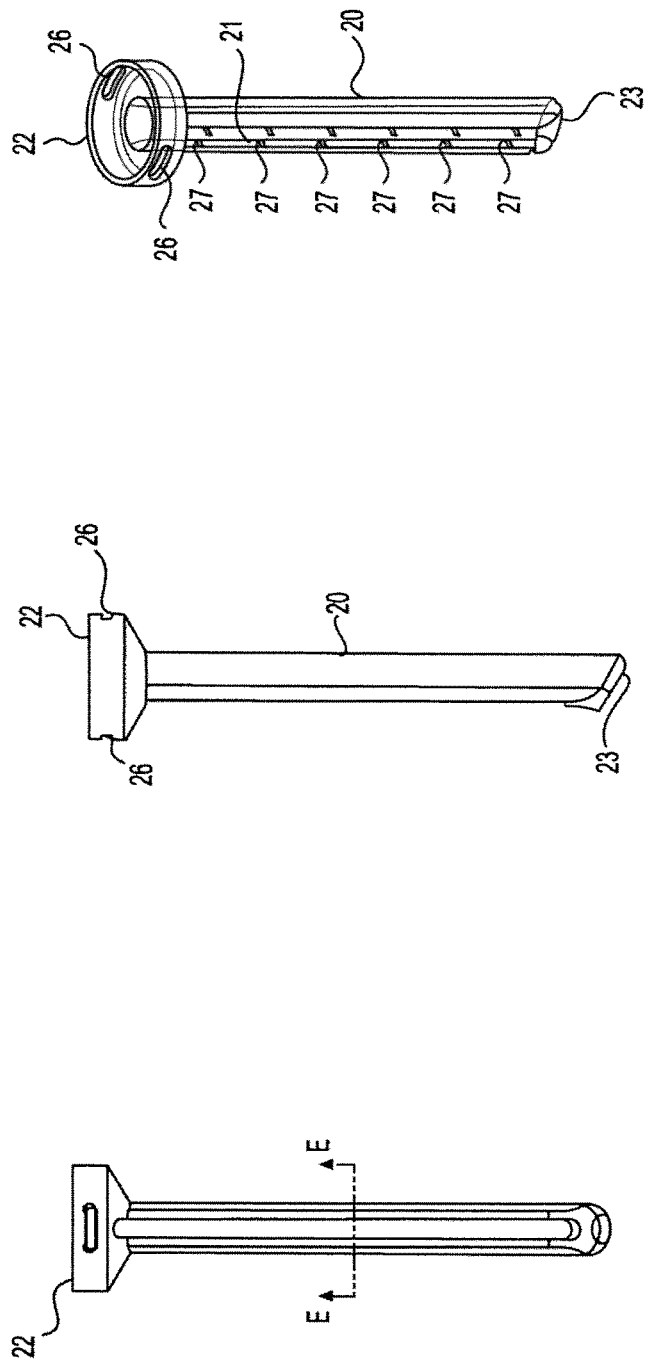
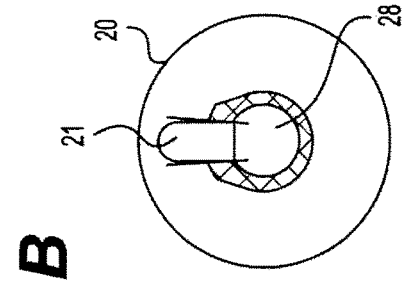
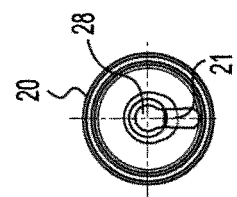

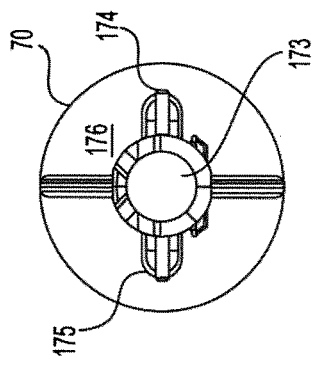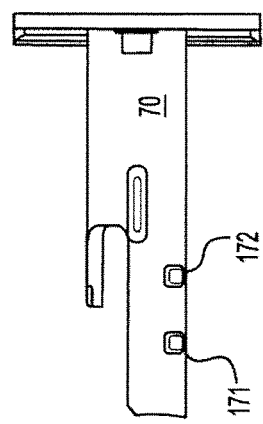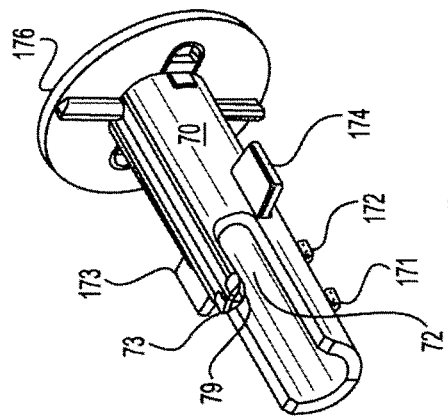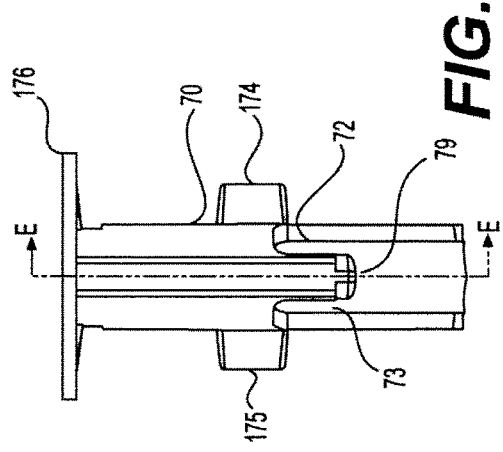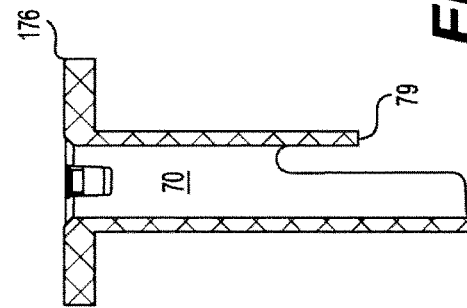

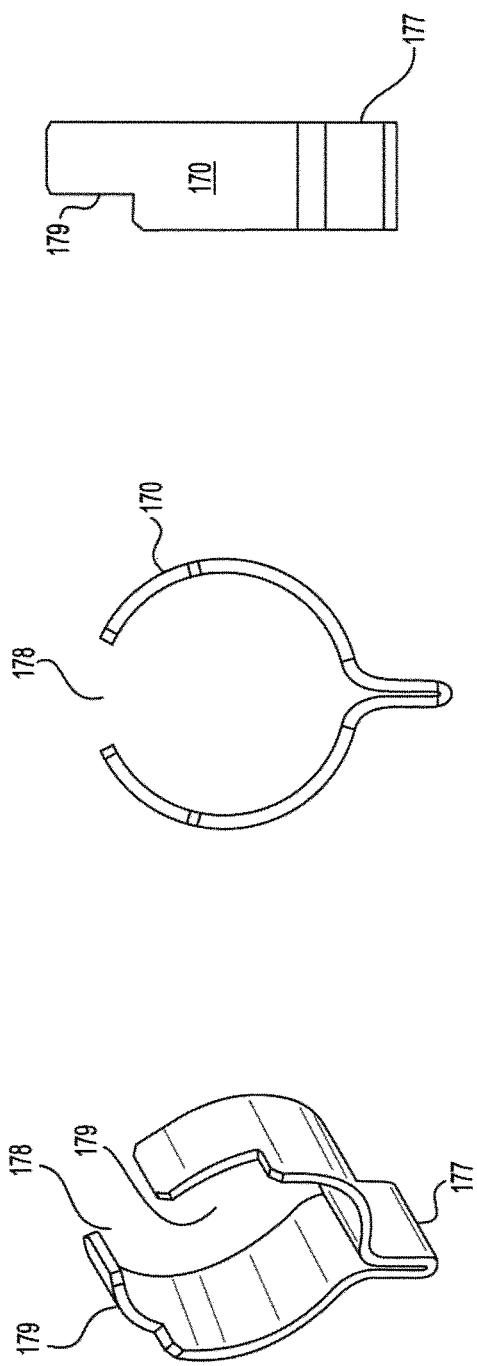

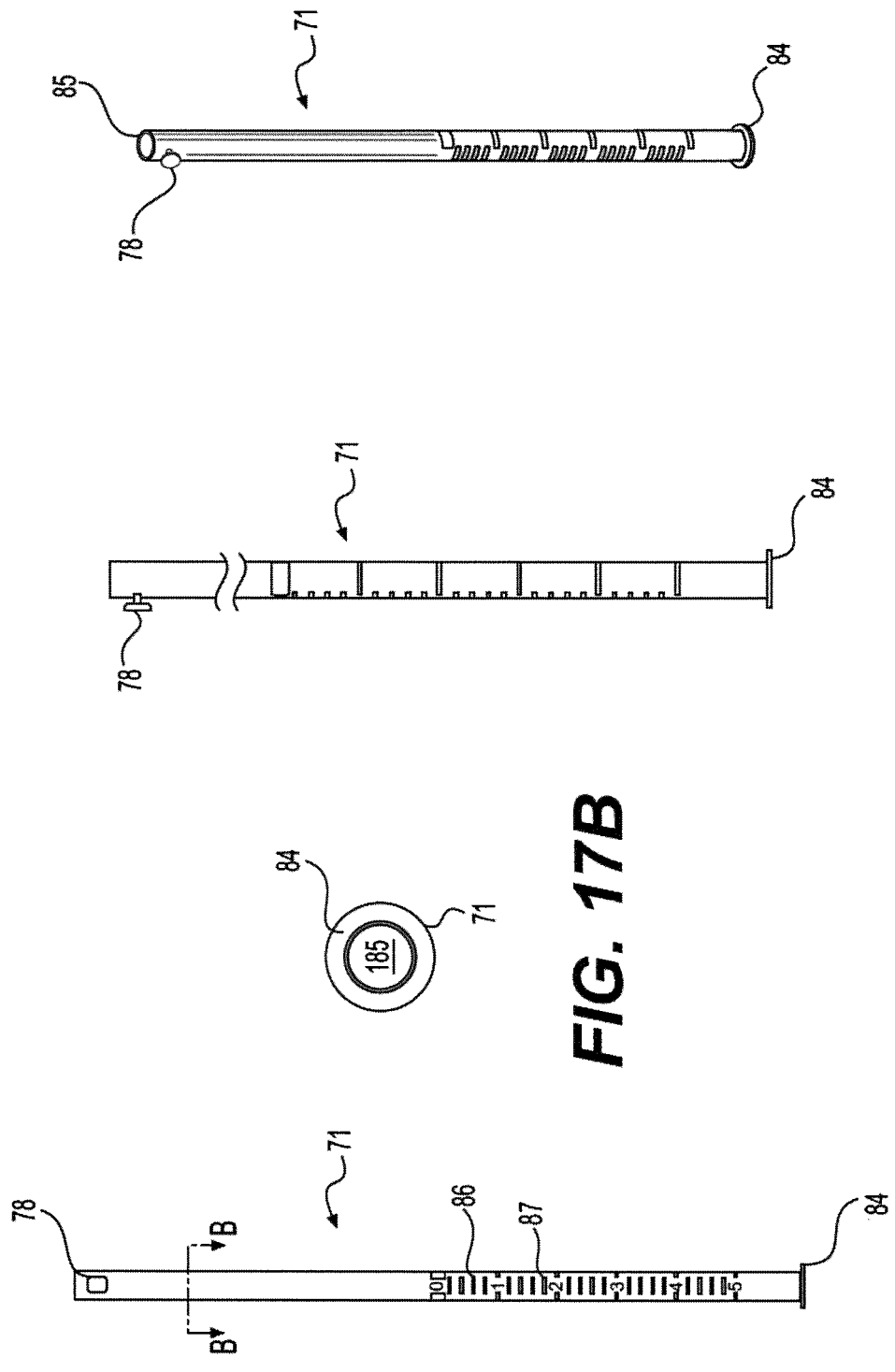

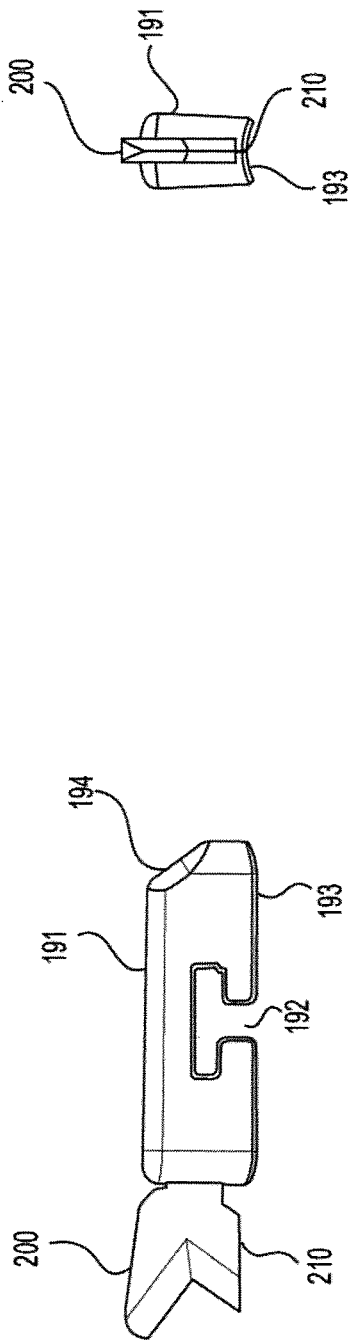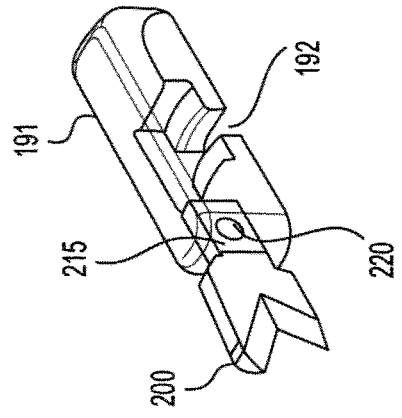
FIG. 18B
FIG. 18C
FIG. 18A

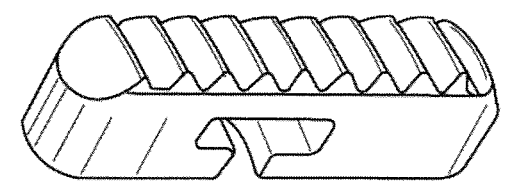
FIG. 23E
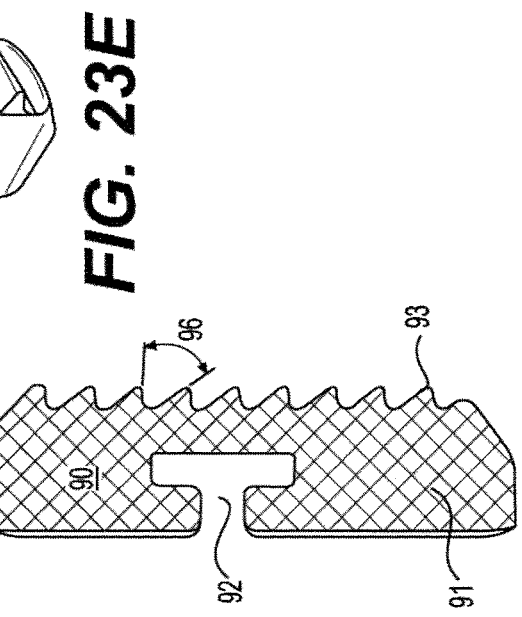
FIG. 23D
FIG. 23C
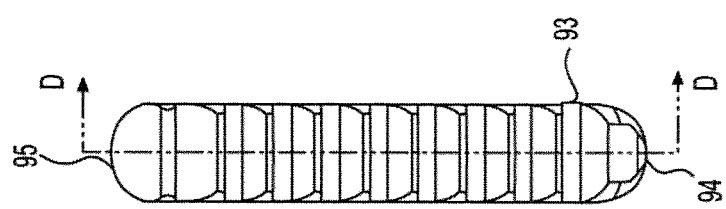
FIG. 23B
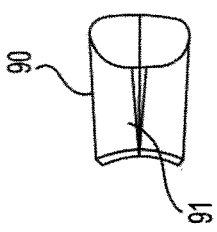
FIG. 23A
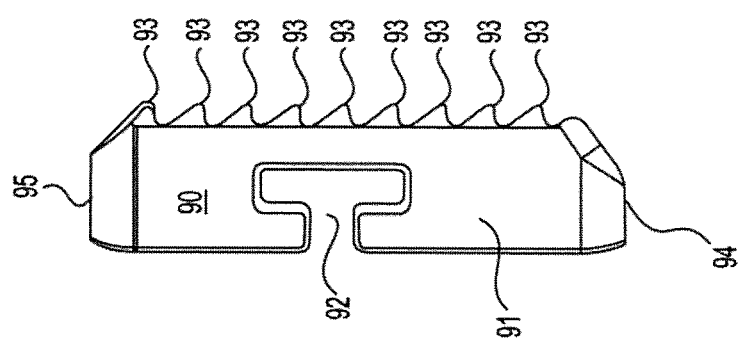

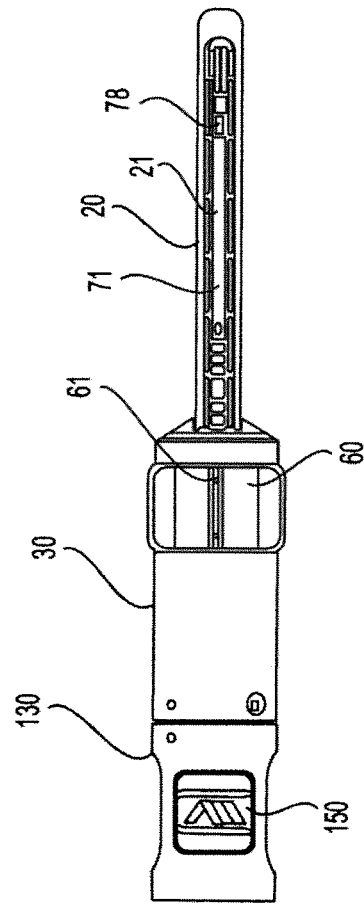
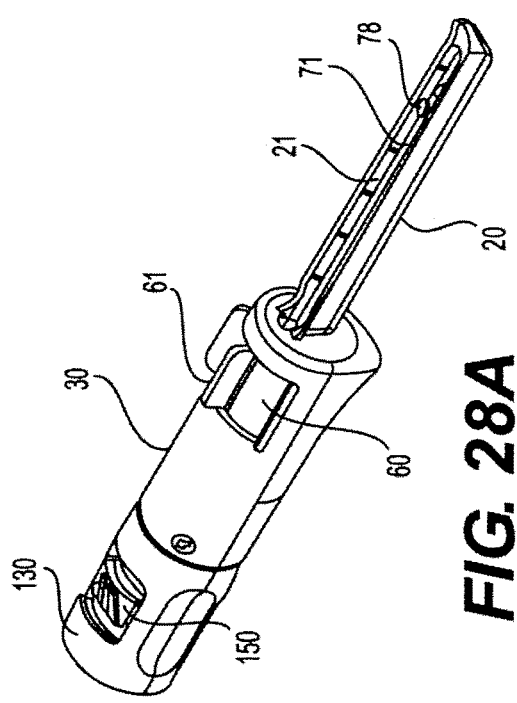
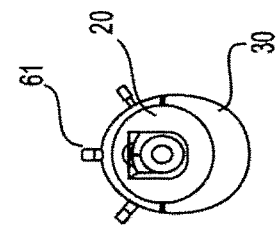
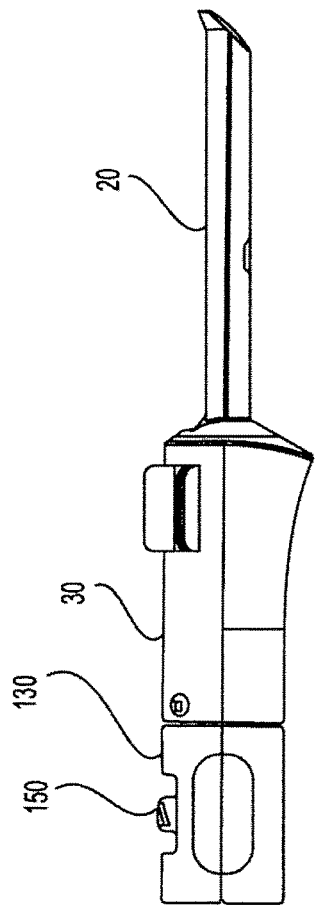
FIG. 28A
FIG. 28B
FIG. 28C
FIG. 28D

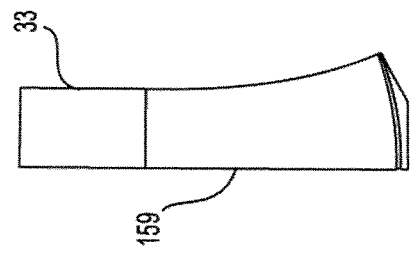
FIG. 32D
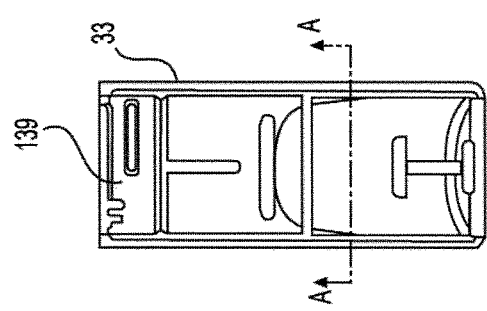
FIG. 32C
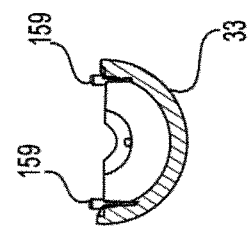
FIG. 32F
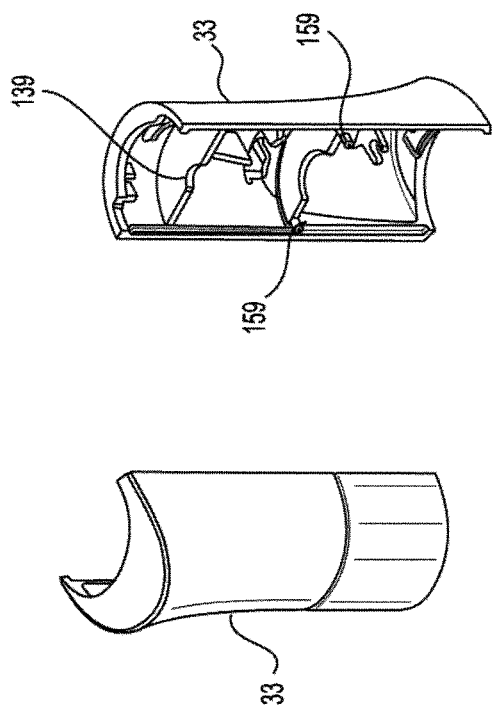
FIG. 32B
FIG. 32E
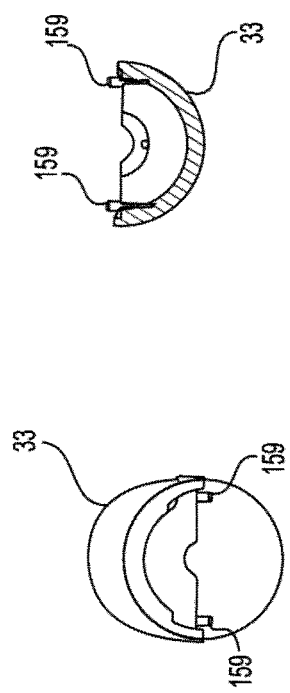
FIG. 32A

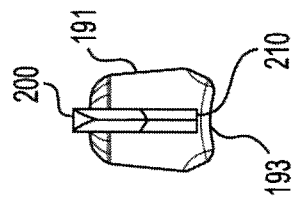
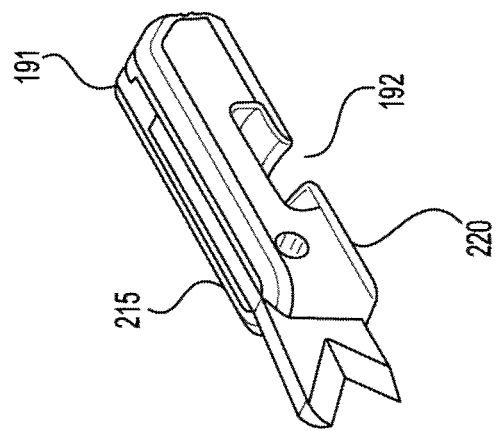
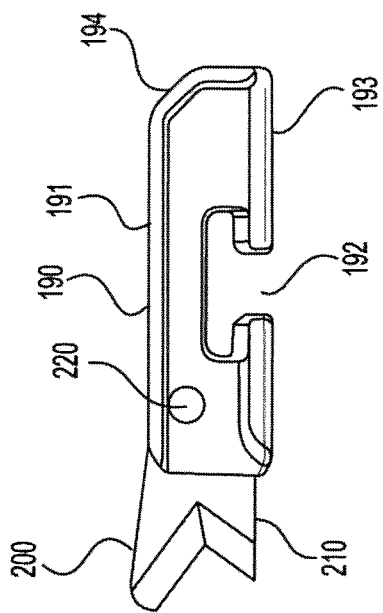
FIG. 33B
FIG. 33C
FIG. 33A

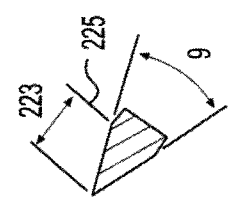
*FIG. 34B*
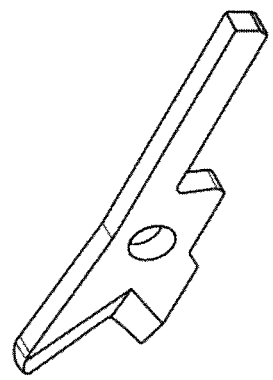
*FIG. 34E*
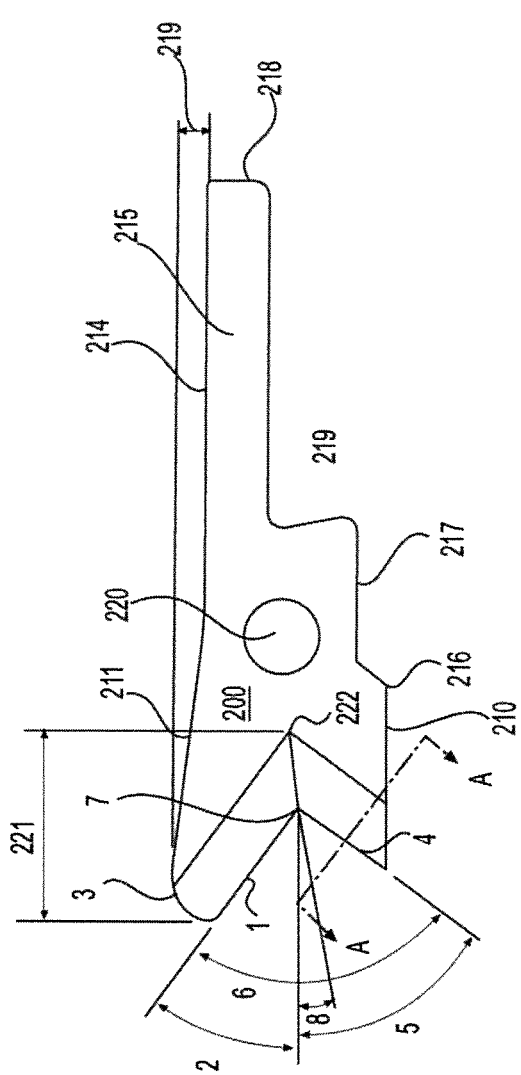
*FIG. 34A*
*FIG. 34D*
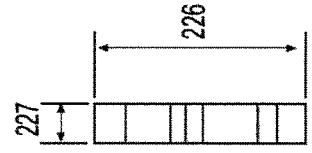
*FIG. 34C*

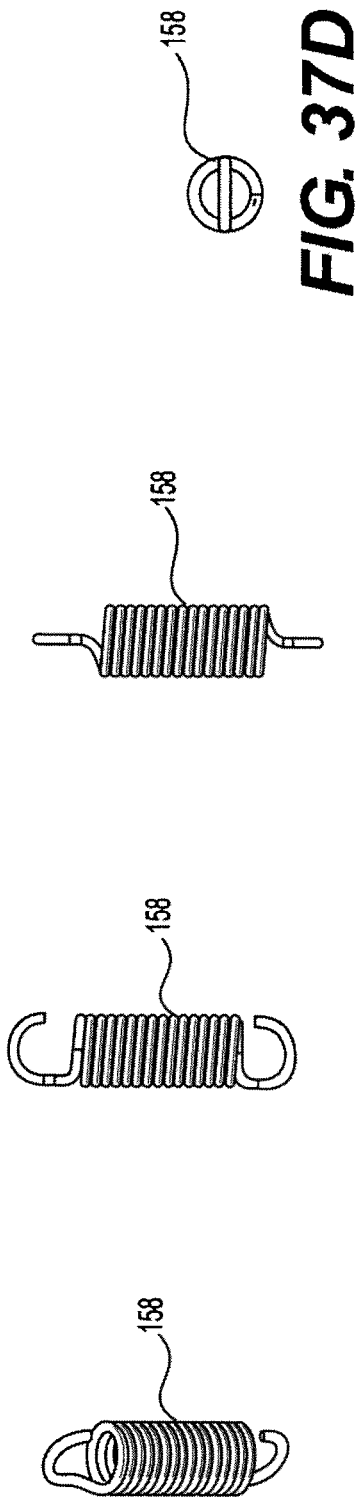

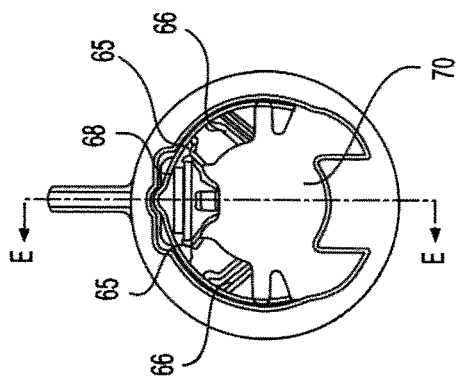
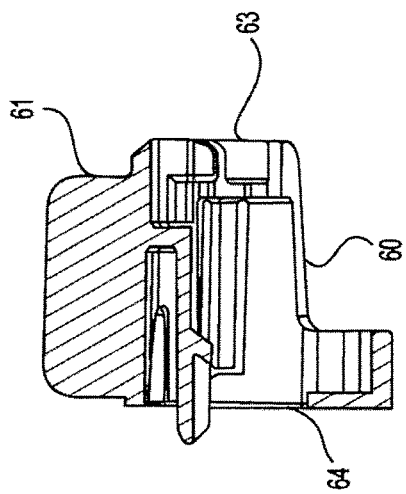
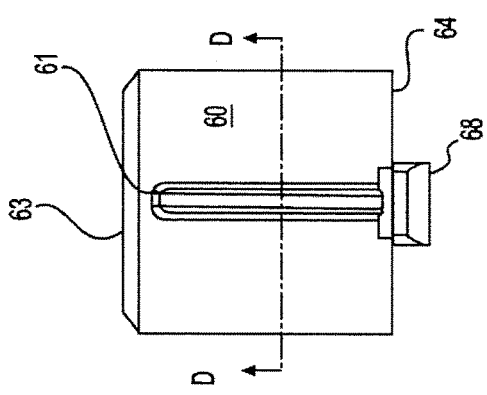
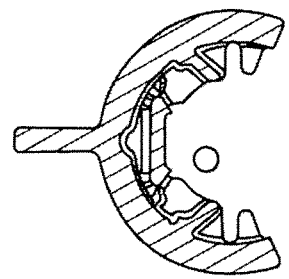
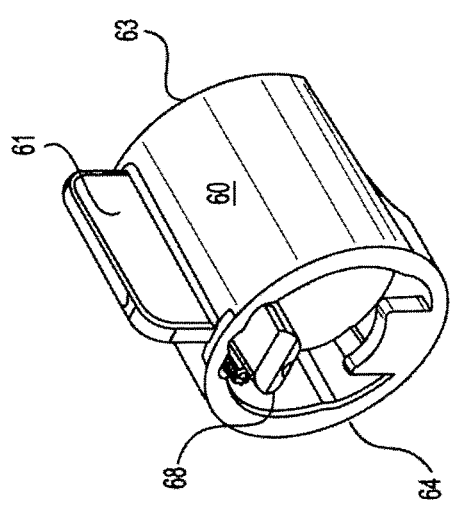
FIG. 41A
FIG. 41B
FIG. 41C
FIG. 41D
FIG. 41E

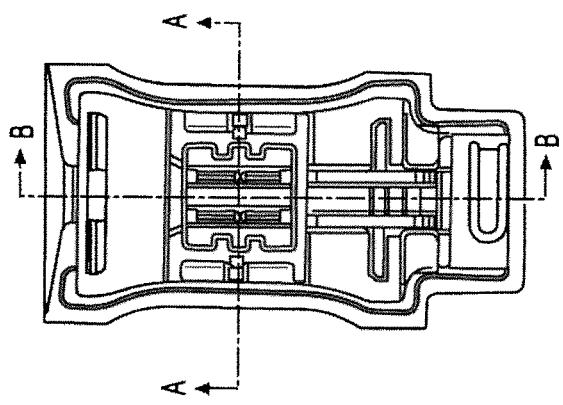
FIG. 43C
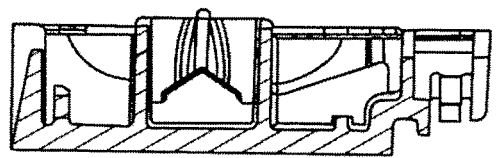
FIG. 43F
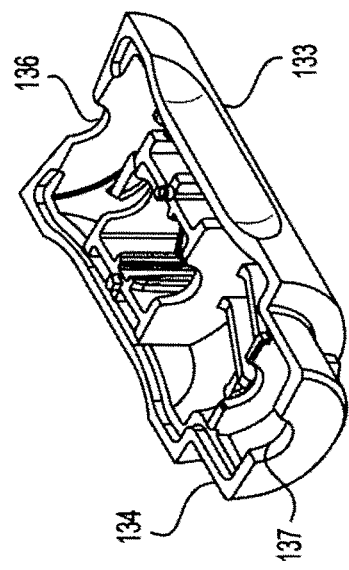
FIG. 43B
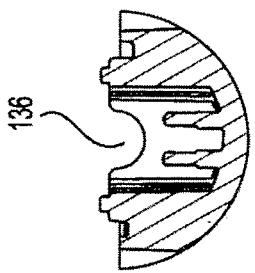
FIG. 43E
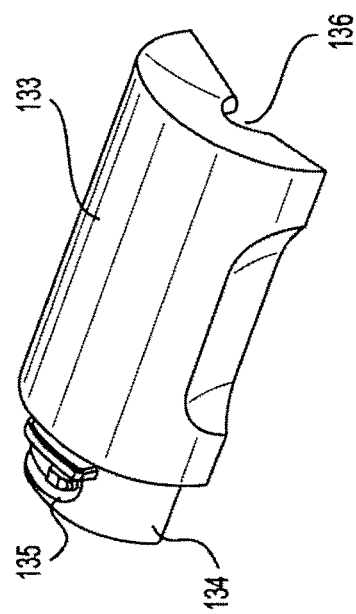
FIG. 43A
FIG. 43D

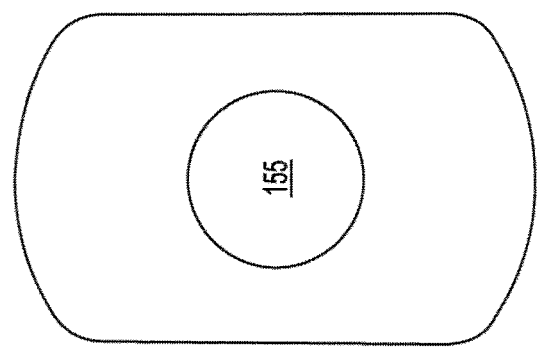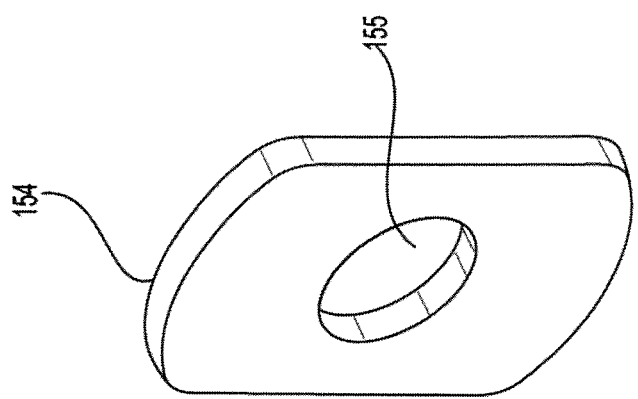
FIG. 46D
FIG. 46C
FIG. 46B
FIG. 46A

COMPACT ENDOSCOPIC SURGICAL BLADE ASSEMBLY AND METHOD OF USE THEREOF

This application is a Continuation of application Ser. No. 15/239,557, filed on Aug. 17, 2016, which is a Continuation of application Ser. No. 14/736,904, filed on Jun. 11, 2015, now a U.S. Pat. No. 9,445,830, which is a Continuation of application Ser. No. 14/013,746, filed on Aug. 29, 2013, now U.S. Pat. No. 9,066,746, which is a Continuation-In-Part of application Ser. No. 13/790,016, filed Mar. 8, 2013, now U.S. Pat. No. 8,911,470, which is a Continuation-In-Part of application Ser. No. 13/602,968, filed on Sep. 4, 2012. The entirety of the aforementioned applications is incorporated herein by reference.

FIELD

This application generally relates to medical devices. In particular, the application relates to devices and methods for endoscopic surgery, e.g., for endoscopic tunnel or pulley release surgery.

BACKGROUND

Endoscopic surgery is a minimally invasive surgical procedure that is performed through small incisions or natural body openings. An endoscopic procedure typically involves use of specialized devices and remote-control manipulation of instruments with indirect observation of the surgical field through an endoscope or similar device. Comparing to open surgery, endoscopic surgery may result in shorter hospital stays, or allow outpatient treatment.

Trigger finger is characterized by catching, snapping or locking of the involved finger flexor tendon, associated with dysfunction and pain. Localized inflammation or nodular swelling of said flexor tendon causes a disparity in size between the flexor tendon and the surrounding retinacular pulley system, most commonly at the level of the first annular (A1) pulley. When the subject extends the involved finger, the tendon will "catch" on the pulley, followed by an abrupt popping of the tendon through the pulley. This results in a difficulty flexing or extending the finger and the "triggering" phenomenon. Typically, a first course of treatment for trigger finger is corticosteroid injections into the tendon sheath to reduce inflammation. When corticosteroid injection is not or no longer effective, surgical division of the A1 pulley is indicated.

Carpal tunnel syndrome is an entrapment median neuropathy resulting from compression of the median nerve at the wrist in the carpal tunnel. Symptoms of carpal tunnel syndrome include tingling, numbness, weakness, or pain felt in the fingers supplied by the median nerve or in the palm. Repetitive tasks, force, posture, and vibration have been cited as causative or contributing factors to carpal tunnel syndrome. Palliative treatments for carpal tunnel syndrome include direct corticosteroid injections, splinting, oral corticosteroids and/or behavior modification. Failure of these methods within a reasonable period of time, and/or the presence of other contributing factors, indicates a need for surgical division of the carpal tunnel.

Other conditions involving the compression of a nerve by a ligament pulley or tunnel include Guyon's canal (or canal) syndrome, which is a compression of the ulnar nerve as it passes through Guyon's canal at the wrist; cubital tunnel syndrome, which is a compression of the ulnar nerve as it passes through the cubital tunnel at the elbow; radial tunnel syndrome, which is a compression of the radial nerve as it travels from the brachial plexus to the wrist and hand; and pronater teres syndrome, which is a compression neuropathy of the median nerve in the region of the elbow.

Conventional surgical techniques and equipment for pulley or tunnel release require a fairly large incision over the pulley or tunnel and spreading of the incision to allow viewing and instrument access. These techniques can require a longer period of recovery than endoscopic methods and have greater levels of post-operative pain due to the incision size and level of manipulation during the procedure.

Typically, endoscopic surgery has involved a number of steps and separate devices for performing pulley or tunnel division. After making an incision and opening a path to the pulley or tunnel using a blunt instrument, a cannula is inserted into the path. Briefly, in order to smoothly insert the cannula, the central lumen of the cannula must be filled with a device, such as an obturator. The obturator is then removed and an endoscope, or arthroscope, is inserted into the cannula to view the pulley or tunnel. The endoscope is then withdrawn from the cannula, a knife is either advanced into the cannula for division or a specialized knife assembly is affixed to the endoscope and the knife/endoscope assembly is advanced into the cannula for division. The present application fulfills a need in the art for a compact device for uniportal endoscopic pulley or tunnel release surgery that eliminates the need for a separate device, such as an obturator, for filling the cannula during insertion and eliminates the need to remove the endoscope in order to insert a blade or blade assembly.

SUMMARY

One aspect of the present application relates to an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly.

Another aspect of the present application relates to an endoscopic surgical kit, comprising an endoscope and an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly, and a scalpel.

Another aspect of the present application relates to a method for a performing a uniportal endoscopic surgical procedure on a target tissue using an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly.

Another aspect of the present application relates to slotted clear cannula comprising a cannula body having a proximate end and a distal end, and a slot extending from said proximate end of said cannula to the proximity of said distal end of said cannula, wherein the distal end of the cannula is closed.

Another aspect of the present application relates to a method for a performing a uniportal endoscopic surgical procedure on a target tissue using a slotted clear cannula comprising a cannula body having a proximal end and a distal end, and a slot extending from the proximal end of the cannula body to the proximity of the distal end of the cannula body, wherein the distal end is a closed end, the method comprising: establishing an entry portal in said subject; inserting said cannula into said entry portal; extending said cannula through said entry portal to said target tissue; advancing an endoscope into said cannula visualize a target tissue; and advancing a blade into said cannula until a desired cut is made on said target tissue.

Another aspect of the present application relates to a method for a performing a uniportal endoscopic surgical procedure on a target tissue using an endoscopic surgical kit comprising an endoscopic surgical device comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly, the kit further comprising a scalpel, and the method comprising: establishing an entry portal in said subject; inserting into said entry portal said cannula of said endoscopic surgical device; extending said cannula through said entry portal to said target tissue; advancing an endoscope into said cannula visualize a target tissue; and advancing said blade into said cannula until a desired cut is made on said target tissue.

Another aspect of the present application relates to a method for a performing a uniportal endoscopic surgical procedure on a target tissue of a hand using a slotted clear cannula comprising a cannula body having a proximal end and a distal end, and a slot extending from the proximal end of the cannula body to the proximity of the distal end of the cannula body, wherein the distal end is a closed end, the method comprising: establishing an entry portal in said subject; inserting said cannula into said entry portal; extending said cannula through said entry portal to said target tissue; advancing an endoscope into said cannula visualize a target tissue; and advancing a blade into said cannula until a desired cut is made on said target tissue.

BRIEF DESCRIPTION OF THE DRAWINGS

The present invention can be better understood by reference to the following drawings. The drawings are merely exemplary to illustrate certain features that may be used singularly or in combination with other features and the present invention should not be limited to the embodiments shown.

FIGS. 11A-E show perspective and cross-sectional views of the cannula element of the embodiment depicted in FIG. 9.

FIGS. 15A-E show perspective and cross-sectional views of the slide lock element of the embodiment depicted in FIG. 9.

FIGS. 16A-E show perspective and cross-sectional views of the rotary clip element of the embodiment depicted in FIG. 9.

FIGS. 17A-D show perspective views of the tube assembly element of the embodiment depicted in FIG. 9.

FIGS. 18A-C show perspective views of the blade tool element of the embodiment depicted in FIG. 9.

FIGS. 23A-E show perspective views of the scraper element of the embodiment depicted in FIG. 9.

FIGS. 28A-D show additional perspective views of the embodiment depicted in FIG. 27.

FIGS. 32A-F show perspective and cross-sectional views of the bottom shell of the housing of the embodiment depicted in FIG. 27.

FIGS. 33A-C show perspective and cross-sectional views of an embodiment of the blade tool element.

FIGS. 34A-E show perspective and cross-sectional views of the blade of FIGS. 28A-C.

FIGS. 37A-D show perspective views of an embodiment of an extension spring of the device.

FIGS. 41A-E show perspective and cross-sectional views of the revolver element of the embodiment depicted in FIG. 27.

FIGS. 43A-F show perspective and cross-sectional views of the bottom portion of an exemplary housing for a scope lock component of the embodiment of the device depicted in FIG. 27.

FIGS. 46A-D show perspective views of an embodiment of a locking plate of the device.

DETAILED DESCRIPTION

Figure 1:
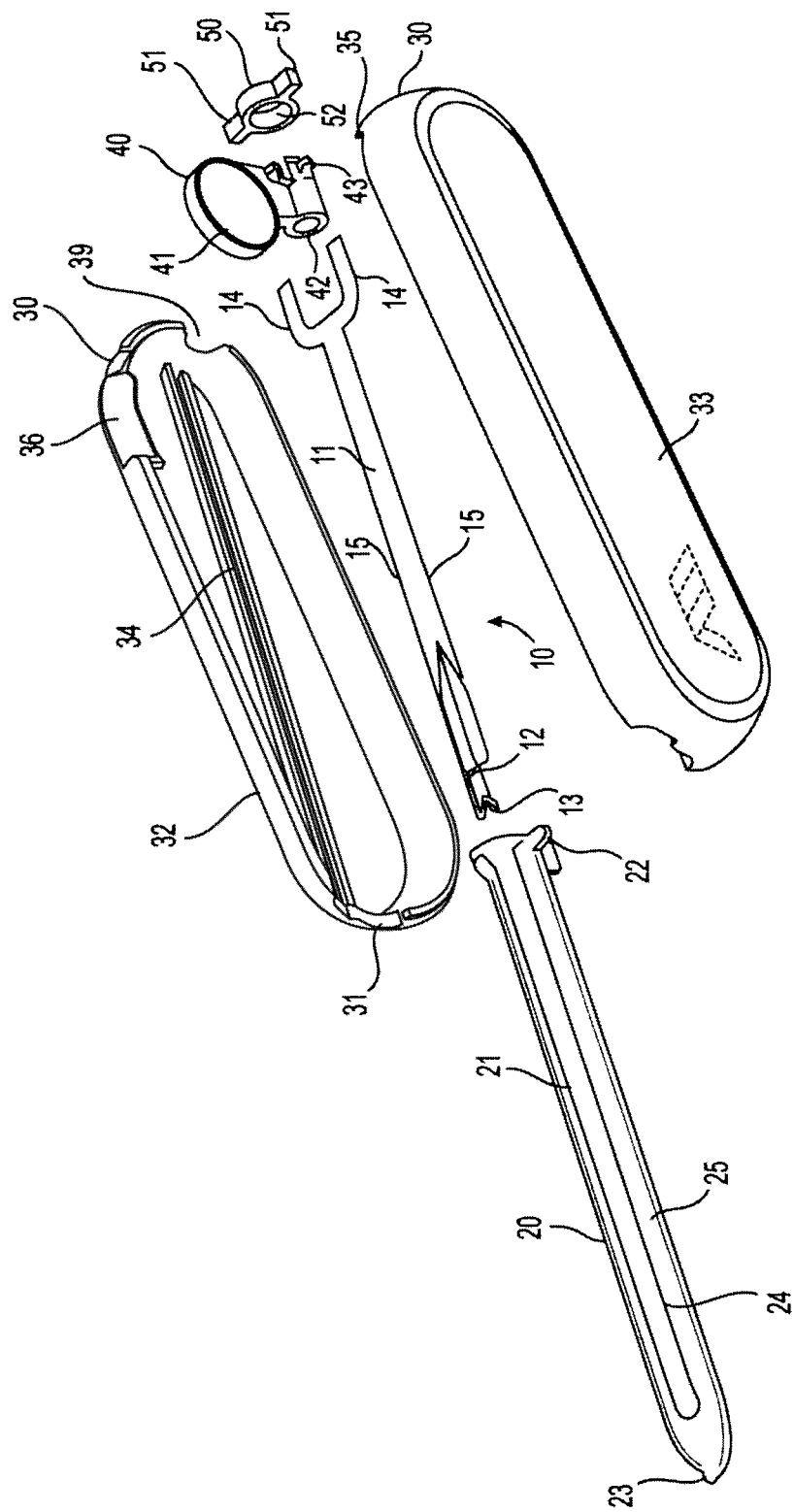
FIG. 1 is an exploded view of one embodiment of the device of the present application.

The following detailed description is presented to enable any person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. The present invention is not intended to be limited to the embodiments shown, but is to be accorded the widest possible scope consistent with the principles and features disclosed herein.

This description is intended to be read in connection with the accompanying drawings, which are to be considered part of the entire written description of this application. The drawing figures are not necessarily to scale and certain features of the application may be shown exaggerated in scale or in somewhat schematic form in the interest of clarity and conciseness. In the description, relative terms such as "front," "back," "up," "down," "top," "bottom," "upper," "lower," "distal," and "proximate" as well as derivatives thereof, should be construed to refer to the orientation as then described or as shown in the drawing figure under discussion. These relative terms are for convenience of description and normally are not intended to require a particular orientation. Terms concerning attachments, coupling and the like, such as "connected," "mounted," and "attached," refer to a relationship wherein structures are secured or attached to one another either directly or indirectly through intervening structures, as well as both movable or rigid attachments or relationships, unless expressly described otherwise.

The term "trigger finger," as used herein, also refers to "trigger digit," "trigger thumb," and "stenosing tendovaginitis."

As used herein, the terms "horizontal" and "vertical," and derivatives of those terms, are used in respect to their relationship to the plane defined by the slot in the cannula of the present application. "Vertical" refers to the plane that can, for example, pass through the slot of the cannula and bisect the cannula into two equal halves, while "horizontal" refers to a plane that is perpendicular to the vertical plane. The horizontal plane may be a level plane with respect to the length of the cannula or housing of the device, or may be at an angle to that level plane, allowing some upward or downward movement of elements moving along the horizontal plane with respect to the level plane.

The present application describes a compact device for performing endoscopic surgical procedures, comprising a clear cannula that is attached to a housing. The housing further comprises a blade that extends into the cannula, and a paddle for pushing the blade. In some embodiments, the housing further comprises a ring that secures the paddle to the housing, but allows the paddle to rotate side-to-side. The present assembly provides a convenient means for performing endoscopic surgical procedures with the elimination of the steps of inserting an obturator into the cannula for introducing the cannula into a portal, removing the obturator from the cannula, and removing an endoscope from the cannula so that a blade can be inserted and advanced into the cannula. The preassembled nature of the device also provides convenience for the practitioner in that the cannula and blade are available in a single package that requires no further assembly and can be used easily in an office setting without the need for some traditional endoscopic equipment that may be too expensive or cumbersome to use outside of a hospital. Additionally, the present device also can be easily transported and used in remote settings, such as by emergency medical personnel, first responders or military medical personnel.

The clear cannula of the present application has a closed distal end, allowing the cannula to be inserted through a portal (such as an incision) without the use of a cannula filling instrument, such as an obturator. The clear cannula allows the practitioner a 360 degree field of vision around the cannula through the use of an endoscope (or arthroscope) inserted into the central lumen of the cannula. This allows the practitioner to visualize all of the tissues surrounding the cannula from the point of initial insertion to and beyond the tissue targeted for a desired endoscopic surgical procedure. Some embodiments of the clear cannula comprise a blunt leading edge that is designed to serve as an obturator. The blunt leading edge allows the cannula to be inserted through an entry point and advanced to and/or beyond the target tissue without the need to first insert an instrument, such as an elevator, through the incision to first separate tissues and make a path for the cannula. An advantage of this design is that it eliminates a step in the surgical procedure. Another advantage is that it eliminates a step requiring a blind insertion of an instrument into a patient, as the insertion and advancement path of an elevator cannot be easily visualized by the practitioner. The present clear cannula with a sharpened leading edge, on the other hand, allows the practitioner to insert an endoscope into the clear cannula and visually monitor the insertion of the device and creation of a channel from the point of initial insertion to, or beyond, the target tissue. This allows the practitioner to penetrate into the tissue only as far as is necessary for performing the desired procedure, as well as avoiding tissues or structures that could be damaged, such as nerves or blood vessels, by blind insertion of a separating tool, such as an elevator.

The use of the present device is exemplified in this application for, but not limited to, endoscopic surgical division of a pulley or tunnel. Some other non-limiting uses for the present device include, for example, other divisions or partial separation of a tendon or ligament, cutting, dividing, separating or making an incision in connective tissue, muscle, cartilage, membranes, skin, other body tissues or organs or any other use of the device that can be envisioned or carried out by the practitioner. As used herein, the term "practitioner" refers to one of skill in the art or any other user of the present device.

Endoscopic surgical procedures that can be performed with a cannula or device of the present application include, but are not limited to, carpal tunnel release, Guyon's canal (or tunnel) release, cubital tunnel release, plantar fascia release, lateral release for patella realignment, release of radial tunnel, release of pronatar teres, release of trigger finger, release of lacertus fibrosus, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, and releasing the travel of a ligament or tendon through a pulley or tunnel. Additional endoscopic procedures that can be performed with a cannula or device of the present application include endoscopic surgical procedures on the spine, such as endoscopic discectomy for the treatment of degenerative disc disease, herniated discs, bulging discs, pinched nerves or sciatica. Endoscopic procedures that can be performed with a cannula or device of the present application also include endoscopic procedures on cranial and facial tissues, as well as fasciotomy release throughout the body. The cannula or device of the present application can be used for blood vessel, including vein or artery, harvesting throughout the body, for example to provide blood vessel graft material in conjunction with a coronary bypass procedure or for a reconstructive surgical procedure. Endoscopic procedures that can be performed with a cannula or device of the present application also include endoscopic procedures on the wrist and hand, including the palmar and dorsal sides of the hand. Endoscopic procedures that can be performed with a cannula or device of the present application on the hand also include the digits, including the thumb, index finger, middle finger, ring finger and little (pinky) finger.

Endoscopic surgical procedures that can be performed with a cannula or device of the present application, such as, but not limited to, a tunnel release procedure or trigger finger release, can be performed by approaching the target tissue through an incision or body opening on either the proximate or distal side of the target tissue.

One aspect of the present application relates to an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly.

In one embodiment, the scope lock assembly is affixed to the proximate end of the tube assembly.

In a further embodiment, the scope lock assembly is slidable with the tube assembly relative to the housing of the device. In another further embodiment, the scope lock assembly is lockable to the proximate end of the housing.

In another embodiment, the default condition of the scope lock assembly is immobilization of the viewing device relative to the tube assembly.

Another aspect of the present invention relates to an endoscopic surgical kit, comprising an endoscope and an endoscopic surgical device, comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly.

In another embodiment, the kit further comprises a scalpel.

In yet another embodiment, the kit further comprises an endoscope.

Another aspect of the present application relates to a method for a performing a uniportal endoscopic surgical procedure on a target tissue using an endoscopic surgical device, the device comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly; the method comprising: establishing an entry portal in said subject, inserting into said entry portal said cannula of said endoscopic surgical device; extending said cannula through said entry portal to said target tissue; advancing an endoscope into said cannula visualize a target tissue; and advancing said blade into said cannula until a desired cut is made on said target tissue.

In one embodiment, said establishing an entry portal comprises making an incision.

In another embodiment, said desired cut is division of said target tissue.

In still another embodiment, said method comprises advancing said scraper into said cannula to remove tenosynovium or ligament sheath.

In yet another embodiment, the uniportal endoscopic surgical procedure is selected from the group consisting of trigger finger release, Guyon's canal release, carpal tunnel release, cubital tunnel release, fascia release, lateral release for patella realignment, release of the extensor tendons, release of the posterior or other compartments of the leg, fascia release and blood vessel harvesting. In a further embodiment, the uniportal endoscopic surgical procedure is fascia release. In a still further embodiment, the fascia release is selected from the group consisting of forearm fasciotomy, plantar fasciotomy, fasciotomy for compartment syndrome, leg fasciotomy and fasciotomy of the hand.

In yet still another embodiment, the target tissue is selected from the group consisting of the A1 pulley, carpal transverse ligament, cubital tunnel, Guyon's canal, fascia and blood vessel. In a further embodiment, the blood vessel is a vein or artery.

Another aspect of the present application relates to a slotted clear cannula comprising a cannula body having a proximal end and a distal end, and a slot extending from the proximal end of the cannula body to the proximity of the distal end of the cannula body, wherein the distal end is a closed end.

In one embodiment, the distal end of the cannula body is tapered and forms an angle with the cannula body.

In another embodiment, the proximal end of the cannula body is configured to be engaged with another device and has a diameter that is larger than the diameter of the cannula body.

In still another embodiment, the cannula body is graded between the proximal end of the cannula body and distal end of the cannula body.

In yet another embodiment, the distal end of the cannula body comprises a sharpened edge for tissue separation.

Another aspect of the present application relates to a method for a performing a uniportal endoscopic surgical procedure on a target tissue using a slotted clear cannula comprising a cannula body having a proximal end and a distal end, and a slot extending from the proximal end of the cannula body to the proximity of the distal end of the cannula body, wherein the distal end is a closed end, the method comprising: establishing an entry portal in said subject; inserting said cannula into said entry portal; extending said cannula through said entry portal to said target tissue; advancing an endoscope into said cannula visualize a target tissue; and advancing a blade into said cannula until a desired cut is made on said target tissue.

In one embodiment, the method comprises establishing an entry portal comprises making an incision.

In another embodiment, the desired cut is division of said target tissue.

In still another embodiment, the distal end of the cannula body comprises a sharpened edge for tissue separation.

In yet another embodiment, the method further comprises advancing a scraper into said cannula to remove tenosynovium or ligament sheath.

In yet still another embodiment, the uniportal endoscopic surgical procedure is selected from the group consisting of trigger finger release, Guyon's canal release, carpal tunnel release, cubital tunnel release, fascia release, lateral release for patella realignment, release of the extensor tendons, release of the posterior or other compartments of the leg, fascia release and blood vessel harvesting.

Another aspect of the present application relates to a method for a performing a uniportal endoscopic surgical procedure on a target tissue using an endoscopic surgical kit comprising an endoscopic surgical device comprising: (a) a housing having a proximate end and a distal end; (b) a slotted clear cannula attached to said distal end of said housing, said slotted clear cannula comprises a cannula body having a proximate end and a distal end, and a slot extending from said proximate end of said cannula to the proximity of said distal end of said cannula; (c) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (d) a tube assembly having a proximate end and a distal end, said distal end of said tube assembly is located within said housing and extends through said revolver, said distal end of the tube assembly is capable of entering said slotted clear cannula from said proximate end of said clear cannula; and (e) a scope lock assembly for holding a viewing device in a stationary position relative to the tube assembly, the kit further comprising a scalpel, and the method comprising: establishing an entry portal in said subject; inserting into said entry portal said cannula of said endoscopic surgical device; extending said cannula through said entry portal to said target tissue; advancing an endoscope into said cannula visualize a target tissue; and advancing said blade into said cannula until a desired cut is made on said target tissue.

In one embodiment, said establishing an entry portal comprises making an incision. In a further embodiment, said incision is made with said scalpel.

Another aspect of the present application relates to a method for a performing a uniportal endoscopic surgical procedure on a target tissue of a hand using a slotted clear cannula comprising a cannula body having a proximal end and a distal end, and a slot extending from the proximal end of the cannula body to the proximity of the distal end of the cannula body, wherein the distal end is a closed end, the method comprising: establishing an entry portal in said subject; inserting said cannula into said entry portal; extending said cannula through said entry portal to said target tissue; advancing an endoscope into said cannula visualize a target tissue; and advancing a blade into said cannula until a desired cut is made on said target tissue.

In one embodiment, said establishing an entry portal comprises making an incision. In a further embodiment, said target tissue is the flexor tendon sheath. In a still further embodiment, said incision is made to the proximate side of the flexor tendon sheath. In another still further embodiment, said incision is made to the distal side of the flexor tendon sheath.

In another embodiment, said slotted clear cannula is attached to the distal end of an endoscopic surgical device, the endoscopic surgical device further comprising: (a) a housing having a proximate end and a distal end; (b) a revolver assembly located within said housing, comprising: a slide lock having a proximate end, a distal end and two notches at said distal end; a scraper; a blade assembly; and a circular revolver body comprising a selector switch; wherein said scraper and said blade reside at said two notches of said slide lock in a pre-deployment position and wherein said selector switch allows selection of said scraper or said blade for deployment; (c) a tube assembly having a proximate end and a distal end, said distal end of said tube assembly is located within said housing and extends through said revolver, said distal end of the tube assembly is capable of entering said slotted clear cannula from said proximate end of said clear cannula; and (d) a scope lock assembly for holding a viewing device in a stationary position relative to the tube assembly.

Linear Operated Device

FIG. 1 shows an exemplary device of the present application. The device comprises a blade 10, a slotted clear cannula 20, and a housing 30. The device may further include a pusher paddle 40, and may still further include a retainer ring 50.

The blade 10 comprises a horizontally-oriented pushing component 11 and a vertically-oriented cutting component 12. The cutting component 12 further comprises a sharpened cutting surface 13 at the forward end, which is the end of the blade most proximal to the cannula 20 of the device. The cutting surface 13 may be single-beveled or double-beveled.

In some embodiments, the cutting surface 13 of the blade is a single cutting surface. In some further embodiments, that single cutting surface is angled downward such that the upper end of the cutting surface is forward of the lower end of the cutting surface. In other further embodiments, that single cutting surface has a concave curve and is semi-circular or crescent shaped.

In other embodiments, the cutting surface 13 of the cutting component 12 is divided into an upper cutting surface and a lower cutting surface that are at an angle to one another and meet at a central crotch.

The design of the present blade 10 is such that it is usable in endoscopic surgery in a manner that allows the practitioner to extend the blade 10 through the cannula to the target tissue without damage to surrounding tissue and/or organs. The cutting component 12 of blade 10 is made from materials commonly used for surgical blades or scalpels, such materials include, but are not limited to, hardened and tempered steel, stainless steel, high carbon steel, titanium, alloys and ceramic.

In particular embodiments, the cutting component 12 of the blade 10 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the cutting component 12 of the blade 10 is made from Hitachi GIN-5 SST-MODIFIED 440-A stainless steel. The cutting component 12 of the blade 10 is optionally flash electropolished. The cutting edges are machine finished and must be sharp. In a particular embodiment, the steel of the cutting component 12 of the blade 10 is heat-treated to Rockwell C hardness of about 50-72. In a more particular embodiment, the steel of the cutting component 12 of the blade 10 is heat-treated to Rockwell C hardness of 58-64.

In particular embodiments, the entire blade 10 is cut from a single sheet of, or is cast from, a material commonly used for surgical blades or scalpels. The cutting component 12 is then bent into a vertical orientation that is perpendicular to the horizontal orientation of the pushing component 11. In some embodiments, the bevel(s) of the cutting surface 13 are ground prior to bending. In other embodiments, the bevel(s) of the cutting surface 13 are ground after bending.

In other embodiments, the pushing component 11 and cutting component 12 of the blade 10 are fabricated separately (by cutting or casting) and affixed to one another in their respective proper orientations. In some further embodiments, the pushing component 11 and cutting component 12 are fabricated from the same material. In other further embodiments, the pushing component 11 and cutting component 12 are fabricated from different materials, but at least the cutting component 12 is fabricated from a material commonly used for surgical blades or scalpels. In such a case, the pushing component 11 of the blade 10 may be fabricated from any suitable material providing adequate strength and rigidity for pushing the cutting component including, but not limited to, plastics, polycarbonate, hardened and tempered steel, stainless steel, high carbon steel, titanium, alloys and ceramic. Affixing of the cutting component 12 to the pushing component 11 may be accomplished by any means known in the art, such as the use of a suitable adhesive or by welding, including laser welding. In a particular embodiment, the strength of the bond between the pushing component 11 and the cutting component 12 is tested by applying torque to the unit, for example about 10 in-lbs of torque.

In particular embodiments, the blade 10 further comprises tabs 14 at the end of the pushing component 11 distal to the cutting component 12. In some embodiments, the tabs 14 extend outward to the sides of the blade 10 in the same horizontal plane as the pushing component 11, although in some embodiments, the tabs 14 may also be at an angle to that horizontal plane, as appropriate for the application. As used herein, the term "tabs" refers to either a single tab structure, two tab structures, or any other multiple as appropriate.

The tabs 14 are slidably engaged with the case or housing 30 in a manner to be further described below.

The cannula 20 is made of a clear plastic material so that the entirety of the surrounding tissue can be viewed with an endoscope. The cannula 20 is slotted along its top, with the slot 21 being contiguous with the open end 22 that is proximal to the housing 30. In some embodiments, the distal end 23 of the cannula 20 is closed, such that the cannula 20 can be inserted into a channel made through body tissue without the use of an obturator. In particular embodiments, the closed distal end 23 of the cannula is tapered, but is sufficiently blunted such that it does not damage bodily tissues as it is advanced though an incision and channel through bodily tissue, or through a natural body opening.

The cannula 20 engages with the blade 10 of the device such that the cutting component 12 inserts into and is slidably engaged with the slot 21.

In some embodiments, the cannula 20 further internally comprises horizontal blade guidance tracks 24 perpendicular to the plane of and below the slot 21. The sides 15 of the pushing component 11 of the blade 10 slidably engage with the horizontal blade guidance tracks 24, in order to allow the accurate advancement of the cutting component 12 of the blade 10 through the slot 21. In some further embodiments, the height of the horizontal blade guidance tracks 24 is level with respect to the distance from the slot 21, such that the distance the cutting surface 13 protrudes through the slot 21 is the same over the entire course of travel from the proximal end 22 of the cannula 20 to the distal end 23 of the cannula 20. In other further embodiments, the height of the horizontal blade guidance tracks 24 is at an angle with respect to the distance from the slot 21, such that the distance the cutting surface 13 protrudes through the slot 21 is lower at or near the proximal end 22 of the cannula 20 and higher at or near the distal end 23 of the cannula 20.

In some embodiments, the cannula 20 further comprises a channel 25 for the slidable insertion a viewing device, such as an endoscope. In some embodiments, the channel 25 is located below the horizontal blade guidance tracks 24. In some embodiments, the channel 25 and the horizontal blade guidance tracks 24 form a single contiguous lumen that is also contiguous with the slot 21. In other embodiments, there is a layer of material molded as part of the cannula 20 between the channel 25 and the horizontal blade guidance tracks 24, such that the lumen of the channel 25 is physically separate from the lumen contiguous with the slot 21 and comprising the horizontal blade guidance tracks 24.

In some embodiments, the proximal end 22 of the cannula 20 is adapted to engage with a connection point 31 on the front end of the housing 30. The attachment can be by any means known in the art, such as, but not limited to, adhesives, tabs, welds, laser welds, locking mechanism, twist-lock, or friction fitting. In order to provide a stable platform for endoscopic surgical procedures using the device, the attachment of the cannula 20 to the housing 30 is such that, when assembled, the cannula 20 cannot move in relation to the housing 30.

In some embodiments, the housing 30 of the device comprises two halves 32, 33 that mate to one another to form a single housing 30. In some embodiments, the housing 30 may be formed as a single piece or comprise three or more pieces.

The interior of the housing 30 comprises a guidance slot 34 on each side of the housing such that the two guidance slots 34 are horizontally opposed to one another. The tabs 14 of the blade 10 are slidably engaged with the horizontally opposed guidance slots 34. In some embodiments, the height of the horizontally opposed guidance slots 34 is parallel to with respect to a horizontal plane that would bisect the cannula 20 into two equal halves. In other embodiments, the height of the horizontally opposed guidance slots 34 is at an angle with respect to a horizontal plane that would bisect the cannula 20 into two equal halves, such that the end of the horizontally opposed guidance slots 34 distal to the cannula 20 is lower in the device with respect to the end of the horizontally opposed guidance slots 34 proximal to the cannula 20.

When the tabs 14 are drawn back in the horizontally opposed guidance slots 34, the cutting component 12 is contained within the proximate end 22 of the slot 21 of the cannula 20 and the cutting surface 13 is not protruded outside the device. As the tabs 14 are advanced in the horizontally opposed guidance slots 34 toward the connection point 31 with the cannula 20, the cutting component 12 slides in the proximate direction of the slot 21 of the cannula 20 and moves the cutting surface 13 toward the proximate end 23 of the cannula 20.

In some embodiments, the device comprises a paddle 40 that contacts the blade 10 behind or between the tabs 14. The paddle 40 comprises a grip area 41 that protrudes out of the housing 30 through a slot 35. The blade 10 is slidably advanced along the horizontally opposed guidance slots 34 by advancing the paddle 40 towards the cannula 20 through the slot 35, causing the contact area 42 of the paddle 40 to push against the pushing component 11 of the blade 10.

In some embodiments, the paddle 40 comprises at least one arm that extends forward of the tabs 14 that allows the paddle 40 to capture the tab 14 and pull the blade 10 back to a withdrawn position following completion of an endoscopic surgical procedure.

In some embodiments, the paddle 40 is secured in the device by a retaining ring 50. The retaining ring 50 comprises wings 51 that slidably interact with the horizontally opposed guidance slots 34 of the housing 30. The retaining ring 50 further comprises an attachment ring 52 that connects to the connection region 43 of the paddle 40. The connection region 43 of the paddle 40 may comprise any means known in the art for connecting the paddle 40 to the retaining ring 50. For example, the connection region 43 may comprise tabs that extend through and entrap the attachment ring 52. In some embodiments, the connection between the connection region 43 and the attachment ring 52 allows the paddle 40 to rotate side-to-side in relation to the retaining ring and the blade 10.

In some embodiments, the paddle 40 can be retained, parked or locked in a position fully distal to the cannula 20 by rotating the grip area 41 of the paddle 40 into, for example, a notch 36 in the housing 30.

In some embodiments, the housing 30 further comprises an opening 39 at the end distal to the cannula 20 through which an endoscope can be inserted. The endoscope is fed through the opening 39 and under the blade 10 to be inserted into the channel 25 of the catheter 20. This allows direct visualization of the surgical site and the surrounding tissue before, during and after performing an endoscopic surgical procedure with the present device.

Another aspect of the present application relates to a slotted clear cannula having a closed end such that the cannula can be inserted into an incision or natural body opening and into a passage through body tissue without the use of a device, such as an obturator, filling the lumen of the cannula for insertion. In particular embodiments, the closed end of the cannula is tapered, but is sufficiently blunted such that it does not damage bodily tissues as it is advanced though an incision and channel through bodily tissue, or through a natural body opening. In another particular embodiment, the slot is contiguous with the open end of the cannula opposite the closed end.

Rotationally Operated Devices

Figure 2:
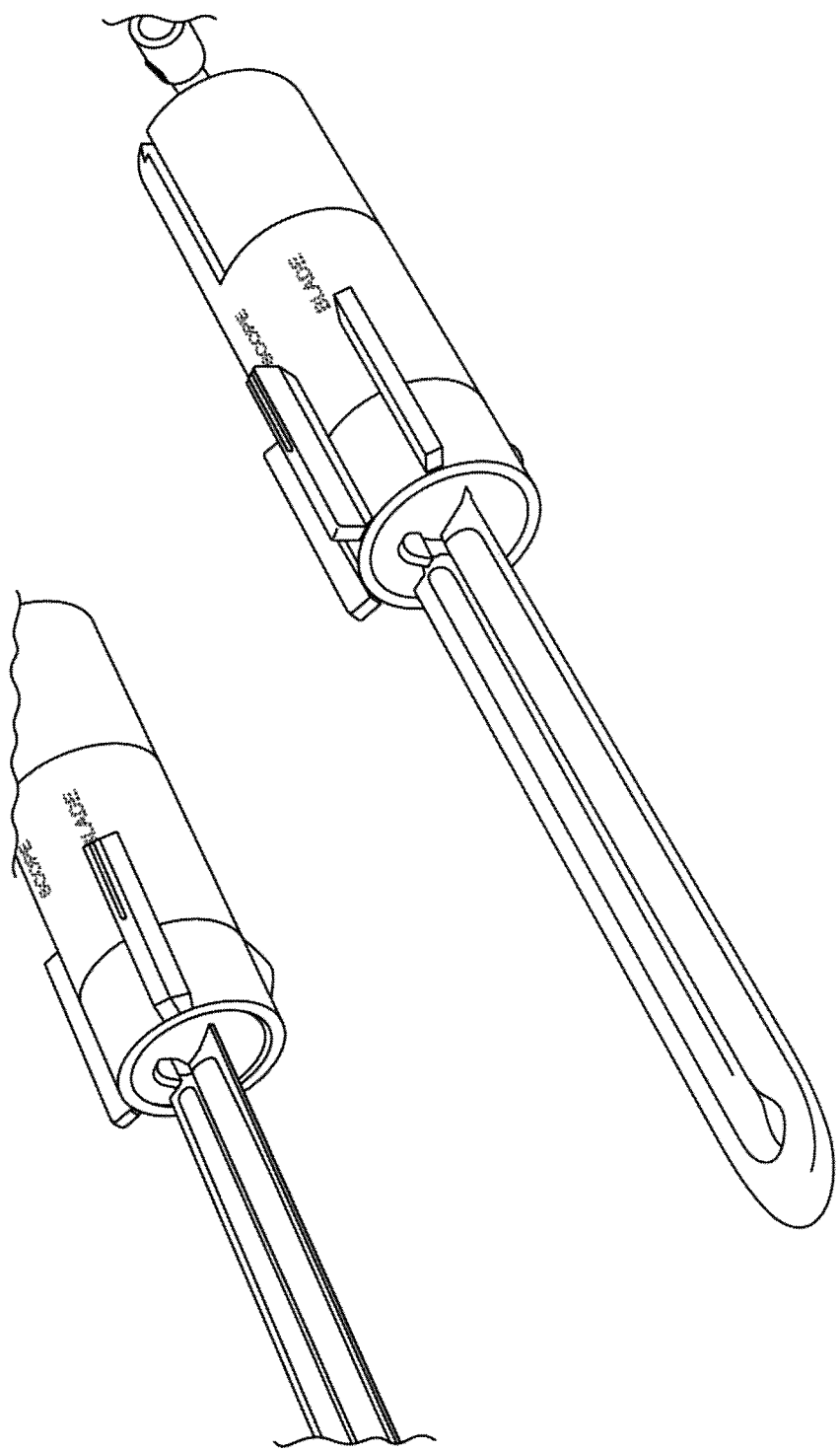
FIG. 2 is a perspective view of another embodiment of the device of the present application.
Figure 3:
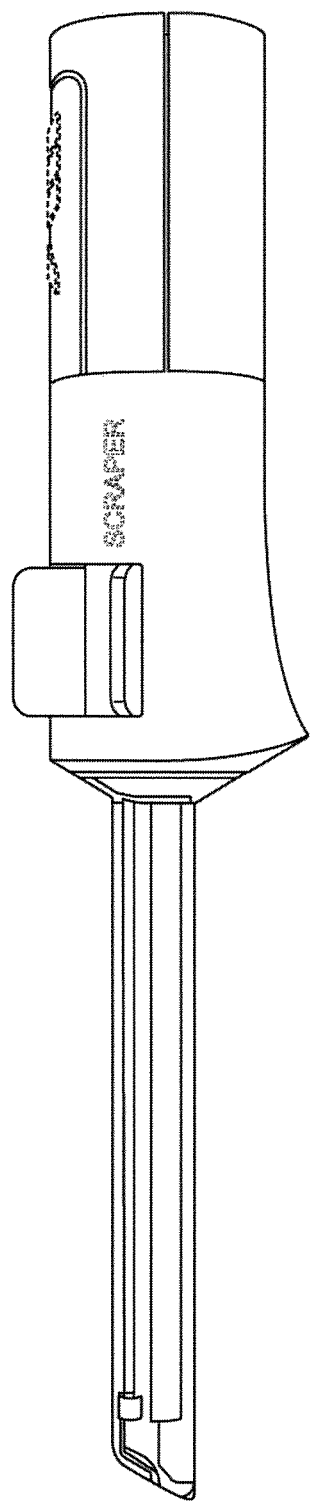
FIG. 3 is a perspective view of another embodiment of the device of the present application.

FIGS. 2 and 3 show embodiments of the present application wherein the device comprises a rotational switch for selecting the tool to advance into the cannula. FIG. 2 shows an embodiment comprising selection positions for advancing the endoscope alone into the cannula and for advancing a blade along the endoscope into the cannula. FIG. 3 shows an alternate embodiment, wherein the device further comprises a selectable scraper that can be advanced along the endoscope into the cannula.

Figure 4:
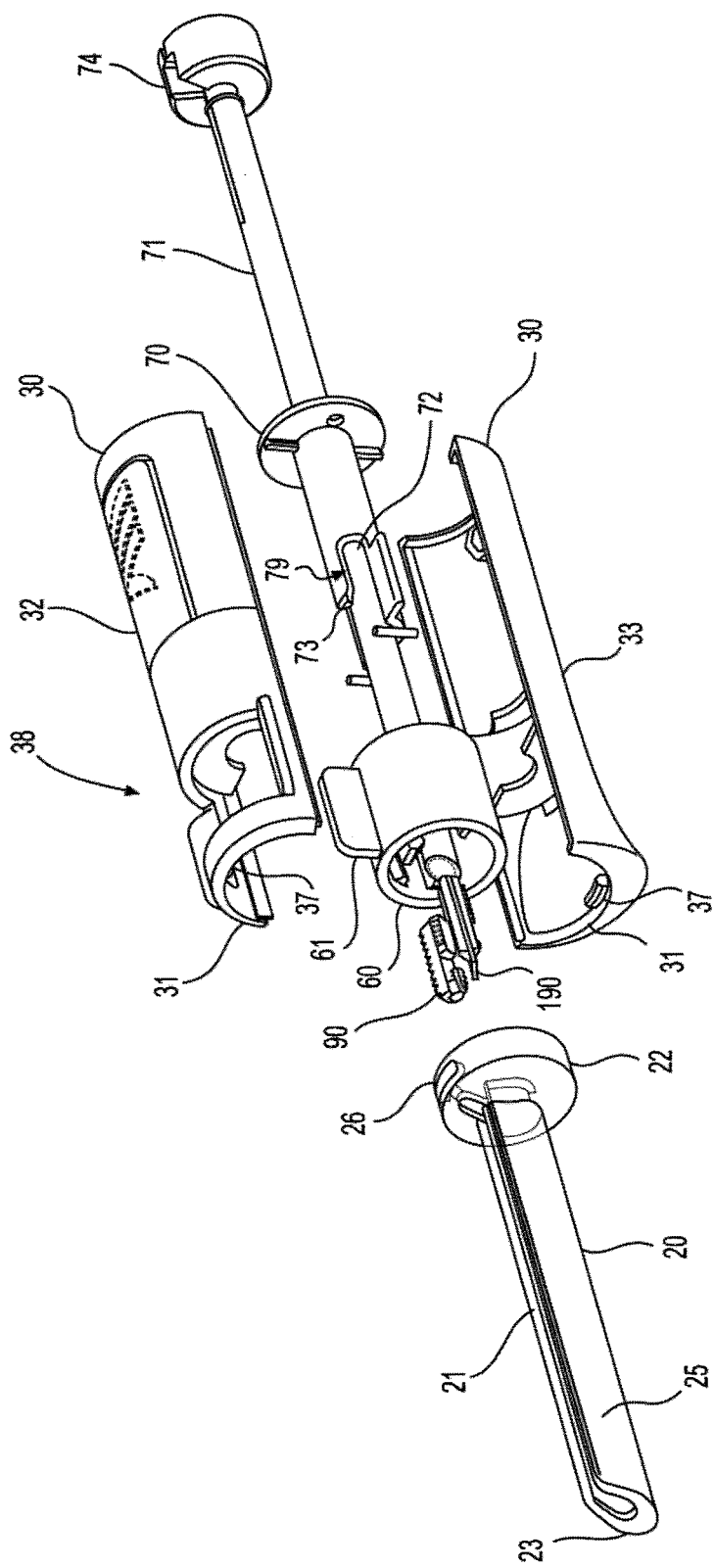
FIG. 4 is an exploded view of the embodiment of the embodiment depicted in FIG. 3.

FIG. 4 depicts an exploded view of the present device of FIG. 3. The housing 30 is cylindrical in shape and is comprised of two halves 32,33. The proximal end 22 of the cannula 20 is adapted to engage with a connection point 31 on the front end of the housing 30. In some embodiments, the proximal end 22 of the cannula 20 comprises depressions 26 that engage with tabs (or pins) 37 at the connection point 31 on the front end of the housing 30. As used herein, the term "depression" is understood to include, but is not limited to, depressions that do not penetrate completely through the material of the cannula, as well as holes or slots that penetrate completely through the material of the cannula.

The housing 30 further includes an opening 38 that can be located in either half 32,33 of the housing. In some embodiments, the opening 38 may span the junction between the halves 32,33 of the housing 30, being located partially in each half. The opening 38 is located adjacent to an internal revolver 60 that comprises a selector switch 61 that protrudes through the opening 38.

Still referring to FIG. 4, the device further comprises an slide lock 70 (or inner sleeve 70) that encircles a guidance tube or tube assembly 71. The slide lock 70 comprises notches 72,73 and a tub 79 separating the notches 72,73, at its distal end that provide pre-deployment resting places for a blade 80 and a scraper 90. The slide lock 70 works in concert with the revolver 60 in order to bring the blade 80 or scraper 90 into the proper orientation for deployment into the slot 21 of the cannula 20. The tube assembly 71 provides a path for deploying an endoscope through the device and into the cannula 20. The tube assembly 71 also provides, at its distal end, a mounting point or tube locator 78 (shown in FIG. 8A) that the blade 80 or scraper 90 is rotated onto for deployment. At the proximate end of the housing, the tube assembly passes through a stabilizer ring 74, which mounts into, and seals, the proximate end of the housing. The tube assembly 71 is advanced along the deployed endoscope into the cannula 20, thereby deploying the blade 80 or scraper 90 into the slot 21 of the cannula 20.

Figure 5:
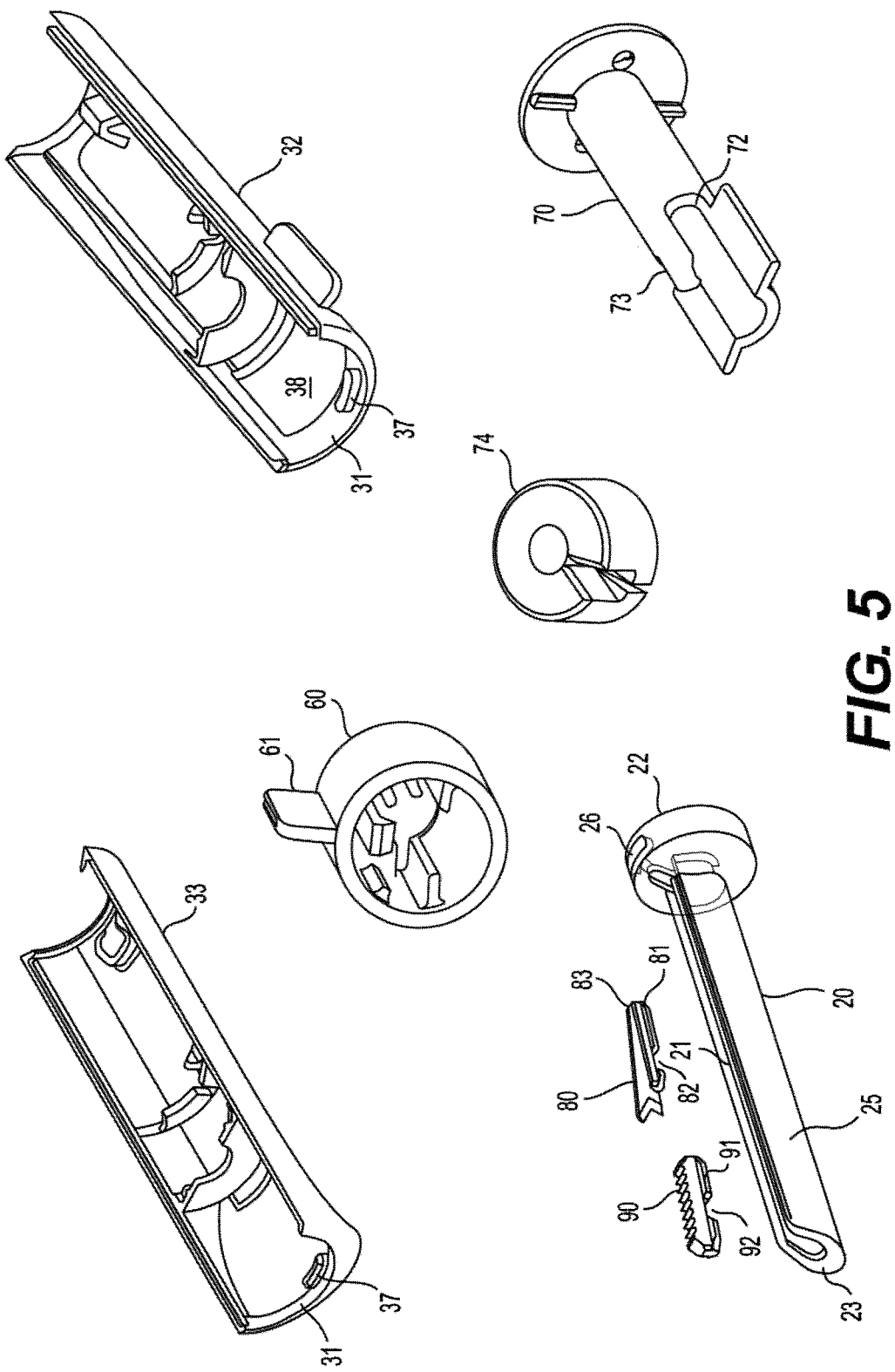
FIG. 5 shows individual components of the embodiment depicted in FIG. 3.

Turning to FIG. 5, a number of components of the device depicted in FIG. 3 are shown separately from one another. It is understood that the individual elements of the device are not limited to the exact configuration depicted in the figures herein. Any design of particular elements of the device that can be envisioned by one of ordinary skill in the art to perform the same function in concert with other elements is included as part of the present disclosure.

Also in FIG. 5, the blade 80 comprises a base 81 that allows the blade 80 to be secure in its pre-deployment notch 72 of the slide lock 70. When the blade 80 is rotated into deployment orientation, the notch 82 in the base 81 engages the mounting point 78 (shown in FIG. 8A) on the distal end of the guidance tube 71. As the blade 80 is distally deployed into the slot 21 of the cannula 20, the base 81 retains the blade 80 in the device by underlapping the sides of the slot 21 within the channel 25 of the cannula 20. Additionally, to prevent any unwanted side-to-side motion of the blade 80 as it is deployed distally through the slot 21 of the cannula 20, in some embodiments the blade further comprises a ridge 83 that fills the slot side-to-side. Additionally, the engagement of the notch 82 with the mounting point 78 allows the blade 80 to be safely retracted back into the housing 30 following usage of the blade 80 for an endoscopic surgical procedure.

Still referring to FIG. 5, the scraper 90 comprises a base 91 that allows the scraper 90 to be secure in its pre-deployment notch 73 of the slide lock 70. When the scraper 90 is rotated into deployment orientation, the notch 92 in the base 91 engages the mounting point 78 (shown in FIG. 8A) on the distal end of the guidance tube 71. As the scraper 90 is distally deployed into the slot 21 of the cannula 20, the base 91 retains the scraper 90 in the device by underlapping the sides of the slot 21 within the channel 25 of the cannula 20. Additionally, the engagement of the notch 92 with the mounting point 78 allows the scraper 90 to be safely retracted back into the housing 30 following usage of the scraper 90 for an endoscopic surgical procedure.

Figure 6:
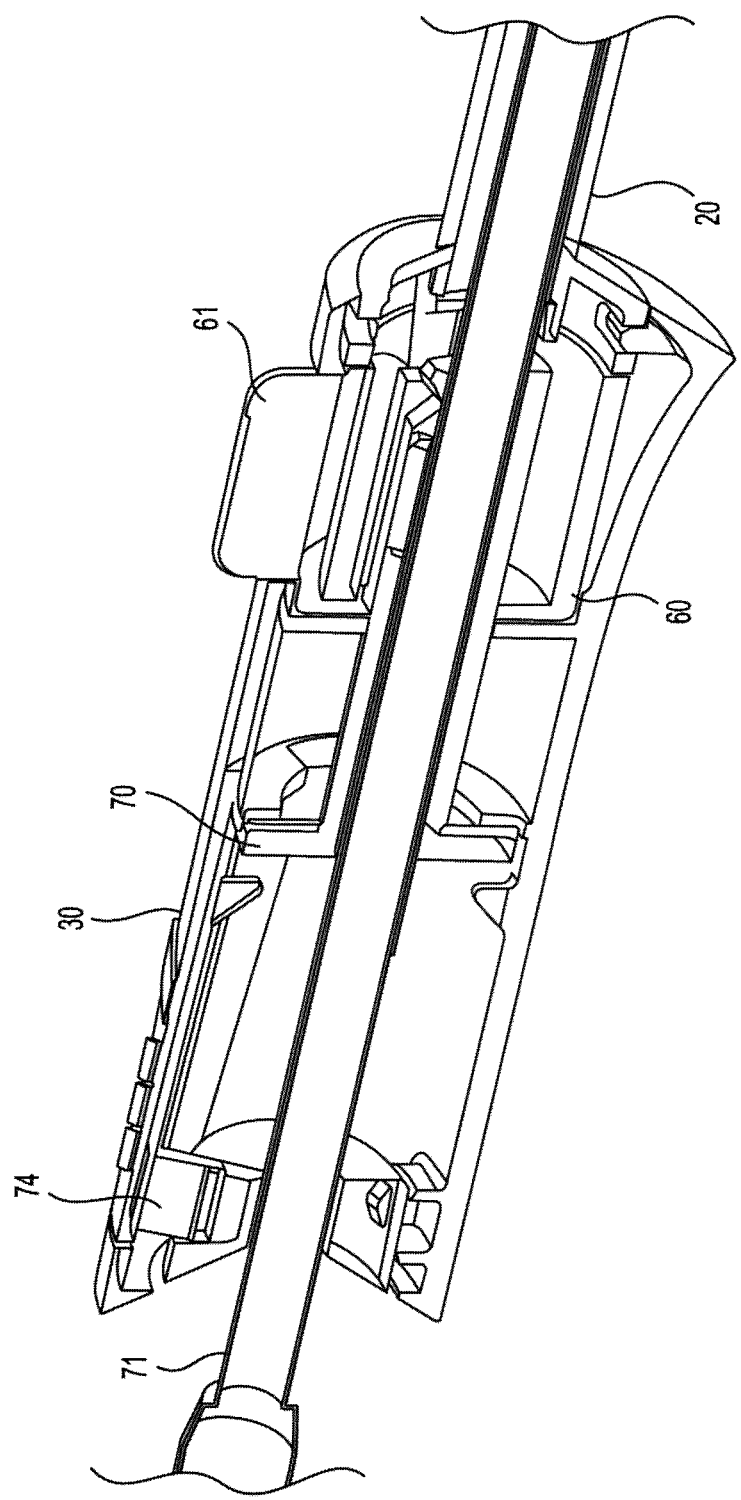
FIG. 6 is a cutaway view of the embodiment of the embodiment depicted in FIG. 3.

Turning to FIG. 6, a cutaway drawing is shown that depicts the passage of the guidance tube or tube assembly 71 through the slide lock 70 and into the cannula 20.

Figure 7:
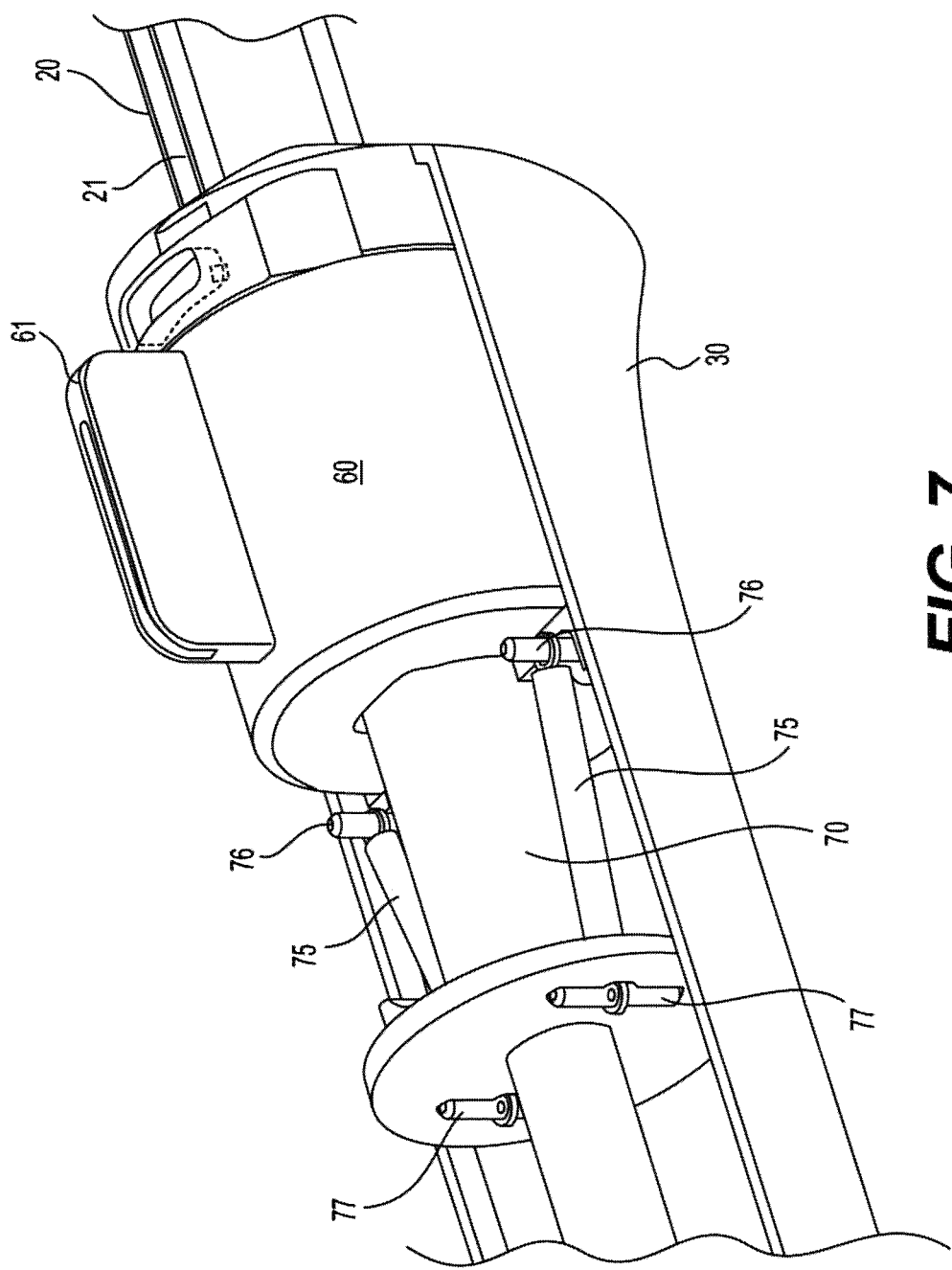
FIG. 7 is an exploded view of individual components of the embodiment depicted in FIG. 3.

FIG. 7 is a cutaway drawing showing an exemplary relationship of the slide lock 70 to the revolver 60 of the device. The slide lock 70 extends into the revolver 60 and the pre-deployment slots 72,73 holding the blade 80 and the scraper 90 are located inside the revolver 60. In an exemplary configuration, springs 75 are attached to pins 76 located on the revolver 60. The springs 75 extend to pins 77 that secure the opposite end of the springs to the slide lock 70. The springs 75 auto center the revolver 60 within the device. Upon rotation of the revolver 60, the springs 75 activate detents for the three modes: 1) deployment of the endoscope, 2) orientation of the scraper 90 in deployment configuration, and 3) orientation of the blade 80 in deployment configuration.

Figure 8A:
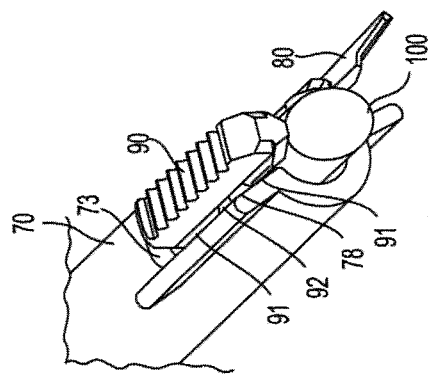
FIGS. 8A-F show the orientation of the internal components in side view (A, C, E) and end view (B, D, F) of the embodiment of FIG. 3 for the advancement of an endoscope alone (A, B), an endoscope with a scraper (C, D) or an endoscope with a blade (E, F).
Figure 8B:
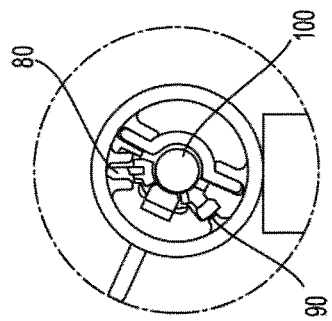

FIGS. 8A-F show the rotation of the slide lock corresponding to the three modes. FIG. 8A, viewing from above, and 8B, viewing from a distal position, are a depiction of the first mode, wherein the an endoscope 100 can be advanced through the guidance tube 71 into the cannula 20, without the deployment of the scraper 90 or the blade 80. The mounting point 78 is not engaged with either the blade 80 or the scraper 90, therefore preventing the deployment of either tool in this mode.

Figure 8C:
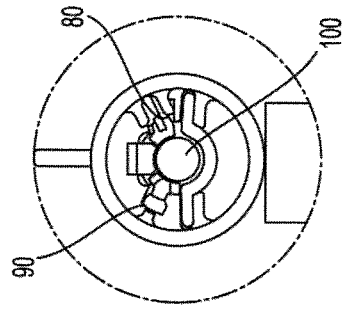

FIGS. 8C, viewing from above, and 8D, viewing from a distal position, are a depiction of the second mode, wherein the revolver 60 has been turned to select the scraper 90. The slide lock 70 is rotated in concert with the revolver 60 to bring the scraper 90 into deployment orientation. The slot 92 in the base 91 of the scraper 90 is rotated to engage the mounting point 78 on the guiding tube (hidden). The guiding tube is then pushed distally into the cannula 20 with the scraper 90 protruding through the slot 21. Following use of the scraper 90, the guiding tube is retracted from the cannula 20 and the revolver 60 is returned to the first mode, restoring the scraper to its pre-deployment configuration of FIGS. 8A-B.

Figure 8E:
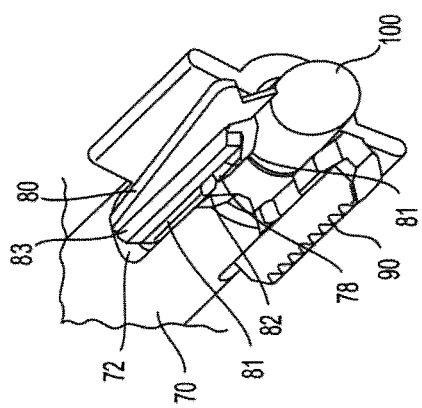
Figure 8D:
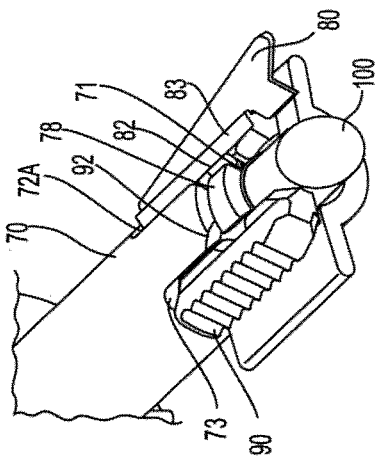
Figure 8F:
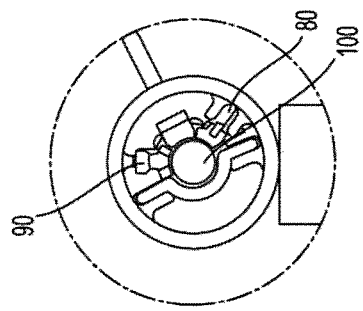

FIGS. 8E, viewing from above, and 8F, viewing from a distal position, are a depiction of the third mode, wherein the revolver 60 has been turned to select the blade 80. The slide lock 70 is rotated in concert with the revolver 60 to bring the blade 80 into deployment orientation. The slot 82 in the base 81 of the blade 80 is rotated to engage the mounting point 78 on the guiding tube (hidden). The guiding tube is then pushed distally into the cannula 20 with the blade 80 protruding through the slot 21. Following use of the blade 80, the guiding tube is retracted from the cannula 20 and the revolver 60 is returned to the first mode, restoring the blade 80 to its pre-deployment configuration of FIGS. 8A-B.

Figure 9:
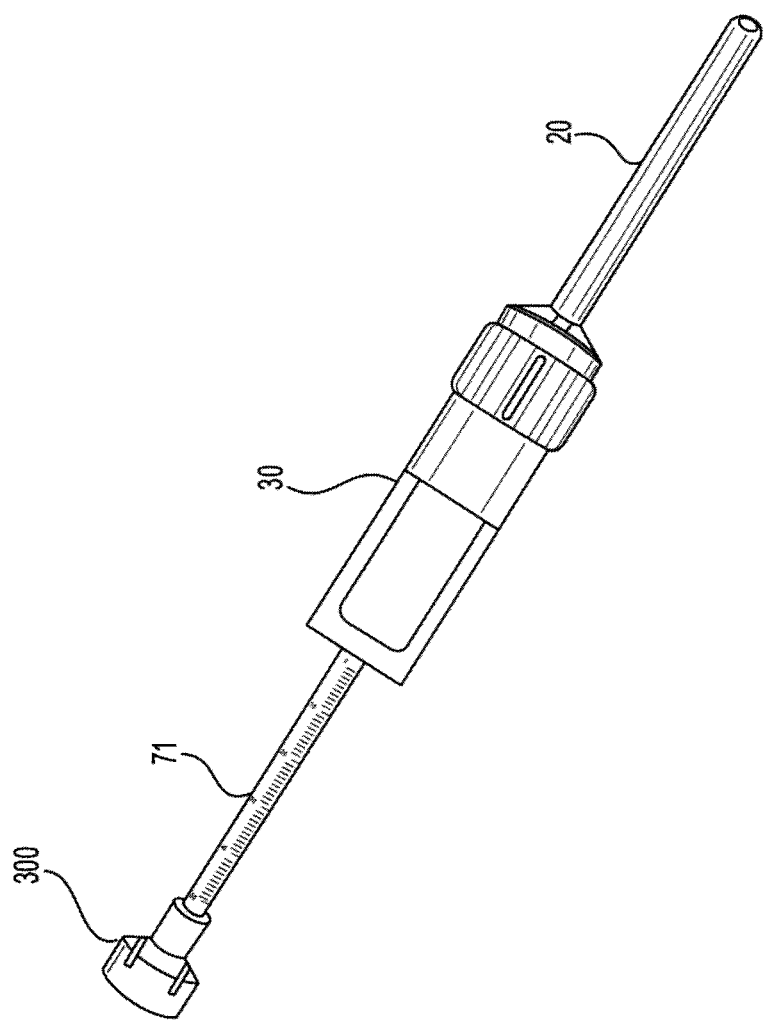
FIG. 9 is a perspective view of another embodiment of the device of the present application.

FIG. 9 is a perspective view from above an embodiment of the device showing, in particular, the cannula 20, housing 30 and tube assembly 71 as they appear in the assembled device prior to deployment of the tube assembly 71 into the cannula 20 with the scraper tool or blade assembly.

Figure 10:
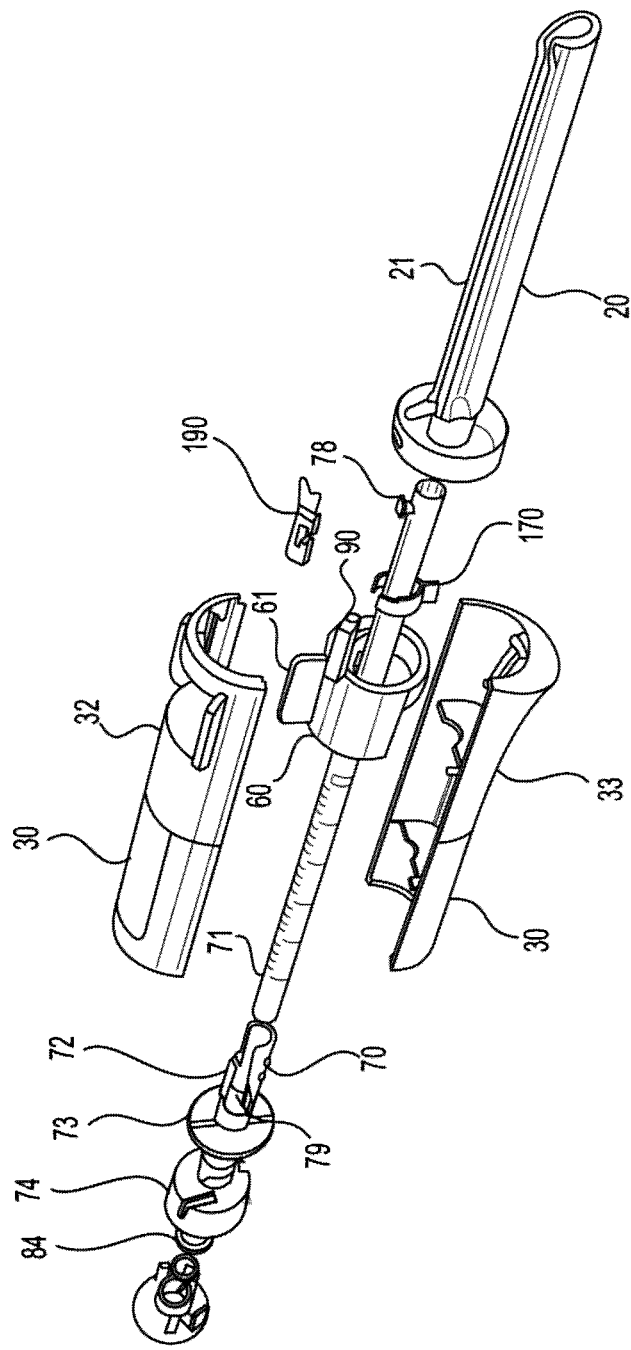
FIG. 10 is an exploded view of the embodiment depicted in FIG. 9.

FIG. 10 is an exploded view of the embodiment of the device shown in FIG. 9. FIG. 10 shows the cannula 20 which joins to the distal end of top half 32 and bottom half 33 of the housing 30. Interior to the housing 30 is the revolver 60, having a selector switch 61 for choosing the "BLADE," "SCOPE," or "SCRAPER" position of the slide lock 70, which is positioned inside the revolver 60. The blade 80 and scraper 90 tools are parked in notches 72,73 in the slide lock 70 and are retained there when not deployed by a rotary clip 170. The tube assembly 71 passes through the slide lock 70 within the housing 30. The distal end of the tube assembly 71 extends and is deployable into the cannula 20. The tube assembly 71 comprises near its distal end a tube locator 78 that the blade 80 or scraper 90 tool is engaged with for deployment into the cannula 20. The tube assembly 71 further comprises, at its proximate end, a tube stop 84 that prevents the proximate end of the tube assembly 71 from passing through the stabilizer ring 74 mounted in the rear of the housing 30. The tube assembly 71 has a longitudinal central lumen that accommodates the insertion of an endoscope through the tube assembly 71 and into the clear cannula 20 in order to visualize the tissue surrounding said cannula 20 and to observe the surgical procedure performed with the compact endoscopic surgical device. In some embodiments, the tube stop 84 is gripped by the practitioner or engaged to a grippable attachment 300 (FIG. 9) to allow the tube assembly to be operated manually for advancement or withdrawal of the tube assembly 71. In other embodiments, the tube stop 84 is engaged to an apparatus or machine for automatic or remote control of advancement or withdrawal of the tube assembly 71.

FIGS. 11A-E show details of the clear cannula element of the device. FIG. 11A shows the cannula 20 from the top, showing the slot 21 extending longitudinally from the proximity of the proximal end 22 to the proximity of the distal end 23. Also visible are the depressions, slots, or holes 26 that engage with tabs or pins on the front of the housing. In some embodiments, the sides of the slot 21 comprise texture or tick marks 27 that are at a measured distance from one another down the length of the slot 21. The tick marks 27 minimally engage with the carrier of the blade and/or scraper as it advances, or retreats, along the length of the slot 21 to allow the practitioner to feel, or otherwise determine, how far the carrier has advanced along the slot. In some embodiments, the distal end 23 of the cannula 20 is blunted and serves as an obturator.

FIG. 11B shows a side view of the cannula 20, showing the proximate 22 and distal 23 ends, as well as the depressions, slots, or holes 26 that engage with tabs or pins on the front of the housing. In some embodiments, the distal end 23 of the cannula is angled upwards, as an obturator.

FIG. 11C depicts an angled view of the clear cannula 20 of the device. In some embodiments, the depressions, slots, or holes 26 that engage with tabs or pins on the front of the housing are located on the top and bottom of the proximate end 22 of the cannula. In some embodiments, rather than individual or multiple depressions, slots, or holes 26 on the top, bottom or sides of the cannula 20, the depression 26 may be an impression or groove that runs all the way around the outside of the proximate end 22 of the cannula 20 and engages with an annular ring that runs around the inside of the distal end of the housing.

FIG. 11D shows an end view of the cannula at the proximate end 22. The view shows the slot, which is contiguous with the central lumen 28 of the cannula. FIG. 11E is a cross-sectional view of the cannula 20 at bisecting line E-E in FIG. 11A, looking towards the proximate end of the cannula 20. The longitudinal slot 21 in the top surface of the cannula 20 can be seen to be contiguous with the central lumen of the cannula tube 20.

Figure 12D:
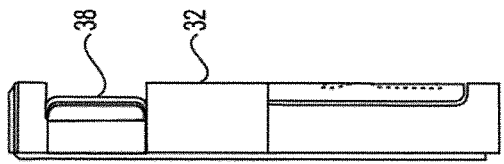
FIGS. 12A-F show perspective and cross-sectional views of the top shell of the housing of the embodiment depicted in FIG. 9.
Figure 12C:
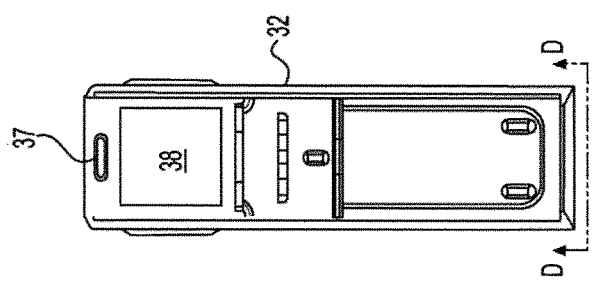
Figure 12F:
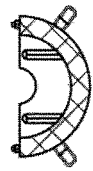
Figure 12B:
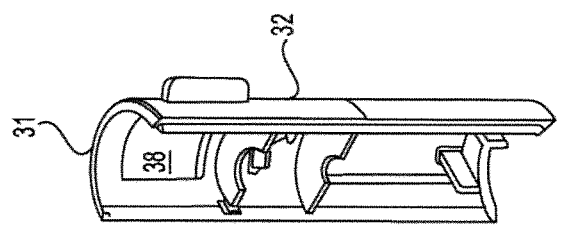
Figure 12E:
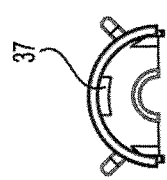
Figure 12A:
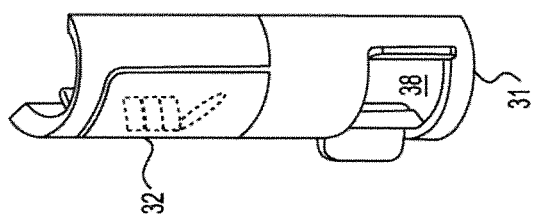

FIGS. 12A-F show various views of the top half 32 of the housing 30. FIG. 12A shows the outside of one embodiment of the top half 32 of the housing 30 at an angle, while FIG. 12B shows the inside of one embodiment of the top half 32 of the housing 30 at an angle. FIG. 12C shows the inside of one embodiment of the top half 32 of the housing 30, showing one embodiment of a tab or pin 37 that engages with a depression, slot, or hole located on the proximate end of the cannula shown in FIGS. 11A-E. In some embodiments, rather than individual or multiple tabs or pins at the distal end of the housing, the tab 37 may be an annular ring that runs around the inside of the distal end of the housing 30 and engages an impression or groove that runs all the way around the outside of the proximate end of the cannula. FIG. 12D shows the upper half 32 of the housing 30 from a side view, while FIG. 12E shows a view of the top half 32 of the housing 30 from the distal end and FIG. 12F shows a view of the top half 32 of the housing 30 from the proximate end.

Figure 13D:
FIGS. 13A-F show perspective and cross-sectional views of the bottom shell of the housing of the embodiment depicted in FIG. 9.
Figure 13C:
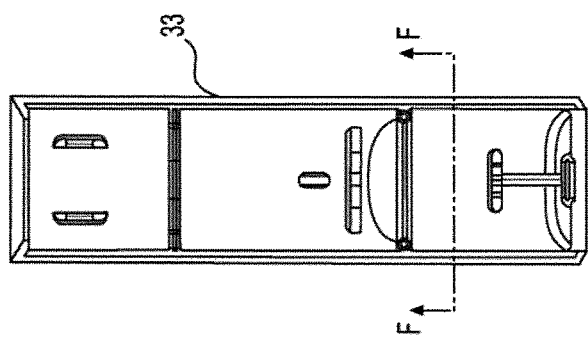
Figure 13F:
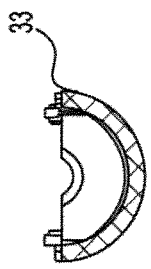
Figure 13B:
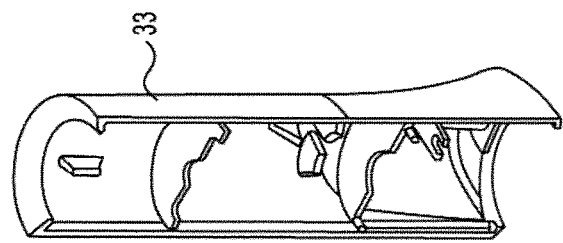
Figure 13E:
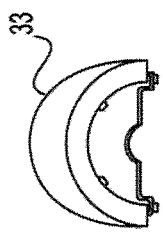
Figure 13A:
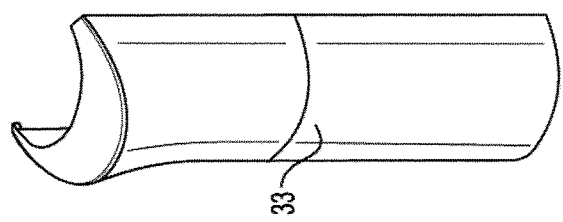

FIGS. 13A-F show various views of the lower half 33 of the housing 30. FIG. 13A shows the outside of one embodiment of the lower half 33 of the housing 30 at an angle, while FIG. 13B shows the inside of one embodiment of the lower half 33 of the housing 30 at an angle. FIG. 13C shows the inside of one embodiment of the lower half 33 of the housing 30. FIG. 13D shows the lower half 33 of the housing 30 from a side view, while FIG. 13E shows a view of the lower half 33 of the housing 30 from the distal end and FIG. 13F shows a cross-sectional view looking towards the distal end of the lower half 33 of the housing 30 from the line A-A bisecting FIG. 13C.

Figure 14C:
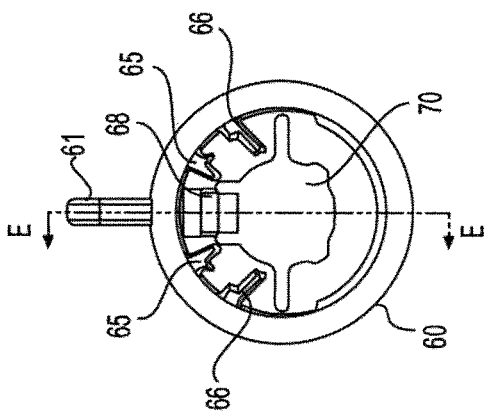
FIGS. 14A-E show perspective and cross-sectional views of the revolver element of the embodiment depicted in FIG. 9.
Figure 14B:
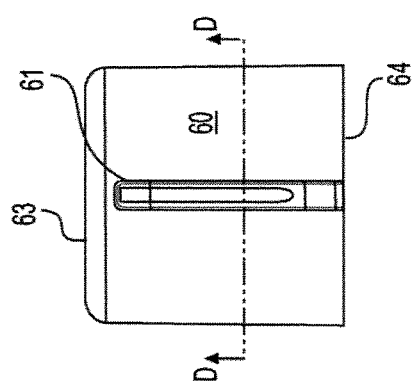
Figure 14A:
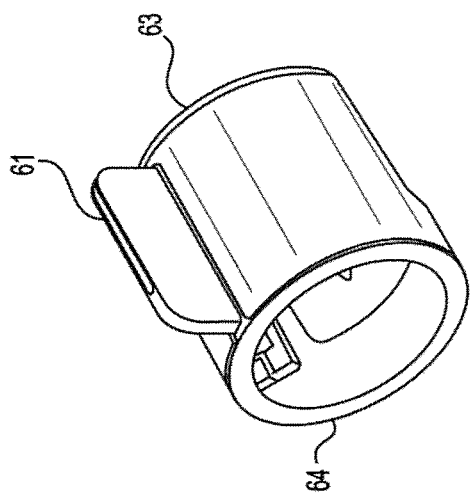

FIGS. 14A-E show detailed views of an embodiment of the revolver 60 element of the device. FIG. 14A is an exterior perspective view of the revolver 60, showing a selector switch 61 that protrudes through the opening 38 (FIG. 4) in the housing, as well as the proximate 63 and distal 64 ends of the revolver 60 element. The selector switch 61 is rotated from side to side by the user to select the appropriate instrument for a particular step in an endoscopic surgical procedure. FIG. 14B is a top view of the rotator 60 with the selector switch 61.

FIG. 14C is a view of the distal 64 end of the revolver 60. In some embodiments of the device, the revolver 60 comprises upper tabs 65 and lower tabs 66 that are used to select the scraper 90 or blade assembly 190 of the device. For example, when the selector switch 61 is rotated by the user to the position marked "SCRAPER" (see FIG. 3, for example), the tabs 65 and 66 engage the scraper 90 and move it to the centerline (here, line E-E in FIG. 14C) of the device. There, the scraper 90 is engaged by a tab on the tube (71 in FIG. 4, for example) of the device, so that it can be deployed into the cannula 20 (FIG. 4) and protrude through the longitudinal slot 21 (FIG. 4) therein. When the selector switch 61 is rotated by the user to the position marked "BLADE" (see FIG. 2, for example), the tabs 65 and 66 engage the blade assembly 190 and move it to the centerline (here, line E-E in FIG. 14C) of the device. There, the blade assembly 190 is engaged by a tab on the tube (71 in FIG. 4, for example) of the device, so that it can be deployed into the cannula 20 (FIG. 4) and protrude through the longitudinal slot 21 (FIG. 4) therein. However, when the selector switch 61 is rotated by the user to the position marked "SCOPE" (see FIG. 2, for example), the tabs 65 and 66 retain the scraper 90 and blade assembly 190 in their parked positions out of the centerline so that an endoscope, or other device, can be advanced through the tube 71 (FIG. 4) into the cannula without either the scraper tool or blade assembly being advanced.

Figure 14E:
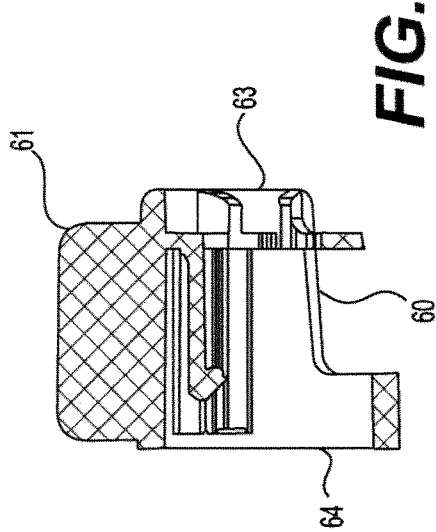
Figure 14D:
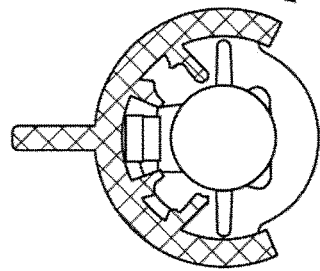

FIG. 14D is a cross-sectional view of revolver 60 at line B-B in FIG. 14B and looking in the direction of the proximate end 63 of the revolver 60. FIG. 14E is also a cross-sectional view of the revolver 60, this time along centerline A-A of FIG. 14C. As can be seen in this view, in some embodiments of the device, the revolver 60 comprises a hooked tab 68 that engages the front of the tab 79 that separates the notches (72, 73 in FIG. 10) in the slide lock 70 (see FIG. 15) that hold the scraper 90 and blade assembly 190. When the selector switch 61 is in the "SCOPE" position, for example, the hooked tab 68 helps ensure that neither the scraper tool nor blade assembly can be deployed into the cannula.

Turning to FIGS. 15A-E, shown is an embodiment of a slide lock 70 of the device. FIG. 15A shows the slide lock 70 from an angled perspective. The slide lock 70 comprises two notches 72,73 that hold the scraper 90 and blade assembly 190 in place when they are parked, as well as rotate them into the ready position when they are selected for use by rotation of the revolver 60 (FIGS. 14A-E, for example). The two notches 72,73 are separated from one another by the tab 79. The front of the tab 79 engages with the hooked tab 68 (FIG. 14E, for example) of the revolver 60 when the selector switch 61 is not lined up with the "SCRAPER" or "BLADE" options, thus preventing the scraper 90 or blade assembly 190 from being deployed into the cannula when not in use. In some embodiments, the slide lock 70 comprises retaining tabs 171,172 that hold a rotary clip 170 (FIGS. 16A-E, for example) in place, preventing the rotary clip from sliding forward or backward on the slide lock 70. The rotary clip 170 does not rotate with the revolver 60 and slide lock 70, serving to prevent the scraper 90 or blade assembly 190 from sliding forward out of their notches 72,73 when they are not selected. Some embodiments of the slide lock 70 further comprise a pair of wings 174,175 that engage with the revolver 60 (FIGS. 14A-E, for example) for turning the slide lock 70 when a particular tool, such as "SCRAPER," "BLADE" or "SCOPE" is selected. Some embodiments of the slide lock 70 further comprise a disc 176 at the proximate end. The outer rim of the disc 176 contacts the inside surface of the housing 30 (FIG. 10) to allow the slide lock 70 to rotate, but prevents or constrains side-to-side or up-down movement of the slide lock in the device.

Still referring to FIG. 15, FIG. 15B is a side view of the slide lock 70. In some embodiments, the retaining tabs 171,172 are matched by identical or similar retaining tabs on the other side of the slide lock 70. FIG. 15C shows an end view of slide lock 70, looking from the distal end towards the disc 176 at the proximate end. The center lumen 173 of the slide lock 70 allows the passage of the tube assembly 71 through the slide lock 70 and into the cannula 20 (FIG. 10). FIG. 15D is a perspective view of the slide lock 70 from the top, while FIG. 15E is a longitudinal cross-section view at line E-E through FIG. 15D.

Turning now to FIGS. 16A-E, perspective views of an embodiment of a rotary clip 170 of the device are presented. FIG. 16A shows the rotary clip 170 from an angle. In some embodiments, the rotary clip 170 comprises a tab 177 that engages with the inside of the housing 30 (FIG. 10) to prevent the rotary clip 170 from rotating or sliding. The top of the rotary clip 170 is open 178, so that when the scraper tool or blade assembly is rotated into the deployment position, it can be deployed through the rotary clip 170 and into the cannula 20 (FIG. 10). FIG. 16B is a perspective view of the rotary clip 170 as viewed from the distal side towards the proximate side. FIG. 16C is a side perspective view of the rotary clip 170. In some embodiments, a portion of the distal side of the rotary clip 170 may be notched 179. FIG. 16D is a perspective view of the rotary clip 170 looking down upon the top. The rotary clip may be manufactured from any suitable material, such as plastic, stainless steel, aluminum, or metal alloys. In some embodiments, the rotary clip 170 may be formed, cut, stamped, cast or milled as a flat piece, as shown in FIG. 16E, from a malleable metal such as SS 303 and then formed into the final shape of being an open-topped ring with a tab at the bottom as shown in FIG. 16A. In other embodiments, the rotary clip 170 may be formed, cut, molded, 3D-printed, cast or milled from a suitable material as an open-topped ring with a tab at the bottom as shown in FIG. 16A.

FIGS. 17A-D show an embodiment of a tube assembly 71 of the device. In some embodiments, the tube assembly is composed of stainless steel, preferably AISI 304 stainless steel. However, the tube assembly can be made from any suitable material including, but not limited to, aluminum, titanium, nitinol or other metal alloys, or plastic. In some embodiments where the tube assembly 71 is made of plastic, the plastic may be clear, allowing visualization with an endoscope of tissues surrounding the cannula 20 through the body of the tube assembly 71.

FIG. 17A is a top view of the tube assembly 71. The body of the tube assembly 71 slides through the center lumen 173 of the slide lock 70. The tube assembly 71 comprises near its distal end a tool selector 78. The tool selector 78 is directly on top of the tube assembly 71. With reference to FIGS. 9 and 10, when the selector switch 61 of the revolver 60 is positioned at the "SCOPE" setting, no tools are engaged with the tool selector 78 and the tube assembly 71 can be advanced into the cannula 20 without the blade assembly 190 or scraper 90. When the selector switch 61 of the revolver 60 is mover to the "BLADE" setting, the revolver 60 rotates the slide lock 70 such that the notch 72 holding the blade assembly 190 is moved to the top of the tube assembly 71 and the notch in the bottom surface of the blade assembly 190 is positively engaged with the tool selector 78. Advancement of the tube assembly 71 would cause the advancement of the blade assembly 190 into and down the length of the cannula 20, protruding through the slot 21. When the selector switch 61 of the revolver 60 is mover to the "SCRAPER" setting, the revolver 60 rotates the slide lock 70 such that the notch 73 holding the scraper 90 is moved to the top of the tube assembly 71 and the notch in the bottom surface of the scraper 90 is positively engaged with the tool selector 78. Advancement of the tube assembly 71 would cause the advancement of the scraper 90 into and down the length of the cannula 20, protruding through the slot 21. In some embodiments, the tool selector 78 is welded, preferably laser welded, onto the top of the tube element of the tube assembly 71. In a preferred embodiment, the tool selector 78 is welded all around at its base to the tube element. In particular embodiments, the strength of the weld should be able to withstand the application of 5 in-lbs torque to the unit, more particularly 10 in-lbs torque. The tube assembly 71 further comprises a tube stop 84 at the proximate end of the tube element. The tube stop 84 retains the tube assembly 71 in the housing 30 of the device, preventing the tube assembly from passing completely through the stabilizer disc 74 (FIG. 10) at the proximate end of the housing 30. In some embodiments, the tube stop 84 is welded flush with the proximate end of the tube element of the tube assembly. In particular embodiments, the weld should be strong enough to withstand at least 10 lbs normal force to the face, more particularly 20 lbs normal to the face. In some embodiments, the proximate portion of the tube assembly.

The tube assembly 71 can optionally be marked on the top or side surface with gradations 86,87 as exemplified in FIG. 17A to show the distance that the tube assembly 71 has been advanced into the cannula 20. As a non-limiting example, major gradations 86 can be made to show each centimeter in distance that the tube assembly 71 has been advanced into the cannula 20, with minor gradations 87 between them to show, for example, each 1, 2, 2.5 or 5 millimeters. While the gradations can be applied to the tube assembly 71 by any means known in the art, it is preferable to lasermark the gradations on the tube assembly 71 for accuracy and permanence. In some embodiments, the distance between the major or minor gradations 86,87 corresponds to the distance between the tick marks 27 (FIG. 11A) in the sides of the slot 21 in the cannula 20.

FIG. 17 B shows a cross-section of the tube assembly 71 at the line bisecting FIG. 17A at A-A and looking in the direction of the tube stop 84 at the proximate end. The tube assembly 71 has a central lumen 85 that accommodates the insertion and free passage of an endoscope or other viewing device or tool, for example. FIG. 17C is a side view of the tube assembly 71 and FIG. 17 D is a perspective view of the tube assembly 71 from an angle.

FIGS. 18A-C show an embodiment of the blade assembly 190, comprising a pusher base 191 and a cutting blade 200. The blade assembly 190 is compatible with the embodiment of the device shown in FIGS. 9-10, as well as with the embodiment of the device shown in FIG. 27. FIG. 18A is a side perspective view of the blade assembly 190. The pusher base 191 comprises a notch 192 that positively engages with the tool selector 78 of the tube assembly (FIGS. 17A, C and D). When the selector switch 61 of the revolver 60 (FIG. 10) is rotated to the "BLADE" position, the blade assembly 190 is rotated upward by the slide lock 70 so that the notch 192 in the base of the blade assembly 190 slides onto and engages the tool selector 78. The tool selector 78 then firmly holds the blade assembly 190 on the surface of the tube assembly 71. Advancing the tube assembly 71 also advances the blade assembly 190 into the cannula 20 (FIG. 10). The blade assembly 190 protrudes through the longitudinal slot 21 in the cannula 20 and advancement of the blade assembly 190 with the tube assembly 71 moves the blade 200 into contact with the target tissue. Further advancement of the blade assembly allows the blade 200 to separate the target tissue. In preferable embodiments, the bottom surface 210 of the blade 200 is at least slightly above the bottom surface 193 of the pusher base 191 so that the blade 200 does not directly contact the body of the tube assembly 71, which may affect rotation of the blade assembly 190 into place for deployment. In particular embodiments, the end of the pusher base opposite the blade 200 is angled so that it does not catch tissues as it is being withdrawn through the slot 21 of the cannula 20. FIG. 18B is an end view of the blade assembly 190. The width of the pusher base 191 is such that it securely contacts the side walls of the slot 21 in the cannula 20 (FIG. 10) but is still able to be advanced or withdrawn through the slot without an amount of friction that would impede its progress. The sides of the blade 200 do not contact the walls of the slot 21. In particular embodiments, the bottom surface 193 of the pusher base is curved to match the curvature of the tube assembly, thus inhibiting or preventing side to side motion, or wobble, of the blade assembly 190 during deployment. FIG. 18C is an angled perspective view of the blade assembly 190. The view is clear so that the attachment of the blade 200 to the pusher base 191 can be seen. In particular embodiments, the blade 200 comprises a tab 215 that embeds into the pusher base 191. In particular embodiments there is a hole 220 in the tab 215 that allows the material of the pusher base 191 to flow through it when the pusher base 191 is cast, thereby securing the tab 215 into the pusher base 191. In some embodiments, the tab 215 is secured into the pusher base 191 using a pin or screw. In such an embodiment, the blade 200 may be replaceable in the blade assembly, allowing the use of blades with different profiles particularly suited for a specific surgical procedure. For example, it may be desirable to use a hook blade in some situations, where the cutting surface faces back towards the housing 30 of the device, allowing the practitioner to move the blade past the target tissue and separate the target tissue by pulling the blade backwards, rather than separating the target tissue upon advancing the blade. The pusher base 191 of the blade assembly 190 can be formed of any medically acceptable material, such as a plastic, as it does come in contact with body tissues. In a particular embodiment, the pusher base 191 is formed of polycarbonate. In some embodiments, the blade assembly 190 may be replaced in the device with any other suitable blade tool that engages with the tool selector, such as, but not limited to, the blade 80 shown in FIG. 4 or a hooked endoscopic blade tool.

Figure 19C:
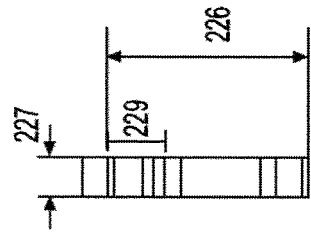
FIGS. 19A-E show perspective and cross-sectional views of the blade of FIGS. 18A-C.
Figure 19B:
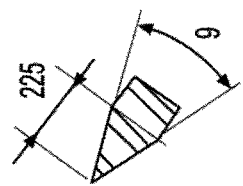
Figure 19E:
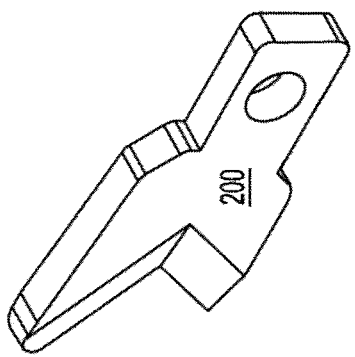
Figure 19A:
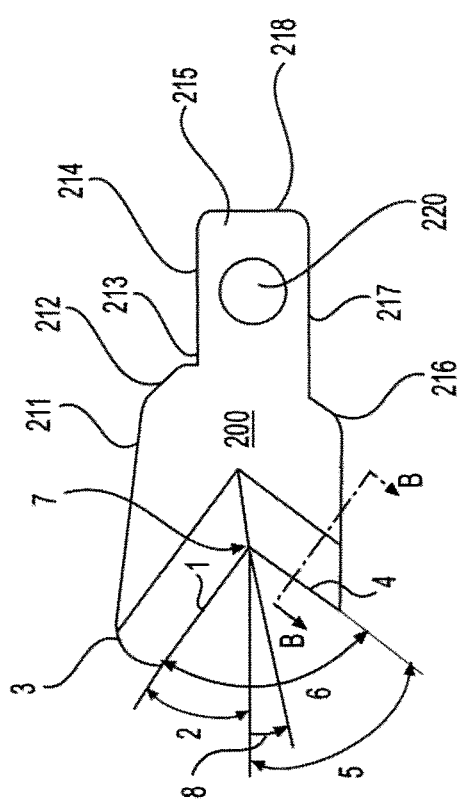

FIGS. 19A-E show a particular embodiment of the blade 200. FIG. 19A shows a side view of the blade 200 embodiment. In a particular embodiment, the blade 200 as shown in FIG. 19A comprises an upper cutting surface 1 on the leading end of the blade, which is at an angle 2 with respect to the horizontal orientation of the blade 200, as defined by the bottom surface 210 of the blade 200. The angle 2 is such that the top of cutting surface 1 is forward of the bottom of the cutting surface. In one embodiment the angle 2 is between about 30 and about 45 degrees. In a particular embodiment, the angle 2 is between about 30 and about 40 degrees. In another particular embodiment, the angle 2 is between about 33 and about 39 degrees. In a more particular embodiment, the angle 2 is about 36 degrees.

In some embodiments, the upper end 3 of the cutting surface 1 is radiused. The radiused upper end 3 of the cutting surface 1 is about 90 degrees of a circle and has a radius measurement between about 0.50 mm and 1.50 mm. In a particular embodiment, the radius is about 0.94 mm.

In a particular embodiment, the blade 200 as shown in FIG. 19A comprises a lower cutting surface 4 on the leading end of the blade, which is at an angle 5 with respect to the horizontal orientation of the blade 200, as defined by the bottom surface 210 of the blade 200. The angle 5 is such that the bottom of the lower cutting surface 4 is forward of the top of the lower cutting surface. In one embodiment the angle 5 is between about 45 and about 65 degrees. In a particular embodiment, the angle 5 is between about 50 and about 60 degrees. In a more particular embodiment, the angle 5 is about 54 degrees. In some embodiments, the bottom of the lower cutting surface 4 is not radiused, as the bottom of the lower cutting surface 4 remains within the slot 21 of the cannula 20 (FIG. 10) during deployment.

In a particular embodiment, the blade 200 as shown in FIG. 19A comprises upper cutting surface 1 and lower cutting surface 4 on the leading end of the blade 200, which are at an angle 6 to one another and meet at a central crotch 7. In one embodiment the angle 6 is between about 80 and about 100 degrees. In a further embodiment, the angle 6 is between about 85 and about 95 degrees. In a still further embodiment, the angle 6 is about 90 degrees.

Still referring to FIG. 19A, in some embodiments, the plane where the upper and lower cutting surfaces meet is angled downward 8 towards the crotch 7. In some embodiments, the angle 8, as it relates to the plane defined by the bottom surface 210 of the blade, is between about 0 and 20 degrees. In further embodiments, the angle 8, as it relates to the plane defined by the bottom surface 210 of the blade, is between about 5 and 15 degrees. In a particular embodiment, the angle 8, as it relates to the plane defined by the bottom surface 210 of the blade, is about 9 degrees. In particular embodiments, the crotch 7 is ground to have a maximum radius of between about 0.18 mm and about 0.58 mm, more particularly between about 0.28 mm and about 0.48 mm. In a still more particular embodiment, the crotch 7 is ground to have a maximum radius of about 0.381 mm.

In some embodiments, in order to prevent the blade 200 from catching on tissues when the blade 200 is drawn backwards through the cannula 20, the top surface 211 of the blade 200 is angled downward and may comprise a further stepped angle 212, before fully descending 213 to meet the top edge 214 of the tab 215 that secures the blade 200 into the pusher base 191. In a particular embodiment, the vertical height of the radius 3 at the top end of the upper cutting surface 1 above the top edge 214 of the tab 215 is between about 0.75 mm and about 1.75 mm, more particularly between about 1.0 mm and about 1.50 mm. In a more particular embodiment, the vertical height 229 of the radius 3 at the top end of the upper cutting surface 1 above the top edge 214 of the tab 215 is about 1.26 mm.

Additionally, in some embodiments, the trailing end 216 of the bottom surface 210 of the blade 200 may be angled up to the bottom edge 217 of the tab 215. In a particular embodiment, the vertical height between the bottom surface 210 of the blade 200 and the bottom edge 217 of the tab 215 is between about 0.1 mm and about 1.0 mm, more particularly between about 0.3 mm and about 0.7 mm. In a more particular embodiment, the vertical height between the bottom surface 210 of the blade 200 and the bottom edge 217 of the tab 215 is about 0.5 mm.

Still referring to FIG. 19A, in some embodiments, the tab 215 is between about 1.5 mm and about 2.0 mm high between the top edge 214 and bottom edge 217 of the tab 215, more particularly between about 1.65 mm and about 1.85 mm. In a still more particular embodiment, the tab 215 is about 1.75 mm high between the top edge 214 and bottom edge 217 of the tab 215. Additionally, in some embodiments, the tab 215 is between about 2.0 mm and about 3.0 mm long between where it meets the top surface 211 of the blade 200 (at 213) and the trailing edge 218 of the tab 215, more particularly between about 2.25 mm and about 2.75 mm. In a still more particular embodiment, the tab 215 is about 2.5 mm long between where it meets the top surface 211 of the blade 200 (at 213) and the trailing edge 218 of the tab 215. The hole 220 in the tab 215 that serves to secure the blade 200 into the pusher base 191 (FIG. 18C) is generally centered horizontally and vertically in the tab 215 in order to provide maximum adhesion of the tab 215 to, and stability within, the pusher base 191. The diameter of the hole 220 is between about 0.5 mm and about 1.5 mm, more particularly between about 0.75 mm and about 1.25 mm. In a more particular embodiment, the diameter of the hole 220 is about 1.0 mm.

In some embodiments, the crotch 7 of the blade 200 is between about 3.0 mm and about 7.5 mm forward of the trailing edge 218 of the tab 215, more particularly between about 4.0 mm and about 6.5 mm. In a still more particular embodiment, the crotch 7 of the blade 200 is about 5.25 mm forward of the trailing edge 218 of the tab 215.

In particular embodiments, the blade 200 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODI-FIED 440-A stainless steel. The blade is optionally flash electropolished or passivated per ASTM A967, or by any other method that delivers a similar finish. The cutting edges are machine finished and must be sharp. In a particular embodiment, the steel of the blade is heat-treated to Rockwell C hardness of about 50-72. In a more particular embodiment, the steel of the blade is heat-treated to R30N 75.7-77.5 (Rockwell C hardness of 58-60).

Referring now to FIG. 19B, the lower cutting surface 4 is a single beveled cutting surface and the angle 9 is between about 30 degrees and about 50 degrees. In some embodiments, the angle 9 is between about 35 degrees and about 45 degrees. In a particular embodiment, the angle 9 is about 40 degrees. While not shown in the figure, the upper cutting surface 1 is a similarly a single beveled cutting surface and the angle is between about 30 degrees and about 50 degrees. In some embodiments, the angle is between about 35 degrees and about 45 degrees. In a particular embodiment, the angle is about 40 degrees.

Also referring to FIG. 19B, in some embodiments, the depth of the grind 225 of lower cutting surface 4, as well as for upper cutting surface 1, is between about 0.6 mm and about 1.1 mm. In other embodiment, the depth of the grind 225 is between about 0.7 mm and about 1.0 mm. In a further embodiment, the depth of the grind 225 is about 0.86 mm.

Referring now to FIG. 19C, in a particular embodiment, the overall height 226 of the body of the blade 200 is between about 3.0 mm and about 4.0 mm. In another embodiment, the height 226 of the body of the blade 200 is between about 3.25 mm and about 3.75 mm. In a more particular embodiment, the height 226 of the body of the blade 200 is about 3.5 mm. Again referring to FIG. 1C, in a particular embodiment, the width 227 of the body of the blade 200 is between about 0.3 mm and about 0.9 mm. In another embodiment, the width 227 of the body of the blade 200 is between about 0.45 mm and about 0.75 mm. In a particular embodiment, the width 227 the body of the blade 200 is about 0.635+/−0.025 mm.

Figure 19D:
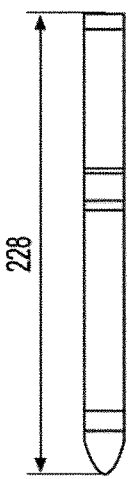

Referring to FIG. 19D, the total length 228 of the blade 200 from the leading point of the upper cutting surface 1 to the trailing end 218 of the tab 215 is between about 4 mm and about 10 mm. In another particular embodiment, the total length 228 of the blade 200 from the leading point of the upper cutting surface 1 to the trailing end 218 of the tab 215 is between about 5.5 mm and about 8.5 mm. In a more particular embodiment the total length 228 of the blade 200 is about 7.153 mm. FIG. 19E presents an angled perspective view of an embodiment of the blade 200.

Figure 20:
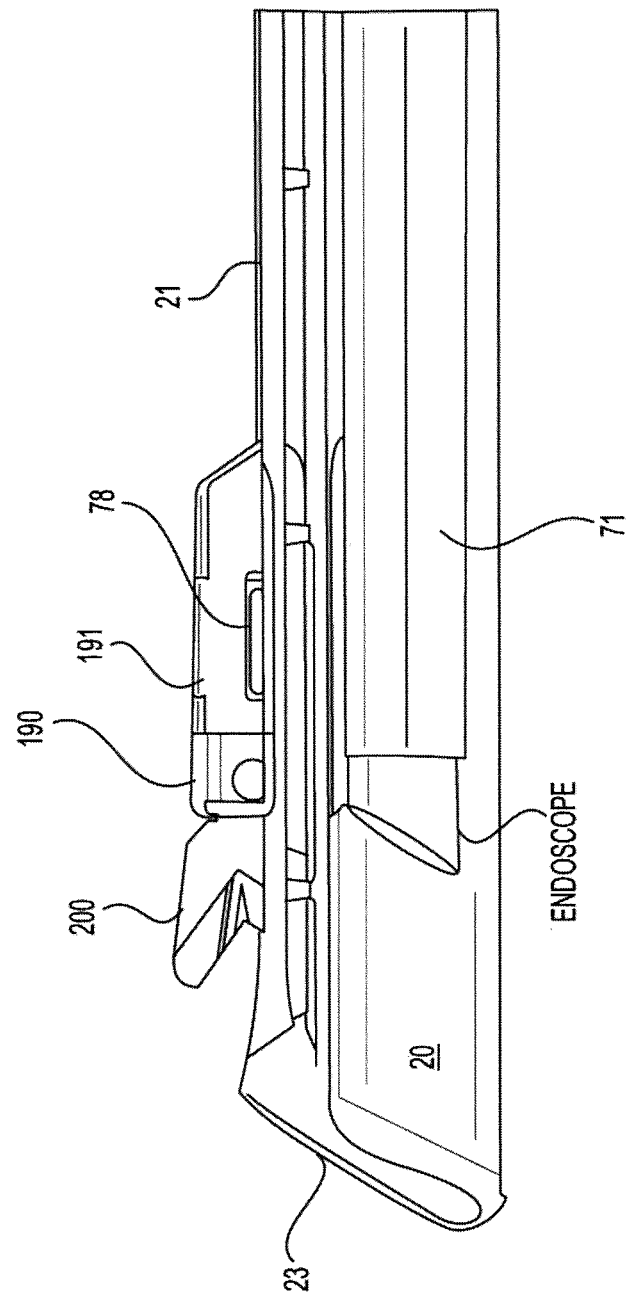
FIG. 20 shows a perspective view of the blade element of the embodiment depicted in FIG. 9, as deployed through the slot in the cannula.
Figure 21:
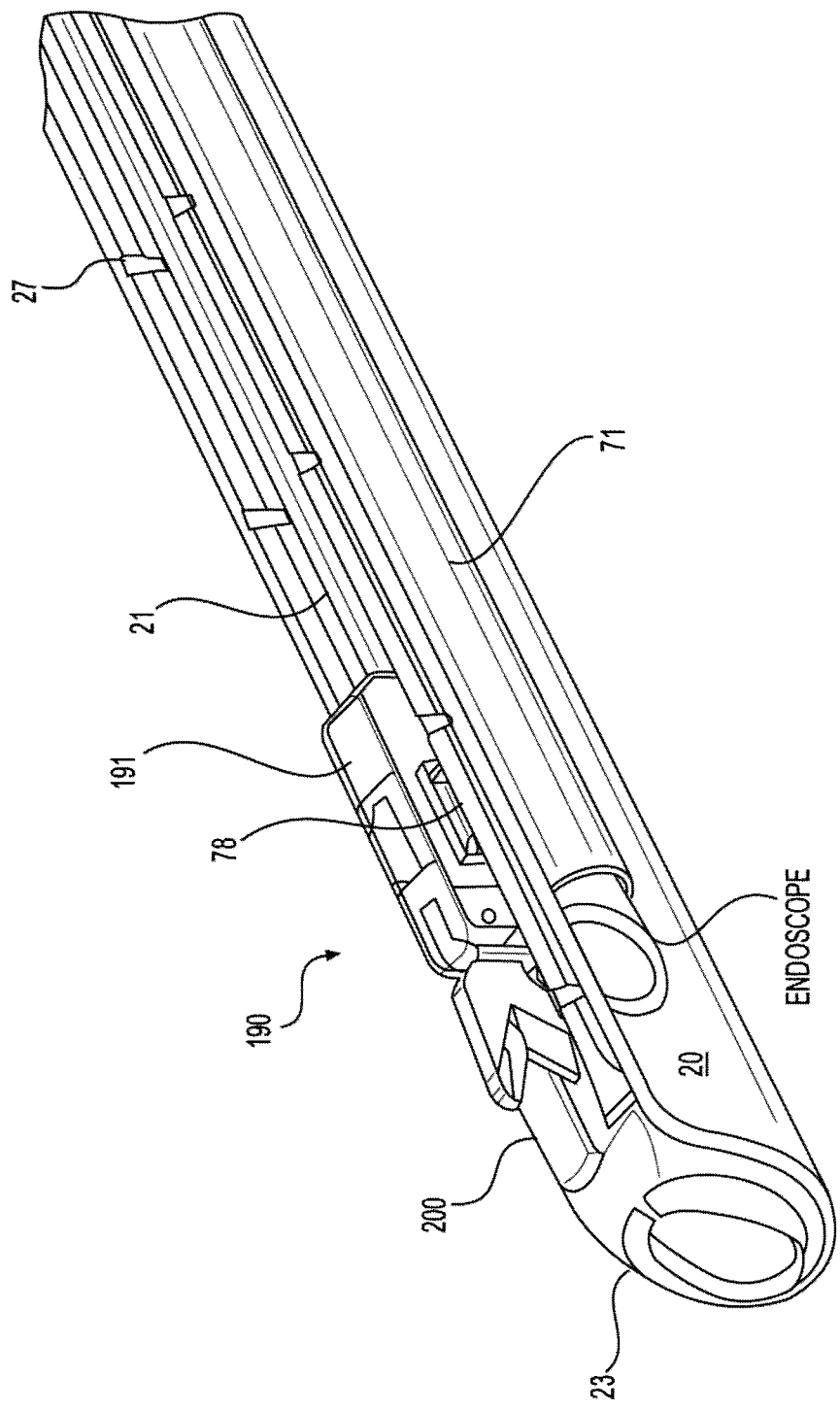
FIG. 21 shows another perspective view of the blade element of the embodiment depicted in FIG. 9, as deployed through the slot in the cannula.

FIGS. 20 and 21 show perspective views of the blade assembly 190 deployed into the cannula 20 of the device. Tube assembly 71 can be seen within the lumen of the cannula 20 with an endoscope extended through the tube assembly 71. The tool selector 78 is positively engaged with the pusher base 191 of the blade assembly 190. The pusher base 191 and blade 200 are seen partially protruding from the slot 21 in the cannula 20, but are securely held in the slot 21 by the tool selector 78 of the tube assembly 71.

Figure 22:
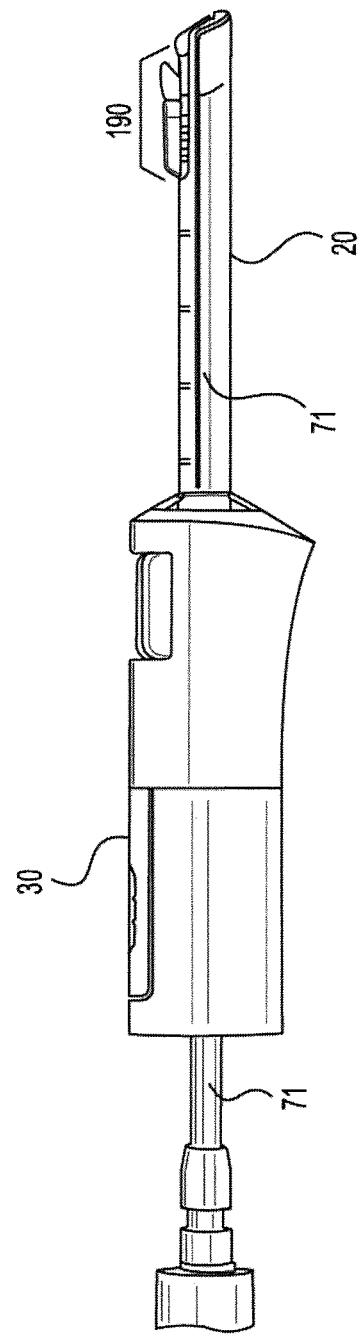
FIG. 22 shows a side perspective view of the embodiment depicted in FIG. 9 with the blade deployed through the slot in the cannula.

FIG. 22 is another perspective view showing the assembled compact endoscopic surgical device of FIG. 9 with the blade assembly 190 deployed.

FIGS. 23A-E show an embodiment of the scraper 90 of the compact endoscopic surgical device. As seen in FIG. 23A, the base 91 of the scraper 90 comprises a notch 92 that positively engages with the tool selector 78 of the tube assembly (FIGS. 17A, C and D). When the selector switch 61 of the revolver 60 (FIG. 10) is rotated to the "SCRAPER" position, the scraper 90 is rotated upward by the slide lock 70 so that the notch 92 in the base 91 of the scraper 90 slides onto and engages the tool selector 78. The tool selector 78 then firmly holds the scraper 90 on the surface of the tube assembly 71. Advancing the tube assembly 71 also advances the scraper 90 into the cannula 20 (FIG. 10). The teeth 93 of the scraper 90 protrude through the longitudinal slot 21 in the cannula 20 and advancement of the scraper 90 with the tube assembly 71 moves the teeth 93 into contact with the target tissue. Further advancement of the blade assembly allows the teeth 93 to rake across the target tissue. In particular embodiments, the distal end 94 and proximate end 95 of the base 91 are rounded and angled downwards so that they do not catch tissues as the scraper 90 is being advanced or withdrawn through the slot 21 of the cannula 20.

FIG. 23B is an end view of the scraper tool 90. The width of the base 91 is such that it securely contacts the side walls of the slot 21 in the cannula 20 (FIG. 10) but is still able to be advanced or withdrawn through the slot without an amount of friction that would impede its progress. In particular embodiments, the bottom surface of the base 91 is curved to match the curvature of the tube assembly, thus inhibiting or preventing side to side motion, or wobble, of the scraper 90 during deployment.

FIG. 23C is a perspective view of the top of the scraper 90 showing the linear arrangement of the teeth 93. FIG. 23D is a cross-sectional view of the scraper 90 at the line D-D through FIG. 23C. In some embodiments, the teeth are angled 96 to each other at between about 45 degrees and 75 degrees, more particularly between about 55 degrees and about 65 degrees. In a still more particular embodiment, the teeth 93 are angled 96 to each other at about 60 degrees. In some embodiments the teeth 93 are between about 1.0 mm and about 6.0 mm in height, more particularly between about 2.0 mm and about 4.0 mm. In a still more particular embodiment, the teeth 93 are about 3.23 mm in height. FIG. 23E is a perspective view of the scraper 90 from an angle. The scraper 90 can be formed of any medically acceptable material, such as a plastic, ceramic, stainless steel, or nitinol, as it does come in contact with body tissues. In a particular embodiment, scraper 90 is formed of polycarbonate.

Figure 24:
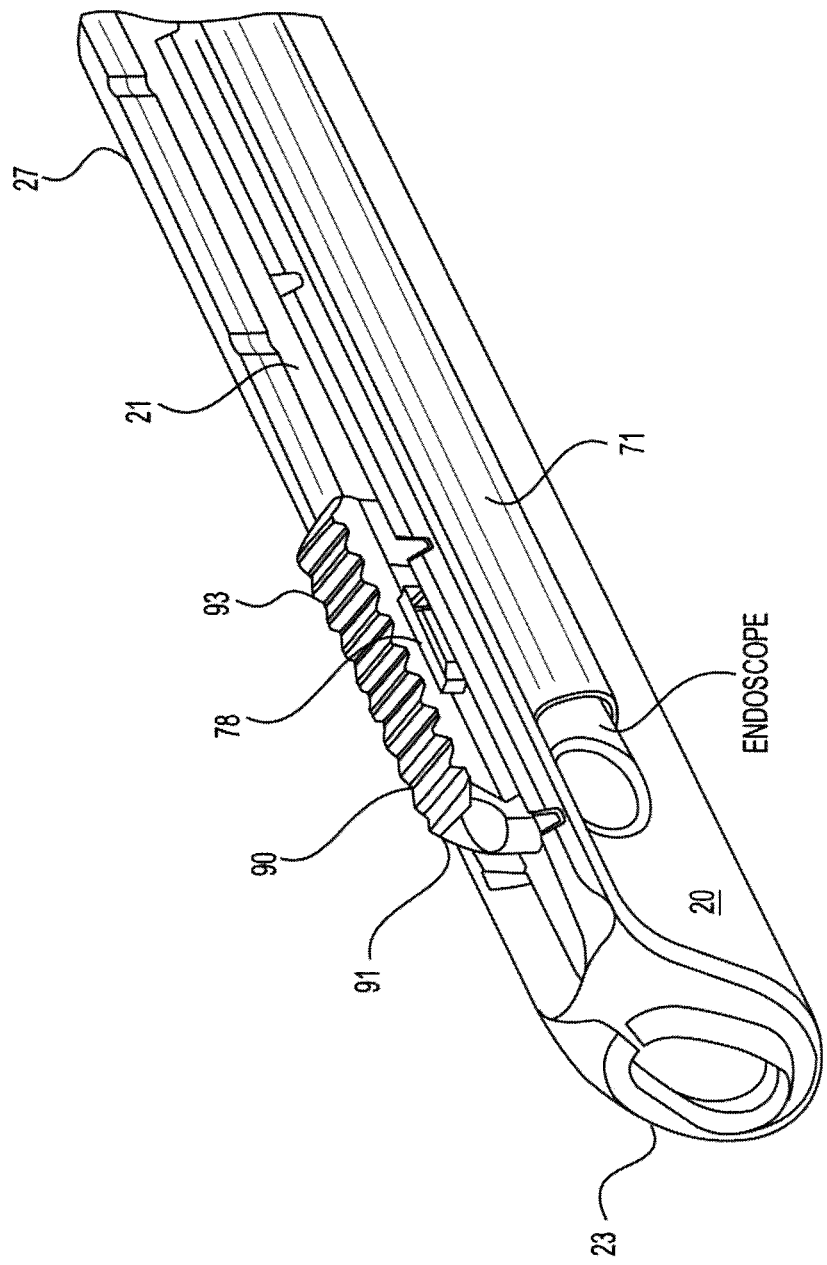
FIG. 24 shows a perspective view of the scraper element of the embodiment depicted in FIG. 9, as deployed through the slot in the cannula.

FIG. 24 shows a perspective views of the scraper 90 deployed into the cannula 20 of the device. Tube assembly 71 can be seen within the lumen of the cannula 20 with an endoscope extended through the tube assembly 71. The tool selector 78 is positively engaged with the scraper 90. The base 91 of the scraper 90 is seen partially protruding from the slot 21 in the cannula 20, but is securely held in the slot 21 by the tool selector 78 of the tube assembly 71. The teeth 93 are fully exposed to the environment outside the cannula 20 when deployed.

Figure 25:
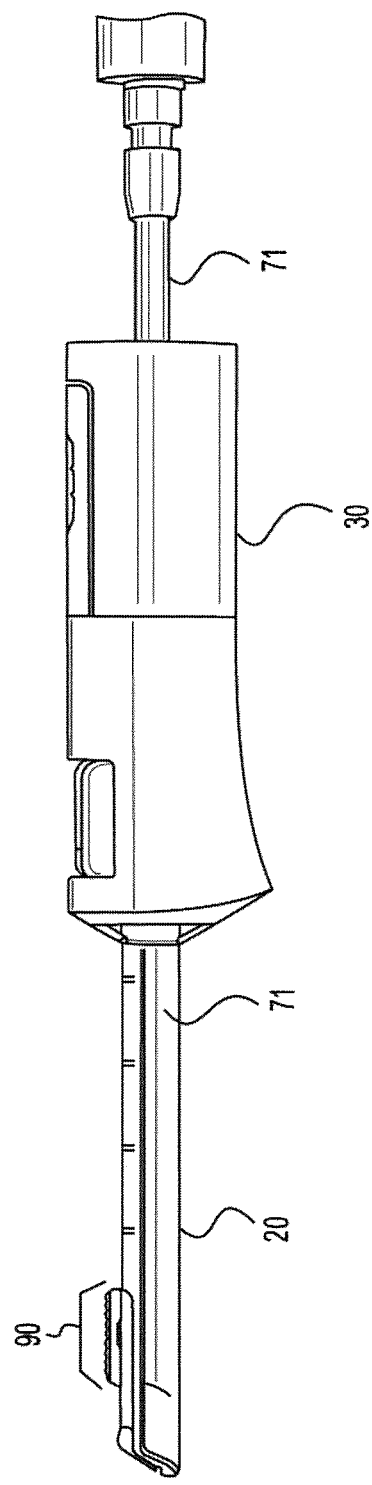
FIG. 25 shows a side perspective view of the embodiment depicted in FIG. 9 with the scraper deployed through the slot in the cannula.

FIG. 25 is a side perspective view showing the assembled compact endoscopic surgical device of FIG. 9 with the scraper 90 deployed.

Figure 26:
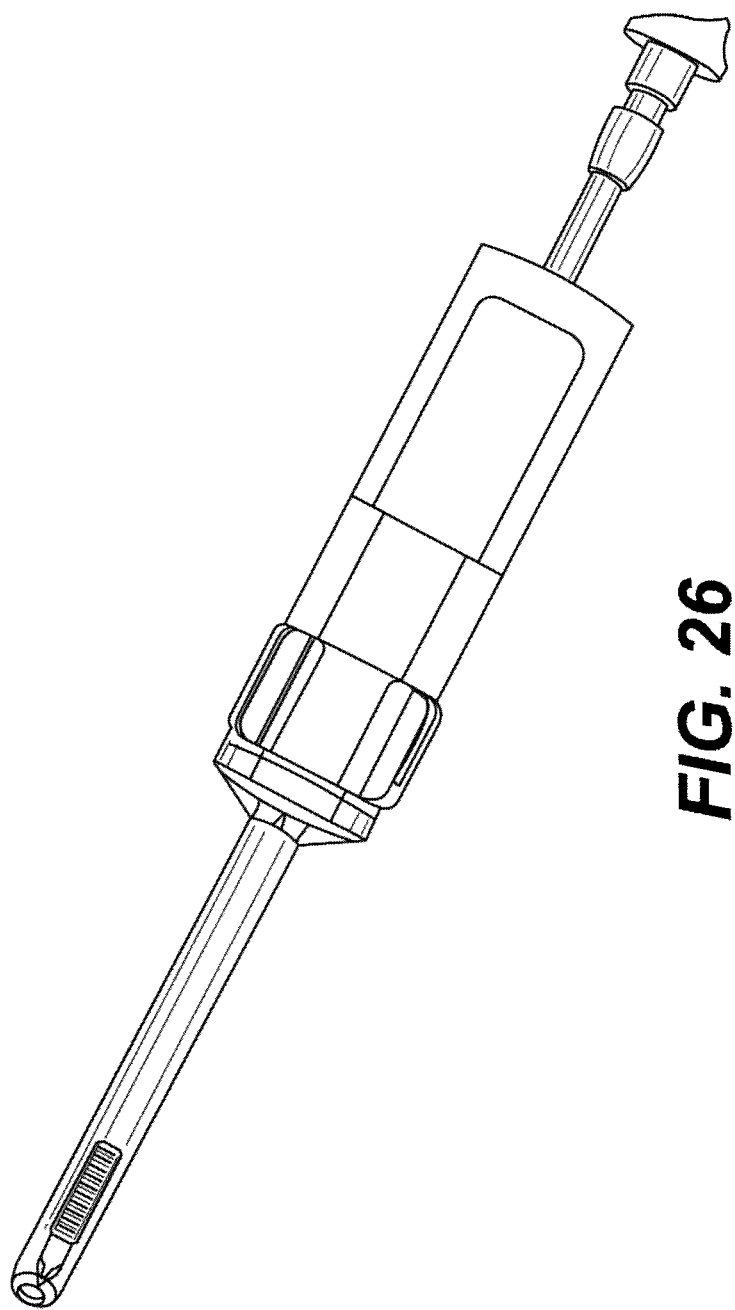
FIG. 26 shows a top perspective view of the embodiment depicted in FIG. 9 with the scraper deployed through the slot in the cannula.

FIG. 26 is a top perspective view showing the assembled compact endoscopic surgical device of FIG. 9 with the scraper 90 deployed.

Rotationally Operated Devices with Scope Lock Assembly

Figure 27:
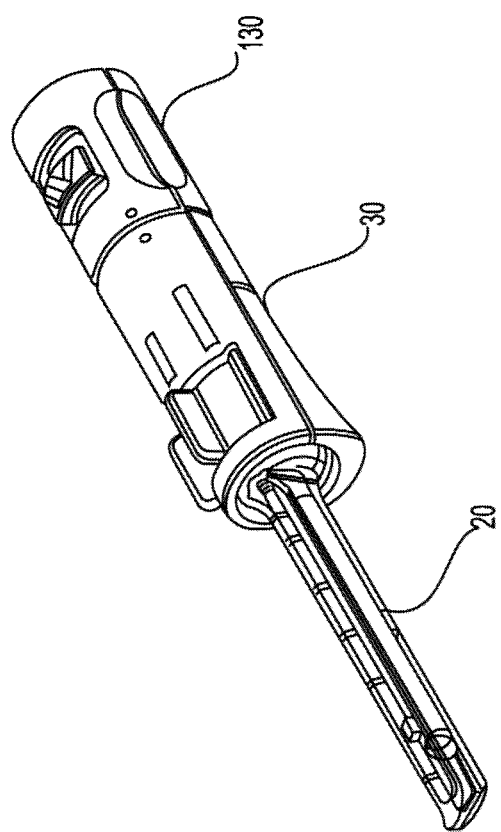
FIG. 27 is a perspective view of another embodiment of the device of the present application, comprising a scope lock component.

FIGS. 27 and 28A-D show embodiments of the present device wherein the device comprises a rotational switch for selecting the tool to advance into the cannula, as well as a latch for locking an endoscope in position during a procedure. FIG. 27 shows a view of the device depicting the cannula 20, the main housing 30 holding the rotational tool selector and storage for the tools, and the scope lock assembly 30A. As described in more detail below, the scope lock assembly 30A comprises a scope lock housing 130 having a top shell 132 (FIGS. 36A-F) and a bottom shell 133 (FIGS. 37A-F) and a scope lock piece 150 (FIGS. 47A-E).

FIG. 28A shows a view of the device depicted in FIG. 27, wherein the tube assembly 71 can be seen extended into the cannula 20. The selector switch 61 is set for "SCOPE" and neither the blade tool nor the scraper is attached to the tool selector 78. FIG. 28B shows a top view of the device and FIG. 28C shows a side view. FIG. 28D is a distal end view of the device.

Figure 29:
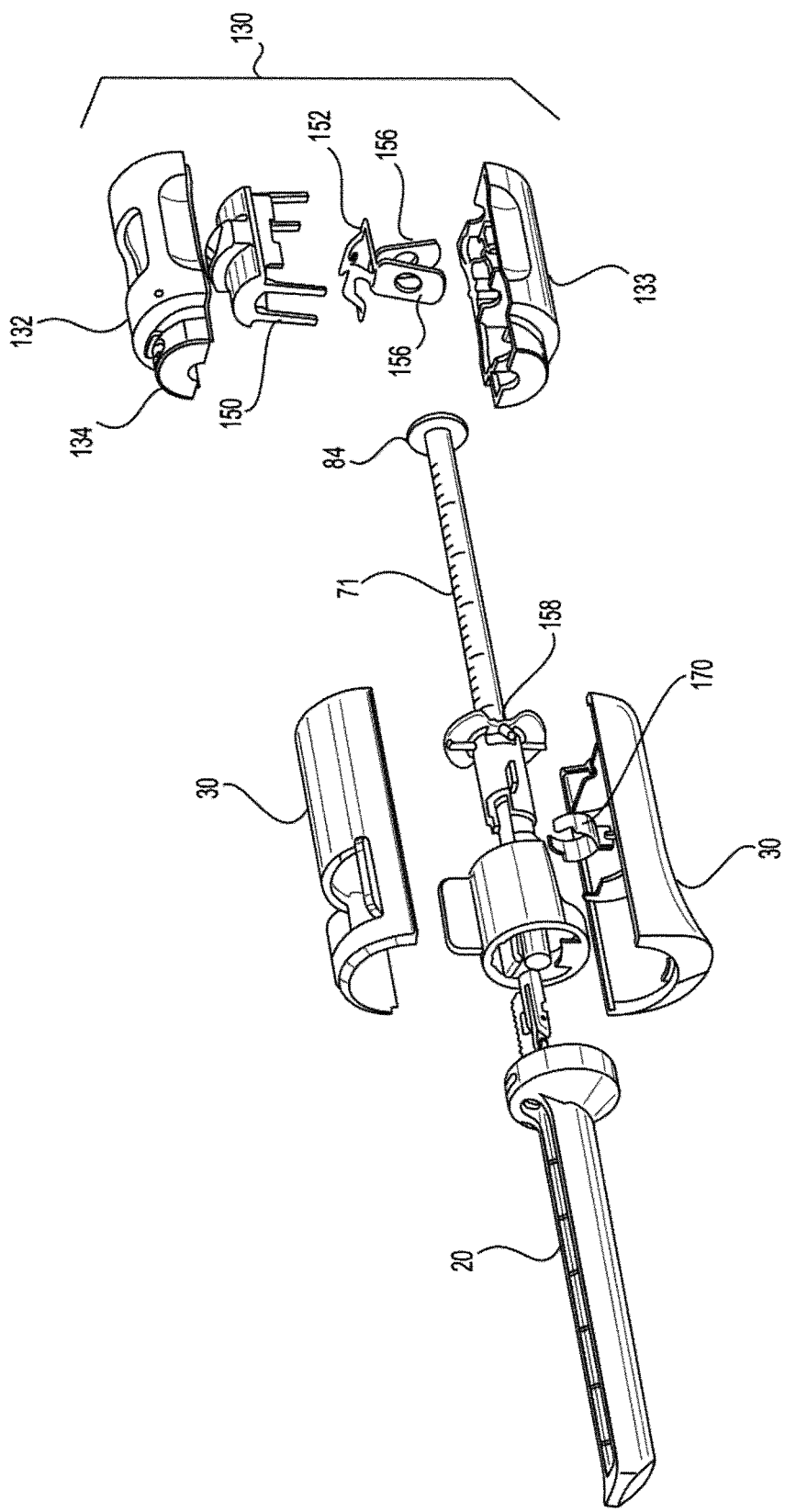
FIG. 29 is an exploded view of the embodiment depicted in FIG. 27 and FIGS. 28A-D.

FIG. 29 shows an exploded view of the embodiment of the device shown in FIGS. 27 and 28. One particular feature of this embodiment is the addition of a scope lock assembly 130, which can also serve as a handle for advancing or withdrawing the tube assembly 71 into/from the slotted clear cannula 20 of the device. In such an embodiment, the tube stop 84 element of the tube assembly 71 is retained within the neck 134 of the scope lock assembly 130. The tube stop 84 can freely rotate within the neck 134 so that the scope lock assembly 130 can be twisted to lock into the back of the main housing 30. In some embodiments, the scope lock assembly 130 comprises a four part locking mechanism comprising a scope lock button 150, a plate return spring 152 and a pair of locking plates 156. When the scope lock button 150 is depressed, the plate return spring 152 brings the locking plates 156 towards a parallel configuration, allowing a scope to be freely moved through the holes in the locking plates 156 into or out of the lumen of the tube assembly 71. When the scope lock button 150 is released, the plate return spring 152 allows the locking plates 156 to return to their default configuration and the scope is immobilized within the holes, thereby locking the position of the scope in, or extending through, the tube assembly. This embodiment of a scope lock mechanism is an exemplary embodiment and is not limiting on the device. Any scope lock device that can be envisioned to function with the present device is within the scope of the present application.

Figure 30D:
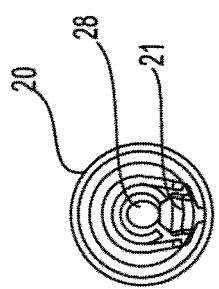
FIGS. 30A-E show perspective and cross-sectional views of another embodiment of the cannula element of the device.
Figure 30E:
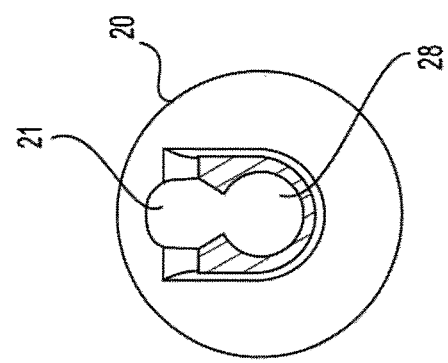
Figure 30C:
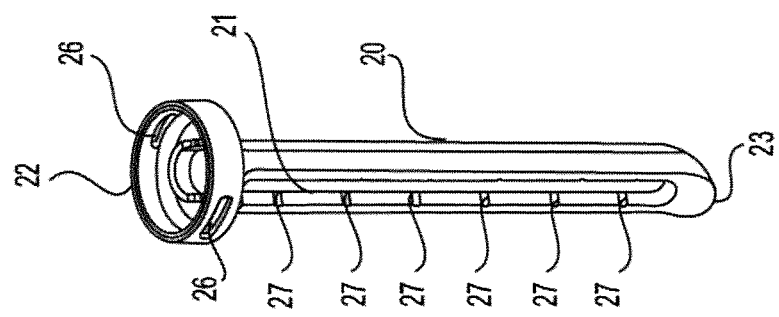
Figure 30B:
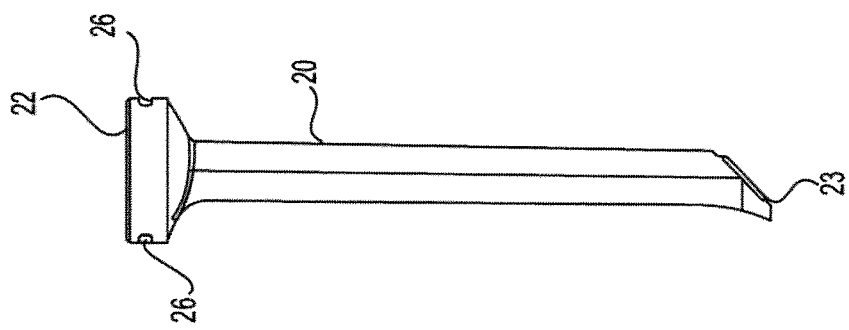
Figure 30A:
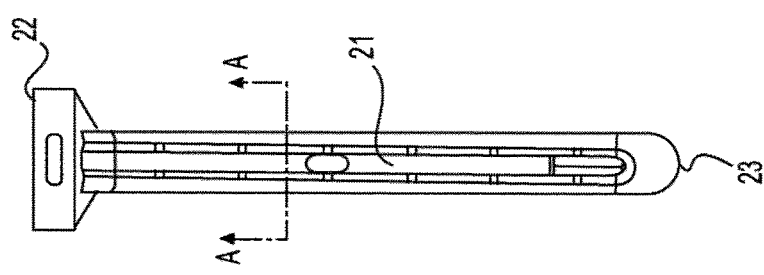

FIGS. 30A-E show details of the clear cannula element of the embodiment of the device shown in FIGS. 27 and 28A-D. FIG. 30A shows the cannula 20 from the top, showing the slot 21 extending longitudinally from the proximity of the proximal end 22 to the proximity of the distal end 23. Also visible are the depressions, slots, or holes 26 that engage with tabs or pins on the front of the housing. In some embodiments, the sides of the slot 21 comprise texture or tick marks 27 that are at a measured distance from one another down the length of the slot 21. The tick marks 27 minimally engage with the carrier of the blade and/or scraper as it advances, or retreats, along the length of the slot 21 to allow the practitioner to feel, or otherwise determine, how far the carrier has advanced along the slot. In some embodiments, the distal end 23 of the cannula 20 is a blunted and closed to eliminate the need of an obturator. Since the cannula 20 is made from a transparent material, the closed distal end 23 would still allow observation of the surrounding tissue with an endoscope. In some embodiments, the closed distal end 23 is turned up and has a sharpened edge that allows the cannula to separate tissues without the need to first use an elevator. In some embodiments, the distal end 23 is a tapered, tongue-shaped protrusion that forms an angle with the body of the cannula 20 that may serve as an elevator. In some embodiments, the cannula 20 has a total length in the range of 25-200 mm, 25-150 mm, 25-100 mm, 25-75 mm, 25-50 mm, 50-200 mm, 50-150 mm, 50-100 mm, 50-75 mm, 75-200 mm, 75-150 mm, 75-100 mm, 100-200 mm, 100-150 mm or 150-200 mm. In other embodiment, the cannula 20 has a total length of about 50 mm, about 60 mm, about 70 mm, about 75 mm, about 80 mm, about 90 mm or about 100 mm. In one embodiment, the cannula 20 has a total length of about 76.2 mm. In another embodiment, the cannula 20 has a total length of about 71 mm.

FIG. 30B shows a side view of the cannula 20, showing the proximal 22 and distal 23 ends, as well as the depressions, slots, or holes 26 that engage with tabs or pins on the front of the housing. In this embodiment, the distal end 23 of the cannula is closed and angled upwards to serve as an elevator. In some embodiments, the angle 29 is in the range of about 180-135 degrees, about 170-140 degrees, about 165-145 or about 160-150 degrees. In some embodiments, the distal end 23 has a blunted edge. In other embodiments, the distal end 23 has a sharpened edge. As used herein, the term "sharpened," as it related to the cannula, refers to an edge or portion of the cannula that has a angle and/or shape that allows the cannula to push through/between or to separate tissues, without cutting a tissue. The closed distal end 23 of the cannula allows the cannula to be used without the need of inserting a separate obturator into the lumen of the cannula, thereby providing the advantage of eliminating the steps of inserting and removing an obturator into/from the cannula during an endoscopic surgical procedure. The sharpened edge of the distal end 23 allows the cannula to be inserted into an entry portal and create a plane to and/or beyond the target tissue without the need for first inserting an instrument, such an elevator, through the entry portal for creating the plane. This provides the advantage of eliminating the steps of inserting and removing an elevator (or similar instrument) through the entry portal prior to the insertion of the cannula.

FIG. 30C depicts an angled view of the clear cannula 20 of the device. The proximal end 22 is configured to be engaged with another device, such as the housing 30. In some embodiments, the depressions, slots, or holes 26 that engage with tabs or pins on the front of the housing 30 are located on the top and bottom of the proximal end 22 of the cannula. In some embodiments, rather than individual or multiple depressions, slots, or holes 26 on the top, bottom or sides of the cannula 20, the depression 26 may be an impression or groove that runs all the way around the outside of the proximal end 22 of the cannula 20 and engages with an annular ring that runs around the inside of the distal end of the housing.

FIG. 30D shows an end view of the cannula at the proximal end 22. The view shows the slot 21, which is contiguous with the central lumen 28 of the cannula. In some embodiments, the central lumen 28 has a diameter in the range of 2-10 mm, 2-8 mm, 2-6 mm, 2-4 mm, 4-10 mm, 4-8 mm, 4-6 mm, 6-10 mm, 6-8 mm or 8-10 mm. In certain embodiments, the central lumen 28 has a diameter of about 2 mm, about 3 mm, about 4 mm, about 5 mm, about 6 mm, about 7 mm, about 8 mm, about 9 mm or about 10 mm. The width of the slot 21 may vary to adapt to the diameter of the central lumen 28 and the width of the blade assembly 190. In a particular embodiment, the central lumen 28 has a diameter of about 4.8 mm and the slot 21 has a width of about 2.3 mm. In this embodiment, the proximal end 22 has a diameter that is larger than the diameter of the cannula body.

FIG. 30E is a cross-sectional view of the cannula 20 at bisecting line A-A in FIG. 30A, looking towards the proximal end 22 of the cannula 20. The longitudinal slot 21 in the top surface of the cannula 20 can be seen to be contiguous with the central lumen of the cannula tube 20.

Figure 31D:
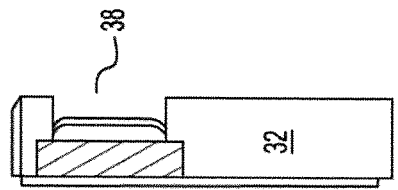
FIGS. 31A-F show perspective and cross-sectional views of the top shell of the housing of the embodiment depicted in FIG. 27.
Figure 31C:
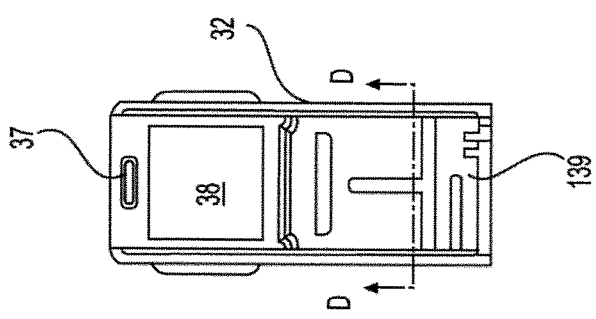
Figure 31F:
Figure 31B:
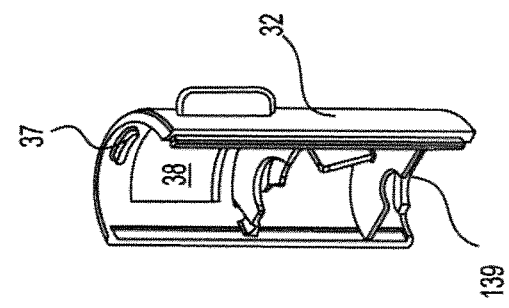
Figure 31E:
Figure 31A:
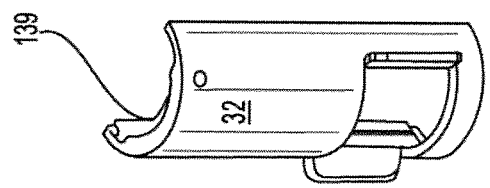

FIGS. 31A-F show various views of an embodiment the top half 32 of the main housing 30 of the device, more particularly of the device shown in FIGS. 27 and 28, wherein the device further comprises a scope lock. FIG. 31A shows the outside of one embodiment of the top half 32 of the housing 30 at an angle, while FIG. 31B shows the inside of one embodiment of the top half 32 of the housing 30 at an angle. FIG. 31C shows the inside of one embodiment of the top half 32 of the housing 30, showing one embodiment of a tab or pin 37 that engages with a depression, slot, or hole 26 located on the proximate end of the cannula shown in FIGS. 30A-E. In some embodiments, rather than individual or multiple tabs or pins at the distal end of the housing, the tab 37 may be an annular ring that runs around the inside of the distal end of the housing 30 and engages an impression or groove that runs all the way around the outside of the proximate end of the cannula. FIG. 31C also shows one embodiment of a locking mechanism 139 on the proximal end that engages with the locking mechanism 135 located on the neck 134 on the distal end of the scope lock housing 130 (see FIG. 29). FIG. 31D shows the upper half 32 of the housing 30 from a side view, while FIG. 31E shows a view of the top half 32 of the housing 30 from the distal end and FIG. 31F shows a cross-section view of the top half 32 of the housing 30 looking towards the distal end from the line bisecting FIG. 31C at D-D.

FIGS. 32A-F show various views of the lower half 33 of the main housing 30 of the device, more particularly of the device shown in FIGS. 27 and 28A-D, wherein the device further comprises a scope lock. FIG. 32A shows the outside of one embodiment of the lower half 33 of the housing 30 at an angle, while FIG. 32B shows the inside of one embodiment of the lower half 33 of the housing 30 at an angle. FIG. 32C shows the inside of one embodiment of the lower half 33 of the housing 30. FIG. 32C also shows one embodiment of a locking mechanism 139 on the proximal end that engages with the locking mechanism 135 located on the neck 134 on the distal end of the scope lock housing 130. FIG. 32D shows the lower half 33 of the housing 30 from a side view, while FIG. 32E shows a view of the lower half 33 of the housing 30 from the distal end and FIG. 32F shows a cross-sectional view looking towards the distal end of the lower half 33 of the housing 30 from the line A-A bisecting FIG. 32C.

FIGS. 33A-C show another embodiment of the blade assembly 190, comprising a pusher base 191 and a cutting blade 200. The blade assembly 190 is compatible with the embodiment of the device shown in FIG. 27, as well as with the embodiment of the device shown in FIGS. 9-10. FIG. 33A is a side perspective view of the blade assembly 190. The pusher base 191 comprises a notch 192 that positively engages with the tool selector 78 of the tube assembly (FIGS. 17A, C and D; FIGS. 28A, B). When the selector switch 61 of the revolver 60 (FIG. 10, FIGS. 28A, B) is rotated to the "BLADE" position, the blade assembly 190 is rotated upward by the slide lock 70 so that the notch 192 in the base of the blade assembly 190 slides onto and engages the tool selector 78. The tool selector 78 then firmly holds the blade assembly 190 on the surface of the tube assembly 71. Advancing the tube assembly 71 also advances the blade assembly 190 into the cannula 20 (FIG. 10; FIGS. 28A, B). The blade assembly 190 protrudes through the longitudinal slot 21 in the cannula 20 and advancement of the blade assembly 190 with the tube assembly 71 moves the blade 200 into contact with the target tissue. Further advancement of the blade assembly allows the blade 200 to separate the target tissue. In preferable embodiments, the bottom surface 210 of the blade 200 is at least slightly above the bottom surface 193 of the pusher base 191 so that the blade 200 does not directly contact the body of the tube assembly 71, which may affect rotation of the blade assembly 190 into place for deployment. In particular embodiments, the end of the pusher base opposite the blade 200 is angled 194 so that it does not catch tissues as it is being withdrawn through the slot 21 of the cannula 20. FIG. 33B is an end view of the blade assembly 190. The width of the pusher base 191 is such that it securely contacts the side walls of the slot 21 in the cannula 20 (FIG. 10; FIGS. 28A, B) but is still able to be advanced or withdrawn through the slot without an amount of friction that would impede its progress. The sides of the blade 200 do not contact the walls of the slot 21. In particular embodiments, the bottom surface 193 of the pusher base is curved to match the curvature of the tube assembly, thus inhibiting or preventing side to side motion, or wobble, of the blade assembly 190 during deployment. FIG. 33C is an angled perspective view of the blade assembly 190. The view is clear so that the attachment of the blade 200 to the pusher base 191 can be seen. In particular embodiments, the blade 200 comprises a tab 215 that embeds into the pusher base 191. In some embodiments the top surface of tab 215 is extended and is flush with the top surface of the pusher base 191. In particular embodiments there is a hole 220 in the tab 215 that allows the material of the pusher base 191 to flow through it when the pusher base 191 is cast, thereby securing the tab 215 into the pusher base 191. In some embodiments, the tab 215 is secured into the pusher base 191 using a pin or screw. In such an embodiment, the blade 200 may be replaceable in the blade assembly, allowing the use of blades with different profiles particularly suited for a specific surgical procedure. For example, it may be desirable to use a hook blade in some situations, where the cutting surface faces back towards the housing 30 of the device, allowing the practitioner to move the blade past the target tissue and separate the target tissue by pulling the blade backwards, rather than separating the target tissue upon advancing the blade. The pusher base 191 of the blade assembly 190 can be formed of any medically acceptable material, such as a plastic or ceramic, as it does come in contact with body tissues. In a particular embodiment, the pusher base 191 is formed of polycarbonate. In some embodiments, the blade assembly 190 may be replaced in the device with any other suitable blade tool that engages with the tool selector, such as, but not limited to, the blade 80 shown in FIG. 4 or a hooked endoscopic blade tool.

FIGS. 34A-E show a particular embodiment of the blade 200 as shown in FIGS. 28A-C. FIG. 34A shows a side view of the blade 200 embodiment. In a particular embodiment, the blade 200 as shown in FIG. 34A comprises an upper cutting surface 1 on the leading end of the blade, which is at an angle 2 with respect to the horizontal orientation of the blade 200, as defined by the bottom surface 210 of the blade 200. The angle 2 is such that the top of cutting surface 1 is forward of the bottom of the cutting surface. In one embodiment the angle 2 is between about 30 and about 45 degrees. In a particular embodiment, the angle 2 is between about 30 and about 40 degrees. In another particular embodiment, the angle 2 is between about 33 and about 39 degrees. In a more particular embodiment, the angle 2 is about 36 degrees.

In some embodiments, the upper end 3 of the cutting surface 1 is radiused. The radiused upper end 3 of the cutting surface 1 is about 90 degrees of a circle and has a radius measurement between about 0.50 mm and 1.50 mm. In a particular embodiment, the radius is about 0.94 mm.

In a particular embodiment, the blade 200 as shown in FIG. 34A comprises a lower cutting surface 4 on the leading end of the blade, which is at an angle 5 with respect to the horizontal orientation of the blade 200, as defined by the bottom surface 210 of the blade 200. The angle 5 is such that the bottom of the lower cutting surface 4 is forward of the top of the lower cutting surface. In one embodiment the angle 5 is between about 45 and about 65 degrees. In a particular embodiment, the angle 5 is between about 50 and about 60 degrees. In a more particular embodiment, the angle 5 is about 54 degrees. In some embodiments, the bottom of the lower cutting surface 4 is not radiused, as the bottom of the lower cutting surface 4 remains within the slot 21 of the cannula 20 (FIG. 28A, B) during deployment.

In a particular embodiment, the blade 200 as shown in FIG. 34A comprises upper cutting surface 1 and lower cutting surface 4 on the leading end of the blade 200, which are at an angle 6 to one another and meet at a central crotch 7. In one embodiment the angle 6 is between about 80 and about 100 degrees. In a further embodiment, the angle 6 is between about 85 and about 95 degrees. In a still further embodiment, the angle 6 is about 90 degrees.

Still referring to FIG. 34A, in some embodiments, the plane where the upper and lower cutting surfaces meet is angled downward 8 towards the crotch 7. In some embodiments, the angle 8, as it relates to the plane defined by the bottom surface 210 of the blade, is between about 0 and 20 degrees. In further embodiments, the angle 8, as it relates to the plane defined by the bottom surface 210 of the blade, is between about 5 and 15 degrees. In a particular embodiment, the angle 8, as it relates to the plane defined by the bottom surface 210 of the blade, is about 9 degrees. In particular embodiments, the crotch 7 is ground to have a maximum radius of between about 0.18 mm and about 0.58 mm, more particularly between about 0.28 mm and about 0.48 mm. In a still more particular embodiment, the crotch 7 is ground to have a maximum radius of about 0.381 mm.

In some embodiments, in order to prevent the blade 200 from catching on tissues when the blade 200 is drawn backwards through the cannula 20, the top surface 211 of the blade 200 is angled downward and meets the top 214 of the tab 215 which embeds into the pusher base 191 of the blade assembly 190 (FIGS. 33A-C). In a particular embodiment, the vertical height of the radius 3 at the top end of the upper cutting surface 1 above the top edge 214 of the tab 215 is between about 0.25 mm and about 0.75 mm, more particularly between about 0.35 mm and about 0.65 mm. In a more particular embodiment, the vertical height 229 of the radius 3 at the top end of the upper cutting surface 1 above the top edge 214 of the tab 215 is about 0.51 mm.

Additionally, in some embodiments, the trailing end 216 of the bottom surface 210 of the blade 200 may be angled up to the bottom edge 217 of the tab 215. In a particular embodiment, the tab 215 is notched 219, so that the extended end of the tab is able to clear the notch 192 in the pusher base 191. In a particular embodiment, the vertical height between the bottom surface 210 of the blade 200 and the bottom edge 217 of the tab 215 is between about 0.1 mm and about 1.0 mm, more particularly between about 0.3 mm and about 0.7 mm. In a more particular embodiment, the vertical height between the bottom surface 210 of the blade 200 and the bottom edge 217 of the tab 215 is about 0.5 mm.

Still referring to FIG. 34A, in some embodiments, the tab 215 is between about 2.0 mm and about 3.0 mm high between the top edge 214 and bottom edge 217 of the tab 215, more particularly between about 2.15 mm and about 2.85 mm. In a still further embodiment, the tab 215 is about 2.5 mm high between the top edge 214 and bottom edge 217 of the tab 215. Additionally, in some embodiments, the center of hole 220 is between about 6.0 mm and about 9.0 mm long from the trailing edge 218 of the tab 215, more particularly between about 7.0 mm and about 8.0 mm. In a still more particular embodiment, the center of hole 220 is about 7.5 mm from the trailing edge 218 of the tab 215. The hole 220 in the tab 215 that serves to secure the blade 200 into the pusher base 191 (FIG. 33C) is generally centered in the tab 215 in order to provide maximum adhesion of the tab 215 to, and stability within, the pusher base 191. The diameter of the hole 220 is between about 0.5 mm and about 2.0 mm, more particularly between about 1.0 mm and about 1.5 mm. In a more particular embodiment, the diameter of the hole 220 is about 1.25 mm.

In some embodiments, the crotch 7 of the blade 200 is between about 8.0 mm and about 12.0 mm forward of the trailing edge 218 of the tab 215, more particularly between about 9.0 mm and about 11.0 mm. In a still more particular embodiment, the crotch 7 of the blade 200 is about 10.25 mm forward of the trailing edge 218 of the tab 215. In some embodiments, the total length of the cutting surface 221 of the blade 200 from the leading point of the upper cutting surface 1 to the trailing point 222 of the grind forming the crotch 7 is between about 1.5 mm and about 4.5 mm. In another particular embodiment, the total length of the cutting surface 221 of the blade 200 from the leading point of the upper cutting surface 1 to the t trailing point 222 of the grind forming the crotch 7 is between about 2.25 mm and about 3.75 mm. In a more particular embodiment the total length of the cutting surface 221 of the blade 200 is about 3.107 mm.

In particular embodiments, the blade 200 is made from stainless steel. In a further embodiment, the stainless steel is martensitic stainless steel. An exemplary martensitic stainless steel is Bohler-Uddeholm AEB-L martensitic stainless steel. In a still further embodiment, the martensitic stainless steel is heat-treated. In another further embodiment, the stainless steel is 440 A stainless steel. In a particular embodiment, the blade is made from Hitachi GIN-5 SST-MODIFIED 440-A stainless steel. The blade is optionally flash electropolished or passivated per ASTM A967, or by any other method that delivers a similar finish. The cutting edges are machine finished and must be sharp. In a particular embodiment, the steel of the blade is heat-treated to Rockwell C hardness of about 50-72. In a more particular embodiment, the steel of the blade is heat-treated to R30N 75.7-77.5 (Rockwell C hardness of 58-60).

Referring now to FIG. 34B, the lower cutting surface 4 is a single beveled cutting surface and the angle 9 is between about 30 degrees and about 50 degrees. In some embodiments, the angle 9 is between about 35 degrees and about 45 degrees. In a particular embodiment, the angle 9 is about 40 degrees. While not shown in the figure, the upper cutting surface 1 is a similarly a single beveled cutting surface and the angle is between about 30 degrees and about 50 degrees. In some embodiments, the angle is between about 35 degrees and about 45 degrees. In a particular embodiment, the angle is about 40 degrees. In some embodiments, the total depth 223 of the sharp surface of the blade 200 is between about 0.5 mm and about 1.2 mm. In another particular embodiment, the total depth 223 of the sharp surface of the blade 200 is between about 0.75 mm and about 0.95 mm. In a more particular embodiment the total depth 223 of the sharp surface of the blade 200 is about 0.864 mm.

Also referring to FIG. 34B, in some embodiments, the depth of the grind 225 of lower cutting surface 4, as well as for upper cutting surface 1, is between about 0.6 mm and about 1.1 mm. In other embodiment, the depth of the grind 225 is between about 0.7 mm and about 1.0 mm. In a further embodiment, the depth of the grind 225 is about 0.86 mm.

Referring now to FIG. 34C, in a particular embodiment, the overall height 226 of the body of the blade 200 is between about 3.0 mm and about 4.0 mm. In another embodiment, the height 226 of the body of the blade 200 is between about 3.25 mm and about 3.75 mm. In a more particular embodiment, the height 226 of the body of the blade 200 is about 3.5 mm. Again referring to FIG. 34C, in a particular embodiment, the width 227 of the body of the blade 200 is between about 0.3 mm and about 0.9 mm. In another embodiment, the width 227 of the body of the blade 200 is between about 0.45 mm and about 0.75 mm. In a particular embodiment, the width 227 the body of the blade 200 is about 0.635+/−0.025 mm.

Referring to FIG. 34D, the total length 228 of the blade 200 from the leading point of the upper cutting surface 1 to the trailing end 218 of the tab 215 is between about 8.0 mm and about 16.0 mm. In another particular embodiment, the total length 228 of the blade 200 from the leading point of the upper cutting surface 1 to the trailing end 218 of the tab 215 is between about 10.0 mm and about 14.0 mm. In a more particular embodiment the total length 228 of the blade 200 is about 12.151 mm. FIG. 34E presents an angled perspective view of an embodiment of the blade 200.

Figure 35E:
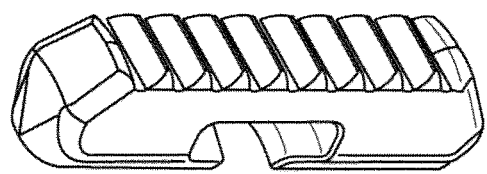
FIGS. 35A-E show perspective and cross-sectional views of an embodiment of the scraper element of the device.
Figure 35D:
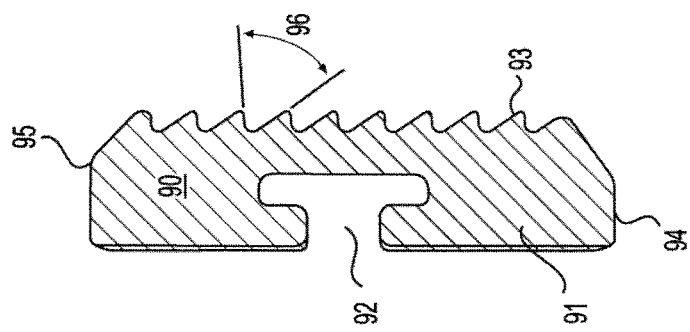
Figure 35C:
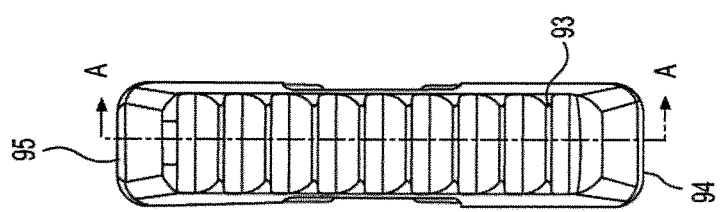
Figure 35A:
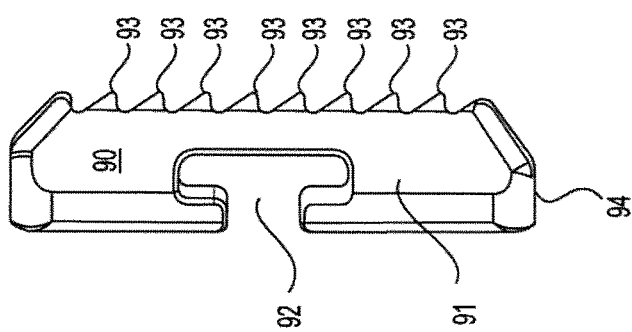

FIGS. 35A-E show an embodiment of the scraper 90 of the compact endoscopic surgical device depicted in FIGS. 27 and 28A-D. As seen in FIG. 35A, the base 91 of the scraper 90 comprises a notch 92 that positively engages with the tool selector 78 of the tube assembly (FIG. 38). When the selector switch 61 of the revolver 60 (FIG. 28) is rotated to the "SCRAPER" position, the scraper 90 is rotated upward by the slide lock 70 so that the notch 92 in the base 91 of the scraper 90 slides onto and engages the tool selector 78. The tool selector 78 then firmly holds the scraper 90 on the surface of the tube assembly 71. Advancing the tube assembly 71 also advances the scraper 90 into the cannula 20 (FIG. 28). The teeth 93 of the scraper 90 protrude through the longitudinal slot 21 in the cannula 20 and advancement of the scraper 90 with the tube assembly 71 moves the teeth 93 into contact with the target tissue. Further advancement of the blade assembly allows the teeth 93 to rake across the target tissue. In particular embodiments, the distal end 94 and proximate end 95 of the base 91 are rounded and angled downwards so that they do not catch tissues as the scraper 90 is being advanced or withdrawn through the slot 21 of the cannula 20.

Figure 35B:
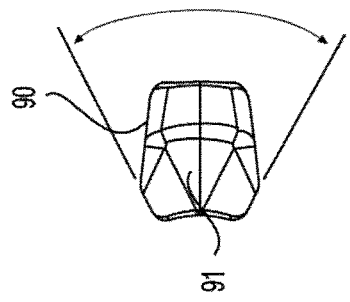

FIG. 35B is an end view of the scraper tool 90. The width of the base 91 is such that it securely contacts the side walls of the slot 21 in the cannula 20 (FIG. 28) but is still able to be advanced or withdrawn through the slot without an amount of friction that would impede its progress. In particular embodiments, the bottom surface of the base 91 is curved to match the curvature of the tube assembly, thus inhibiting or preventing side to side motion, or wobble, of the scraper 90 during deployment.

FIG. 35C is a perspective view of the top of the scraper 90 showing the linear arrangement of the teeth 93. FIG. 35D is a cross-sectional view of the scraper 90 at the line A-A through FIG. 35C. In some embodiments, the teeth 93 are angled 96 to each other at between about 45 degrees and 75 degrees, more particularly between about 55 degrees and about 65 degrees. In a still more particular embodiment, the teeth 93 are angled 96 to each other at about 60 degrees. In some embodiments the teeth 93 are between about 1.0 mm and about 6.0 mm in height, more particularly between about 2.0 mm and about 4.0 mm. In a still more particular embodiment, the teeth 93 are about 3.24 mm in height from where the base 91 contacts the tube assembly 71. FIG. 35E is a perspective view of the scraper 90 from an angle. The scraper 90 can be formed of any medically acceptable material, such as a plastic, ceramic, stainless steel, or nitinol, as it does come in contact with body tissues. In a particular embodiment, scraper 90 is formed of polycarbonate.

Figure 36C:
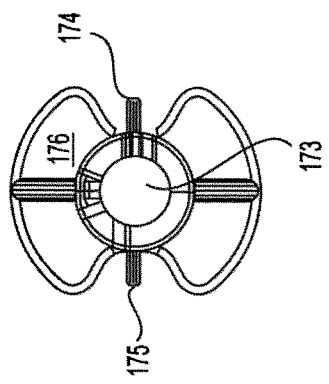
FIGS. 36A-E show perspective and cross-sectional views of the slide lock element of the embodiment depicted in FIG. 27.
Figure 36E:
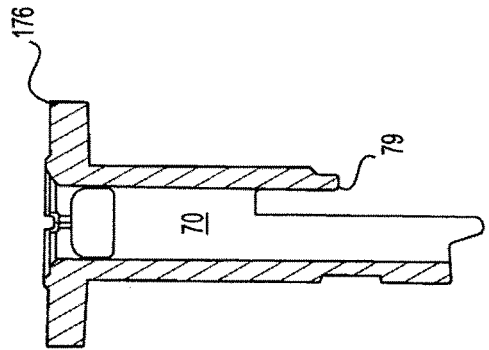
Figure 36B:
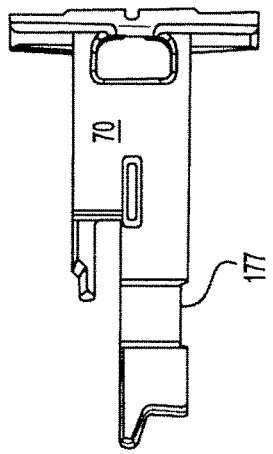
Figure 36D:
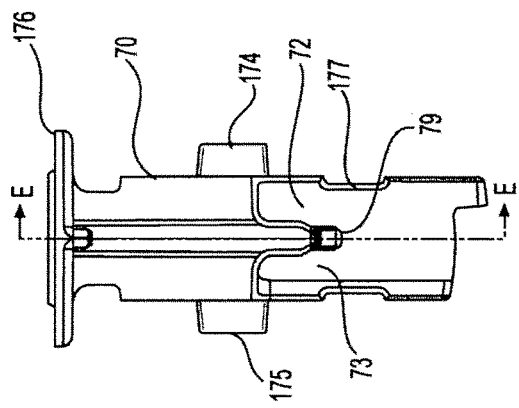
Figure 36A:
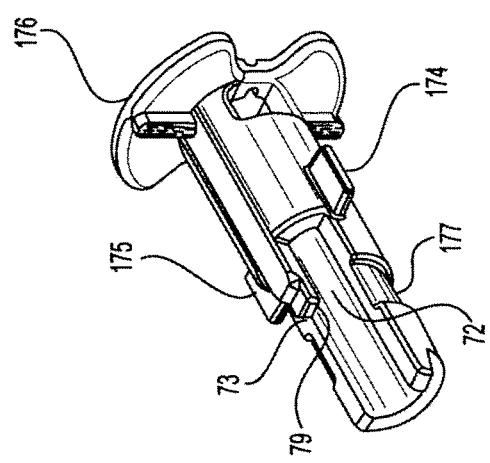

Turning to FIGS. 36A-E, shown is another embodiment of a slide lock 70 of the device. FIG. 36A shows the slide lock 70 from an angled perspective. The slide lock 70 comprises two notches 72,73 that hold the scraper 90 and blade assembly 190 in place when they are parked, as well as rotate them into the ready position when they are selected for use by rotation of the revolver 60 (FIGS. 28A, B, for example). The two notches 72,73 are separated from one another by the tab 79. The front of the tab 79 engages with the tab 68 (FIG. 42D, for example) of the revolver 60 when the selector switch 61 is not lined up with the "SCRAPER" or "BLADE" options, thus preventing the scraper 90 or blade assembly 190 from being deployed into the cannula when not in use. In some embodiments, the slide lock 70 comprises a retaining groove 177 that holds a rotary clip 170 (FIGS. 41A-E, for example) in place, preventing the rotary clip from sliding forward or backward on the slide lock 70. The rotary clip 170 does not rotate with the revolver 60 and slide lock 70, serving to prevent the scraper 90 or blade assembly 190 from sliding forward out of their notches 72,73 when they are not selected. Some embodiments of the slide lock 70 further comprise a pair of wings 174,175 that engage with the revolver 60 (FIGS. 42A-E, for example) for turning the slide lock 70 when a particular tool, such as "SCRAPER," "BLADE" or "SCOPE" is selected. Some embodiments of the slide lock 70 further comprise a disc 176 at the proximate end. The outer rim of the disc 176 contacts the inside surface of the housing 30 (FIG. 29) to allow the slide lock 70 to rotate, but prevents or constrains side-to-side or up-down movement of the slide lock in the device. In some embodiments, the sides of the disc 176 are notched inwards towards the body of the slide lock 70.

Still referring to FIG. 36, FIG. 36B is a side view of the slide lock 70, showing the position of the retaining grove 177. FIG. 36C shows an end view of slide lock 70, looking from the distal end towards the disc 176 at the proximate end. The center lumen 173 of the slide lock 70 allows the passage of the tube assembly 71 through the slide lock 70 and into the cannula 20 (FIG. 28A, B). FIG. 36D is a perspective view of the slide lock 70 from the top, while FIG. 36E is a longitudinal cross-section view at line E-E through FIG. 36D.

FIGS. 37A-D show perspective views of an embodiment of an extension spring 158 of the device, more particularly of the device shown in FIGS. 27 and 28A-D. Two extension springs 158 are mounted at one end on the disc 176 at the proximate end of the slide lock, opposite one another in relation to the lumen for the tube assembly 71 (See FIG. 29, for example). The opposite ends of extension springs 158 are mounted on attachment points 159 (FIG. 29 and FIGS. 32B, D-F) on the main housing 30. The extension springs 158 retain the slide lock 70 in the "SCOPE" (safe or no tools) position as a default and control the rotation of the slide lock 70 when the revolver 60 is turned. The extension springs 158 also assist in returning the slide lock 70 and revolver 60 back to the "SCOPE" position when a tool is withdrawn from the cannula 20 back into its notch 72,73 in the slide lock 70.

FIGS. 38A-D show an embodiment of a tube assembly 71 of the device, as it interacts with an embodiment of the slide lock 70. In some embodiments, the tube assembly is composed of stainless steel, preferably AISI 304 stainless steel. However, the tube assembly can be made from any suitable material including, but not limited to, aluminum, titanium, nitinol or other metal alloys, or plastic. In some embodiments where the tube assembly 71 is made of plastic, the plastic may be clear, allowing visualization with an endoscope of tissues surrounding the cannula 20 through the body of the tube assembly 71.

Figure 38D:
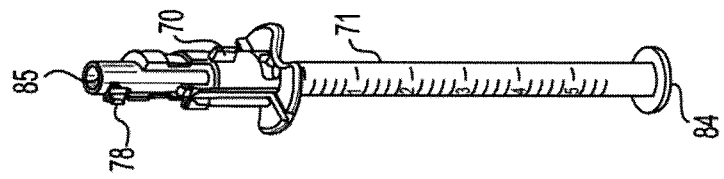
FIGS. 38A-D show perspective and cross-sectional views of a tube assembly element of the device as it interfaces with the slide lock element of the embodiment depicted in FIGS. 31A-E.
Figure 38C:
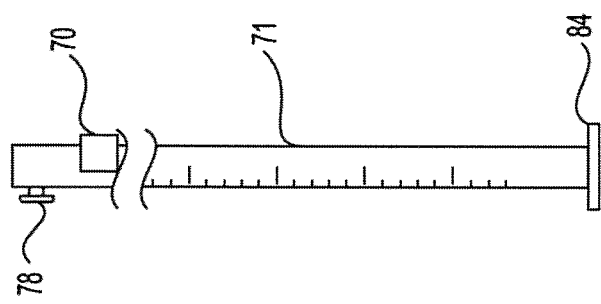
Figure 38B:
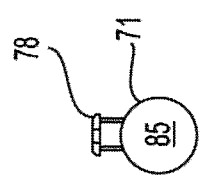
Figure 38A:
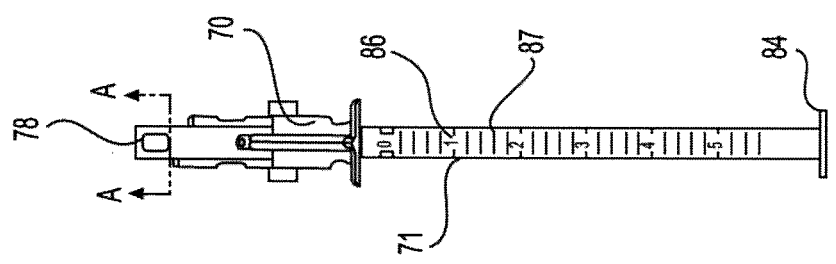
Figure 39B:
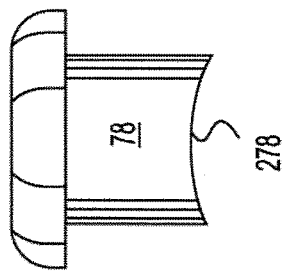
FIG. 39A-D show perspective views of an embodiment of a tool selector element of the tube assembly.
Figure 39D:
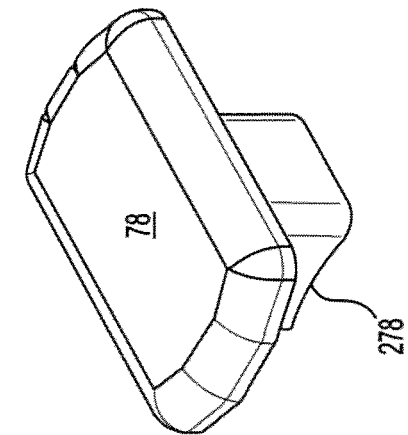
Figure 39A:
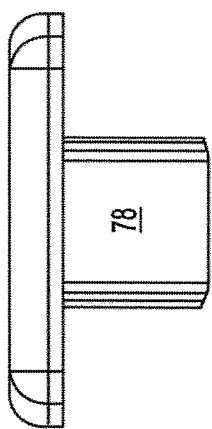
Figure 39C:
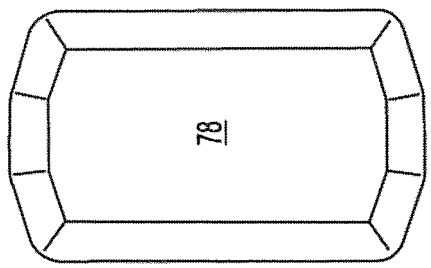

FIG. 38A is a top view of the tube assembly 71. The body of the tube assembly 71 slides through the center lumen 173 of the slide lock 70. The tube assembly 71 comprises near its distal end a tool selector 78. The tool selector 78 is directly on top of the tube assembly 71. With reference to FIGS. 28A and B, when the selector switch 61 of the revolver 60 is positioned at the "SCOPE" setting, no tools are engaged with the tool selector 78 and the tube assembly 71 can be advanced into the cannula 20 without the blade assembly 190 or scraper 90. When the selector switch 61 of the revolver 60 is mover to the "BLADE" setting, the revolver 60 rotates the slide lock 70 such that the notch 72 holding the blade assembly 190 is moved to the top of the tube assembly 71 and the notch in the bottom surface of the blade assembly 190 is positively engaged with the tool selector 78. Advancement of the tube assembly 71 would cause the advancement of the blade assembly 190 into and down the length of the cannula 20, protruding through the slot 21. When the selector switch 61 of the revolver 60 is mover to the "SCRAPER" setting, the revolver 60 rotates the slide lock 70 such that the notch 73 holding the scraper 90 is moved to the top of the tube assembly 71 and the notch in the bottom surface of the scraper 90 is positively engaged with the tool selector 78. Advancement of the tube assembly 71 would cause the advancement of the scraper 90 into and down the length of the cannula 20, protruding through the slot 21. In some embodiments, the tool selector 78 is welded, preferably laser welded, onto the top of the tube element of the tube assembly 71. In a preferred embodiment, the tool selector 78 is welded all around at its base to the tube element. In particular embodiments, the strength of the weld should be able to withstand the application of 5 in-lbs. torque to the unit, more particularly 10 in-lbs. torque. The tube assembly 71 further comprises a tube stop 84 at the proximate end of the tube element. The tube stop 84 retains the tube assembly 71 in the housing of the device, preventing the tube assembly from passing forward completely through the proximate end of the scope lock housing 130. In some embodiments, the tube stop 84 is welded flush with the proximate end of the tube element of the tube assembly. In particular embodiments, the weld should be strong enough to withstand at least 10 lbs. normal force to the face, more particularly 20 lbs. normal to the face.

The tube assembly 71 can optionally be marked on the top or side surface with gradations 86,87 as exemplified in FIG. 38A to show the distance that the tube assembly 71 has been advanced into the cannula 20. As a non-limiting example, major gradations 86 can be made to show each centimeter in distance that the tube assembly 71 has been advanced into the cannula 20, with minor gradations 87 between them to show, for example, each 1, 2, 2.5 or 5 millimeters. While the gradations can be applied to the tube assembly 71 by any means known in the art, it is preferable to lasermark the gradations on the tube assembly 71 for accuracy and permanence. In some embodiments, the distance between the major or minor gradations 86,87 corresponds to the distance between the tick marks 27 (FIG. 30A) in the sides of the slot 21 in the cannula 20.

FIG. 38B shows a cross-section of the tube assembly 71 at the line bisecting FIG. 38A at A-A and looking in the direction of the tool selector towards the distal end. The tube assembly 71 has a central lumen 85 that accommodates the insertion and free passage of an endoscope or other viewing device or tool, for example. FIG. 38C is a side view of the tube assembly 71 and FIG. 38D is a perspective view of the tube assembly 71 from an angle.

FIGS. 39A-D are perspective views of the tool selector 78 tab of the tube assembly 71. In some embodiments, the edges of the tool selector 78 are rounded in order to insure that sliding the notch 192 of the knife assembly 190 (FIGS. 18A and 30A, for example) or the notch 92 of the scraper 90 (FIGS. 23A and 35A, for example) occurs smoothly. The base 278 of the tool selector 78 can be rounded in order to assure solid mating of the tool selector 78 onto the tube assembly 71.

In some embodiments, the tube stop 84 of the tube assembly 71 is trapped within the neck 134 of the scope lock assembly (FIG. 29, for example), allowing the scope lock assembly 130 to be used as a handle for advancing/withdrawing the tube assembly 71 through the main housing 30 of the device and into/from the clear cannula 20 (FIG. 29, for example). The tube stop 84 can rotate within the neck 134 of the scope lock assembly 130 so that, in some embodiments, the scope lock assembly 130 can be twisted to lock/unlock it to/from the main housing 30, for example to keep the scope in a locked position within the clear cannula 20 during insertion or withdrawal of the cannula through a body opening or a channel between/through a body tissue during an endoscopic surgical procedure.

Figure 40A:
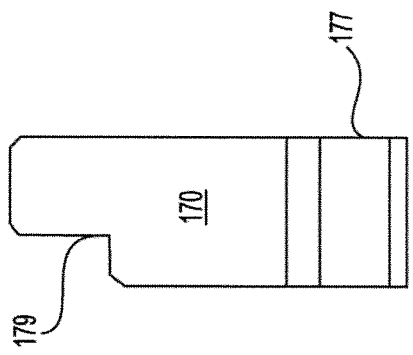
FIGS. 40A-E show perspective views of the rotary clip element of the embodiment depicted in FIG. 27.
Figure 40B:
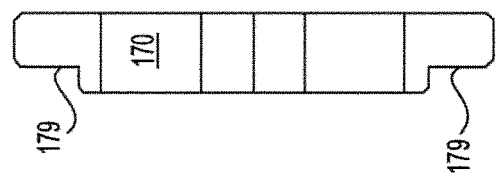
Figure 40C:
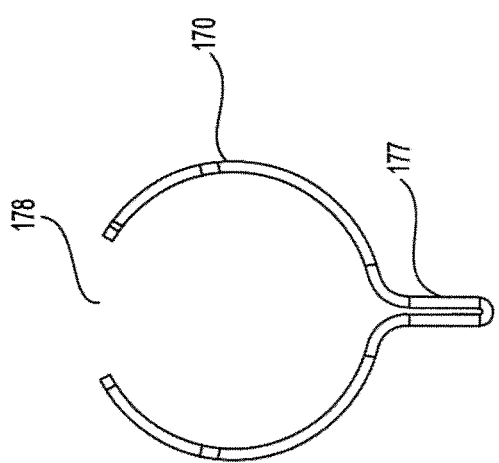
Figure 40D:
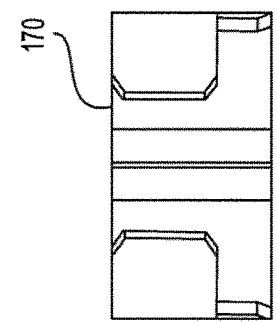
Figure 40E:
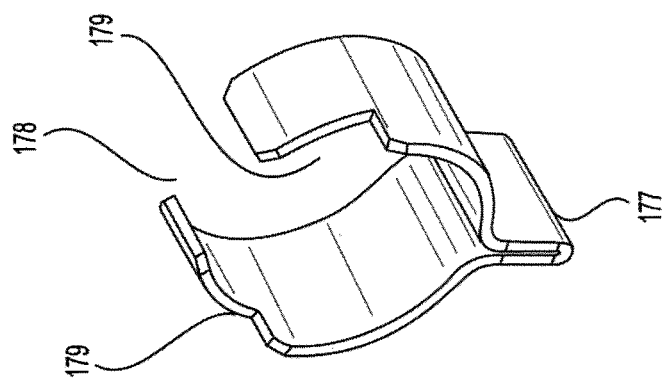

Turning now to FIGS. 40A-E, perspective views of an embodiment of a rotary clip 170 of the device are presented. In some embodiments, the rotary clip 170 is of a width that allows it to fit securely within the groove 177 of the slide lock 70 (FIGS. 36A, B, for example). FIG. 40A shows the rotary clip 170 from an angle. In some embodiments, the rotary clip 170 comprises a tab 177 that engages with the inside of the housing 30 to prevent the rotary clip 170 from rotating or sliding. The top of the rotary clip 170 is open 178, so that when the scraper tool or blade assembly is rotated into the deployment position, it can be deployed through the rotary clip 170 and into the cannula 20 (FIG. 28). FIG. 40B is a perspective view of the rotary clip 170 as viewed from the distal side towards the proximate side. FIG. 40C is a side perspective view of the rotary clip 170. In some embodiments, a portion of the distal side of the rotary clip 170 may be notched 179. FIG. 40D is a perspective view of the rotary clip 170 looking down upon the top. The rotary clip may be manufactured from any suitable material, such as plastic, stainless steel, aluminum, or metal alloys. In some embodiments, the rotary clip 170 may be formed, cut, stamped, cast or milled as a flat piece, as shown in FIG. 40E, from a malleable metal such as SS 303 and then formed into the final shape of being an open-topped ring with a tab at the bottom as shown in FIG. 40A. In other embodiments, the rotary clip 170 may be formed, cut, molded, 3D-printed, cast or milled from a suitable material as an open-topped ring with a tab at the bottom as shown in FIG. 40A.

FIGS. 41A-E show detailed views of an embodiment of the revolver 60 element of the device depicted in FIGS. 27-28, for example. FIG. 41A is an exterior perspective view of the revolver 60, showing a selector switch 61 that protrudes through the opening 38 (FIGS. 28A-B, for example) in the housing, as well as the proximate 63 and distal 64 ends of the revolver 60 element. The selector switch 61 is rotated from side to side by the user to select the appropriate instrument for a particular step in an endoscopic surgical procedure. FIG. 41B is a top view of the rotator 60 with the selector switch 61.

FIG. 41C is a view of the distal 64 end of the revolver 60. In some embodiments of the device, the revolver 60 comprises upper tabs 65 and lower tabs 66 that are used to select the scraper 90 or blade assembly 190 of the device. For example, when the selector switch 61 is rotated by the user to the position marked "SCRAPER" (see FIG. 28B, for example), the tabs 65 and 66 engage the scraper 90 and move it to the centerline (i.e., in line with the longitudinal slot 21 in FIG. 28B) of the device. There, the scraper 90 is engaged by the tool selector 78 on the tube assembly 71 (FIG. 38, for example) of the device, so that it can be deployed into the cannula 20 (FIG. 28, for example) and protrude through the longitudinal slot 21 (FIG. 28, for example) therein. When the selector switch 61 is rotated by the user to the position marked "BLADE" (see FIG. 28, for example), the tabs 65 and 66 engage the blade assembly 190 and move it to the centerline (i.e., in line with the longitudinal slot 21 in FIG. 28B) of the device. There, the blade assembly 190 is engaged by the tool selector 78 on the tube assembly 71 (FIG. 38, for example) of the device, so that it can be deployed into the cannula 20 (FIG. 28A) and protrude through the longitudinal slot 21 (FIG. 28A) therein. However, when the selector switch 61 is rotated by the user to the position marked "SCOPE" (see FIG. 28A, for example), the tabs 65 and 66 retain the scraper 90 and blade assembly 190 in their parked positions out of the centerline so that an endoscope, or other device, can be advanced through the tube 71 (FIG. 28A) into the cannula without either the scraper tool or blade assembly being advanced.

FIG. 41D is a cross-sectional view of revolver 60 at line D-D in FIG. 41B and looking in the direction of the proximate end 63 of the revolver 60. FIG. 41E is also a cross-sectional view of the revolver 60, this time along centerline E-E of FIG. 41C. As can be seen in this view, in some embodiments of the device, the revolver 60 comprises a hooked tab 68 that engages the front of the tab 79 that separates the notches (72, 73 in FIG. 36D, for example) in the slide lock 70 (see FIG. 36) that hold the scraper 90 and blade assembly 190. When the selector switch 61 is in the "SCOPE" position, for example, the hooked tab 68 helps ensure that neither the scraper tool nor blade assembly can be deployed into the cannula.

Figure 42C:
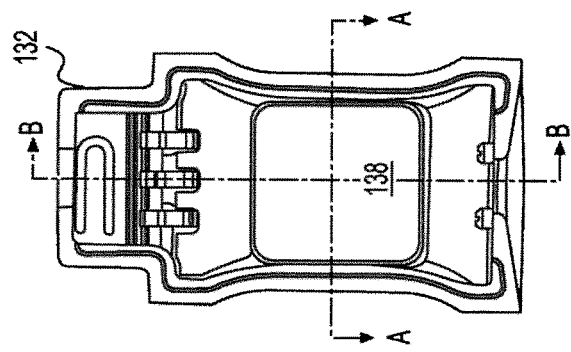
FIGS. 42A-F show perspective and cross-sectional views of the top portion of an exemplary housing for a scope lock component of the embodiment of the device depicted in FIG. 27.
Figure 42F:
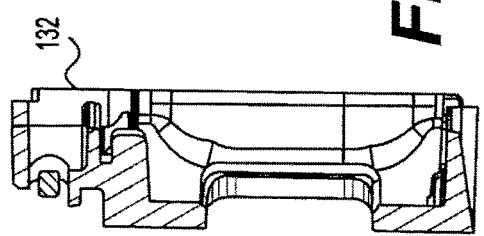
Figure 42B:
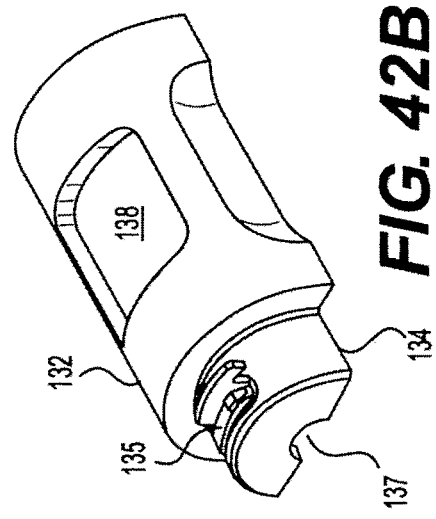
Figure 42E:
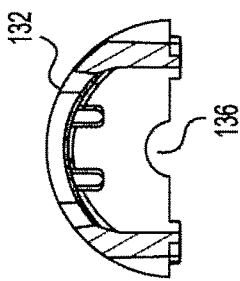
Figure 42A:
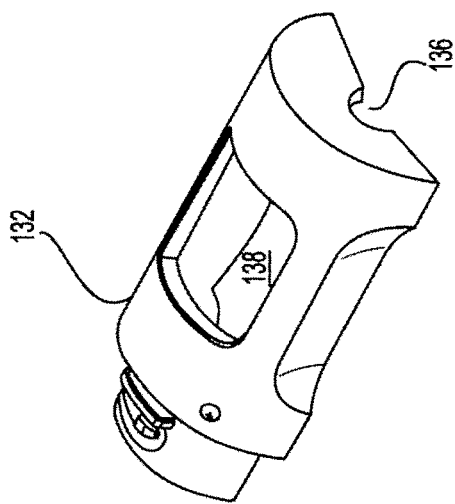
Figure 42D:
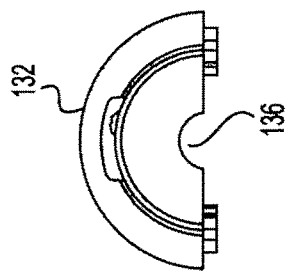
Figure 44C:
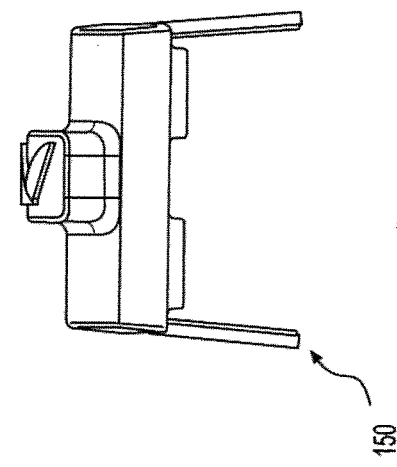
FIGS. 44A-E show perspective views of an embodiment of a scope lock button of the embodiment of the device shown in FIG. 27.
Figure 44E:
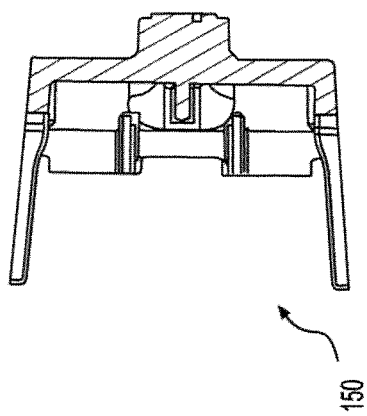
Figure 44B:
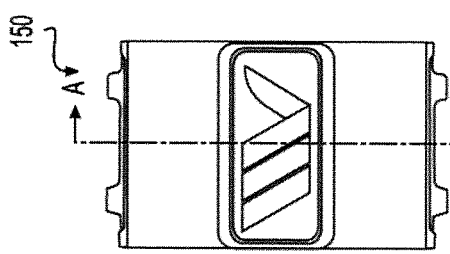
Figure 44D:
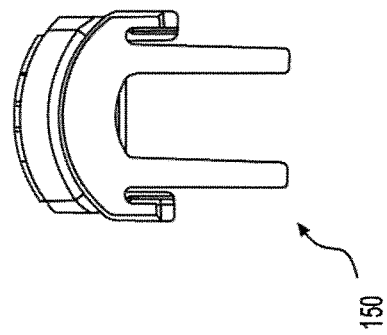
Figure 44A:
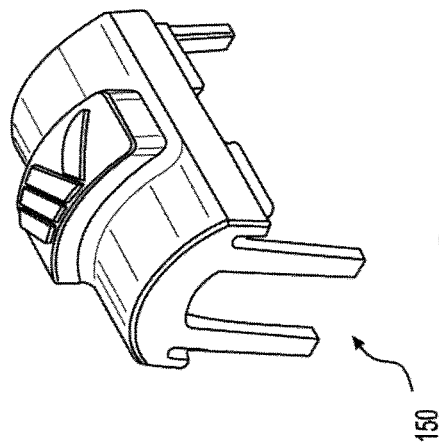
Figure 45C:
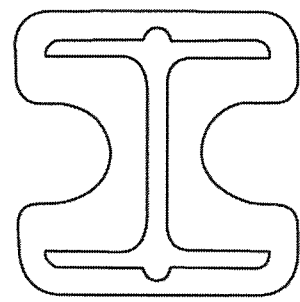
FIGS. 45A-E show perspective views of an embodiment of a plate return spring of the device.
Figure 45E:
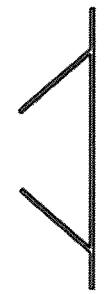
Figure 45B:
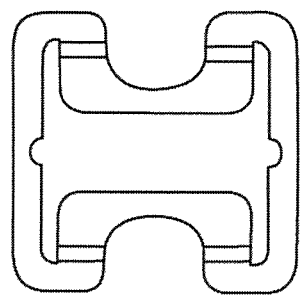
Figure 45D:
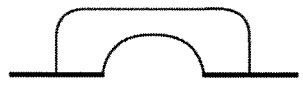
Figure 45A:
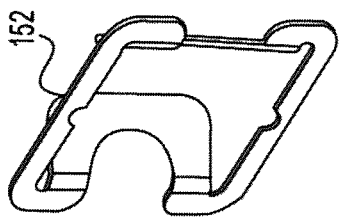

FIGS. 42A-F are views of the top shell 132 portion of the housing for an embodiment of a scope lock assembly 130 (see also FIG. 29) of some embodiments of the present device. In some embodiments, the assembly 130 comprises a neck 134 on the distal end of the housing that inserts into the main housing 30 (FIG. 28, for example) of the device. In other embodiments, the neck 134 is part of the housing 30 and inserts into the scope lock housing. In some embodiments, the neck 134 comprises a locking mechanism 135 that interacts with a counterpart mechanism on the housing 30. In particular embodiments, the proximate end of the scope lock housing 130 comprises a hole 136 for passing a viewing device (such as an endoscope or arthroscope) through. In particular embodiments, the diameter of the hole securely supports the viewing device without allowing it significant lateral motion, however, does not impede, for example by friction, the proximate or distal motion of the viewing device through the device. In some embodiments, the neck 134 comprises a corresponding supporting hole 137 in the distal end. In some embodiments, the supporting hole 137 in the distal end of the neck 134 comprises a hole large enough for the tube assembly 71 to pass through the hole, allowing the tube stop 84 to be retained in the lumen of the neck 134. By retaining the tube stop 84 within the neck 134 of the scope lock assembly 130, the scope lock assembly can be used as a handle for manipulation of the tube assembly 71. FIGS. 42A-B are perspective views of the top shell 132 of the housing of the scope lock assembly 130. FIG. 42C is a view of an exemplary inside of the top shell 132 of the housing of the scope lock assembly 130 and FIG. 42D is an end view of the distal end of the top shell 132 of the housing of the scope lock assembly 130. In some embodiments, the inside of the housing may comprise ridges or protrusions in order to support or retain the individual elements of the scope lock mechanism. FIG. 42E is a cross section of the top shell 132 of the housing of the scope lock assembly 130 as depicted in FIG. 42C at line A-A and looking in the proximal direction. FIG. 42F is a longitudinal section of the top shell 132 of the housing of the scope lock assembly 130 as depicted in FIG. 42C at line B-B.

FIGS. 43A-F are views of the bottom shell 133 of an embodiment of a housing of the scope lock assembly 130 of some embodiments of the present device. In some embodiments, the housing of the scope lock assembly 130 comprises a neck 134 on its distal end that inserts into the housing 30 (FIG. 28A-B, for example) of the device. In other embodiments, the neck 134 is part of the main housing 30 and inserts into the scope lock housing. In some embodiments, the neck 134 comprises a locking mechanism 135 that interacts with a counterpart mechanism on the main housing 30. In particular embodiments, the proximate end of the scope lock housing 130 comprises a hole 136 for passing a viewing device (such as an endoscope or arthroscope) through. In particular embodiments, the diameter of the hole securely supports the viewing device without allowing it significant lateral motion, however, does not impede, for example by friction, the proximate or distal motion of the viewing device through the device. In some embodiments, the neck 134 comprises a corresponding supporting hole 137 in the distal end. In some embodiments, the supporting hole 137 in the distal end of the neck 134 comprises a hole large enough for the tube assembly 71 to pass through the hole, allowing the tube stop 84 to be retained in the lumen of the neck 134. By retaining the tube stop 84 within the neck 134 of the scope lock assembly 130, the scope lock assembly can be used as a handle for manipulation of the tube assembly 71. FIGS. 43A-B are perspective views outside and inside, respectively, of the bottom shell 133 of the housing of the scope lock assembly 130. FIG. 43C is a view of an exemplary inside of the bottom shell 133 of the housing of the scope lock assembly 130 and FIG. 43D is an end view of the distal end of the bottom shell 133 of the housing of the scope lock assembly 130. In some embodiments, the inside of the housing may comprise ridges or protrusions in order to support or retain the individual elements of the scope lock mechanism. FIG. 43E is a cross section of the bottom shell 133 of the housing of the scope lock assembly 130 as depicted in FIG. 43C at line A-A and looking in the proximal direction. FIG. 43F is a longitudinal section of the bottom shell 133 of the housing of the scope lock assembly 130 as depicted in FIG. 43C at line B-B.

While a neck 134 with a locking mechanism 135 has been exemplified here, any suitable mechanism for joining the housing of the scope lock assembly 130 to the device housing 30 is envisioned in this application and is included within the scope of the present application. In some embodiments, the scope lock housing is integral with the main housing of the device. In such an embodiment, the device may comprise another element for advancing and withdrawing the tube assembly 71 through the device, for example including, but not limited to, a slot and tab mechanism that may be similar to that depicted in the embodiment of FIG.

1. In some embodiments, the top and bottom shells of the housing of the scope lock assembly are molded as a single piece with the top and bottom shells, respectively, of the main device housing and the lumen of the scope lock housing is separated from the lumen of the main device housing by a partition having a hole for the scope to pass through. In other embodiments, there is no partition between the lumens.

FIGS. 44A-E show an embodiment of a scope lock button 150 of the device, more particularly of the device shown in FIGS. 27 and 28A-D. In this exemplary, but non-limiting, embodiment, the scope lock button 150 protrudes through the opening 138 in the upper shell 132 of the housing of the scope lock assembly 130. Pressing down on the scope lock button 150 engages a plate return spring 152 (FIGS. 29 and 45) that, in turn, engages a pair of locking plates 154 (FIGS. 29 and 46). This engagement presses the tops of the locking plates 154 towards one another, allowing a viewing device, such as an endoscope or arthroscope, to freely pass through the holes 155 in the locking plates 154. Releasing the scope lock button 150 allows it to return to its default, raised, position, locking the viewing device in place.

FIGS. 45A-E show an exemplary, non-limiting, embodiment of a plate return spring 152 element of an embodiment of a scope lock assembly 130 of the device, such as depicted in FIGS. 27 and 28A-D.

FIGS. 46A-D show an exemplary, non-limiting, embodiment of a locking plate 154 element of an embodiment of a scope lock assembly 130 of the device, such as depicted in FIGS. 27 and 28A-D. In some embodiments, as shown in FIGS. 46A and B, the locking plate 154 comprises a hole that a viewing device, such as an endoscope or arthroscope, can pass through.

Kit

Another aspect of the present application relates to an instrument kit for implementing an endoscopic surgical procedure. The kit comprises the endoscopic surgical blade assembly of the present application. In some embodiments, the instrument kit contains an endoscopic surgical device comprising a slotted clear cannula, a blade and a housing, wherein the cannula is attached to the housing, and further wherein the blade is enclosed in the housing and is slidable into the cannula.

In some embodiments, the endoscopic surgical device comprises a slotted clear cannula, a scraper, a blade and a housing, wherein the cannula is attached to the housing. In a pre-deployment configuration, the scraper and the blade are enclosed in the housing, the blade and scraper are individually selectable for deployment orientation, and the blade or scraper is slidable into the cannula in a deployment orientation.

In some embodiments, the instrument kit comprises components and implements useful for endoscopic procedures.

In one embodiment, the instrument kit further includes an endoscope sized for insertion into the slotted clear cannula for direct visualization of an operative site.

In another embodiment, the instrument kit further includes a scalpel.

In another embodiment, the instrument kit further includes an elevator.

In another embodiment, the instrument kit further includes a depth gauge mountable to a leading end of the endoscope.

In another embodiment, the instrument kit further includes a stop device mountable on or in the cannula to prevent excessive penetration at a surgical site by the cutting instrument.

In another embodiment, the instrument kit further includes a curved dissector.

Method for Endoscopic Surgery

Another aspect of the present application relates to a method for uniportal endoscopic surgery. Uniportal endoscopic surgery allows the practitioner to visualize a target tissue and its surrounding tissues as well as perform a surgical procedure through a single entry portal. In some instances, the entry portal may be a natural opening, while in other instances the entry portal is an incision. In the case of an incision, generally only a single small incision must be made. In particular embodiments, the incision is less than or equal to about 2 cm in length. In more particular embodiments, the incision is less than or equal to about 1.5 cm in length. In still more particular embodiments, the incision is less than or equal to about 1 cm in length. The single small incision allows the patient to recover more quickly and begin therapy and/or resume normal activity as tolerated sooner.

The uniportal endoscopic surgical procedure described herein can be used to implement a number of different surgical procedures including, but not limited to, carpal tunnel release, Guyon's canal (or canal) release, cubital tunnel release, plantar fascia release, lateral release for patella realignment, release of radial tunnel, release of pronator teres, release of trigger finger, release of lacertus fibrosus, release of the extensor tendons for lateral epicondylitis, release of medial epicondylitis, release of the posterior and other compartments of the leg, forearm fascia release for fascial compartment syndrome, release of fascial compartments in the upper or lower extremities, relieving the compression of a nerve by a ligament pulley or tunnel, releasing the travel of a ligament through a ligament pulley or tunnel, surgical procedures on the spine, such as endoscopic discectomy for the treatment of degenerative disc disease, herniated discs, bulging discs, pinched nerves or sciatica, endoscopic procedures on cranial and facial tissues, fasciotomy release and blood vessel harvesting.

One embodiment of the present application relates to a method for a performing a uniportal endoscopic surgical procedure a target tissue in a subject. Generally, the endoscopic surgical procedure requires the establishment of an entry portal. In some embodiments of the present application, the entry portal is established to the proximate side of the target tissue. In other embodiments of the present application, the entry portal is established to the distal side of the target tissue.

In some embodiments, the establishing an entry portal comprises making an incision.

In some embodiments, following the establishment of an entry portal, a blunt instrument, such as an elevator, is inserted through the portal to establish an opening in the underlying tissue between the portal and the target tissue. In other embodiments, following the establishment of an entry portal, an opening in the underlying tissue between the portal and the target tissue is established by inserting a clear slotted cannula having a sharpened front edge for separating tissues. In a further embodiment, a viewing device, such as an endoscope, is inserted into the clear slotted cannula in order to visualize the procedure of establishing an opening in the underlying tissue between the portal and the target tissue.

In one embodiment, an endoscopic surgical device comprising a slotted clear cannula, a blade and a housing, wherein the cannula is attached to the housing, and further wherein the blade is enclosed in the housing and is slidable into the cannula, is inserted into the entry portal and extended through to the target tissue.

In some embodiments, the endoscopic surgical device comprises a slotted clear cannula, a scraper, a blade and a housing, wherein, the cannula is attached to the housing, in a pre-deployment configuration the scraper and the blade are enclosed in the housing, the blade and scraper are individually selectable for deployment orientation, and in deployment orientation the blade or scraper are slidable into the cannula. In some further embodiments, the device comprises a tube assembly that allows a viewing device to be inserted through a central lumen, wherein the tube assembly engages separately with the blade or the scraper and advancing the tube assembly into the slotted clear cannula advances the selected blade or scraper.

In some embodiments, the endoscopic surgical device further comprises a mechanism for locking the viewing device in a fixed position relative to the tube assembly. In some further embodiments, the scope lock assembly engages with the tube assembly and is used as a handle for advancing or withdrawing the tube assembly into or from the slotted clear cannula.

An endoscope is inserted through the housing and into the cannula to view the target tissue and the surrounding tissues, assuring that the slot of the cannula is in proper orientation to the target tissue.

In one particular embodiment, the operative procedure is trigger finger release.

In another particular embodiment, the target tissue is the A1 pulley.

The present invention is further illustrated by the following examples which should not be construed as limiting. The contents of all references, patents and published patent applications cited throughout this application, as well as the Figures, are incorporated herein by reference.

Example 1: Uniportal Endoscopic Carpal Tunnel Release

In a patient presenting with carpal tunnel syndrome, an incision is made just proximal or distal to the carpal transverse ligament.

An endoscopic viewing device is inserted into an endoscopic surgical device having a slotted clear cannula that comprises a sharpened front edge for separating tissues. The viewing device is advanced into a tube assembly that can be engaged in the device with a blade or scraper and locked in place in relation to the tube assembly. The revolver of the device is set to allow the advancement of the tube assembly and endoscope without the deployment of the blade or scraper and the tube assembly is advanced into the cannula and locked into place.

The slotted clear cannula having a sharpened front edge is introduced into the incision and used to create a plane under the carpal transverse ligament, but superficial to the median nerve, with the slot of the cannula facing the carpal transverse ligament. The procedure is observed with the viewing device.

Following the creation of the plane, the tube assembly, still with the viewing device locked in place in relation to the tube assembly, is withdrawn back into the housing of the device. In the event that the ligament sheath obscures visualization of the ligament, the revolver of the device is turned to select deployment orientation of the scraper. The tube assembly is advanced into the cannula and the scraper protrudes through the slot of the cannula. The ligament sheath is removed with the scraper and the tube assembly is retracted, bringing the scraper back into the housing of the device. The revolver of the device is rotated to restore the scraper back to its pre-deployment configuration in the device.

The ligament is again visualized with the endoscope, the tube assembly is retracted and the revolver of the device is turned to select deployment orientation of the blade. The tube assembly is advanced with the endoscope into the cannula and the blade protrudes through the slot of the cannula. The blade is advanced into contact with the carpal transverse ligament. The blade is further pushed forward, dividing the carpal transverse ligament. The tube assembly is retracted, bringing the blade back into the housing of the device. The revolver of the device is rotated to restore the blade back to its pre-deployment configuration in the device.

The cut edges of the carpal transverse ligament and the underlying median nerve and tendons attached to the digits are visualized through the endoscope.

While visualizing the nerve and tendons, release is confirmed by passive manipulation of the digits through their range of motion.

The cannula is removed from the incision.

The wound is closed and a soft bandage is applied. In some cases, a splint is also applied to immobilize the wrist up to a week.

Example 2: Uniportal Endoscopic Trigger Release

In a patient presenting with trigger finger of the middle or ring finger, an incision is made just proximal to the A1 pulley on the distal palmar crease proximate to the affected digit or distal to the A1 pulley at or near the base of the affected digit.

An endoscopic viewing device is inserted into a slotted clear cannula having a sharpened front edge. The cannula is introduced into the incision and the sharpened front edge is used to create a plane superficial to the flexor tendon sheath, with the slot of the cannula facing the flexor tendon sheath. The procedure is observed with the viewing device.

In the event that the tenosynovium obscures visualization of the tendon, a scraper is advanced into the cannula and protrudes through the slot of the cannula. The tenosynovium is removed with the scraper and the scraper is retracted.

The flexor tendon sheath and the surrounding tissues are again visualized with the endoscope. A blade is advanced into the cannula and protrudes through the slot of the cannula. The blade is advanced into contact with the flexor tendon sheath. The blade is further pushed forward, dividing the flexor tendon sheath. The blade is retracted.

The cut edges of the flexor tendon sheath and the underlying flexor tendon are visualized through the endoscope. While visualizing the tendon, release of the tendon is confirmed by passive manipulation of the digit through its range of motion.

Example 3: Uniportal Endoscopic Cubital Tunnel Release

A patient presenting with a persistent tingling or "pins and needles" sensation in the hand, particularly in the ring and little fingers. The patient is diagnosed with cubital tunnel syndrome, having ulnar nerve entrapment through the cubital tunnel by the tendinous arch joining the humeral and ulnar heads of the flexor carpi ulnaris and/or the fascia tissue forming the tunnel. The patient is referred for surgical release of the tunnel. An incision is made directly over the ulnar nerve between the medial epicondyle and the olecranon.

An endoscopic viewing device is inserted into an endoscopic surgical device having a slotted clear cannula that comprises a sharpened front edge for separating tissues. The viewing device is advanced into a tube assembly that can be engaged in the device with a blade or scraper and locked in place in relation to the tube assembly. The revolver of the device is set to allow the advancement of the tube assembly and endoscope without the deployment of the blade or scraper and the tube assembly is advanced into the cannula and locked into place.

The slotted clear cannula having a sharpened front edge is introduced into the incision in the distal direction (i.e., towards the hand) and used to create a plane under the tendinous arch and fascia, but superficial to the ulnar nerve, with the slot of the cannula facing the tendinous arch and fascia. The procedure is observed with the viewing device.

The tube assembly is retracted from the cannula, back into the device, and the revolver of the device is turned to select deployment orientation of the blade. The tube assembly is advanced with the endoscope into the cannula and the blade protrudes through the slot of the cannula. The blade is advanced into contact with the tendinous arch and fascia of the tunnel to the distal side of the incision. The blade is further pushed forward, dividing the arch and fascia. The tube assembly is retracted, bringing the blade back into the housing of the device. The revolver of the device is rotated to restore the blade back to its pre-deployment configuration in the device.

The cut edges of the arch and fascia and the underlying ulnar nerve may be re-visualized through the endoscope.

The cannula is removed from the incision. In some instances, the fascia proximal to the incision may also need to be released. The cannula is re-inserted into the incision, this time in the proximal direction (i.e., towards the shoulder) and the viewing and division procedures are repeated, if necessary.

Before the skin is closed, the elbow is taken through its range of motion and the ulnar nerve is visualized through the incision to confirm that there is no subluxation of the ulnar nerve. The wound is closed and a soft bandage is applied. Early range of motion are started as soon as the patient can tolerate them and the patient is encouraged to resume activities as soon as they are comfortable.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. An endoscopic surgical device, comprising: a blade; a housing having a proximate end and a distal end; a cylindrical body comprising a selector switch; a slotted cannula attached to said distal end of said housing, said slotted cannula comprises a cannula body having a proximate end and a distal end; and an assembly extending proximally from the blade; wherein the slotted cannula further comprises a horizontal blade guidance track, wherein the assembly slidably engages with the horizontal blade guidance track; wherein the assembly comprises a notch, wherein the blade resides at the notch of the assembly in a pre-deployment position, and wherein the selector switch allows engagement selection of said blade for deployment.

2. The endoscopic surgical device of claim 1, wherein a distal end of the slotted cannula is a closed end that is shaped to serve as an elevator.

3. The endoscopic surgical device of claim 2, wherein the distal end of the slotted cannula forms an angle with the cannula body, wherein said angle is in a range of 165-145 degrees.

4. An endoscopic surgical kit, comprising the endoscopic surgical device of claim 1 and a scalpel.

5. The endoscopic surgical kit of claim 4, further comprising an endoscope.

6. A method for performing a uniportal endoscopic surgical procedure on a target tissue using the endoscopic surgical device of claim 1, comprising: establishing an entry portal in a subject; inserting the slotted cannula of the endoscopic surgical device into the entry portal; advancing the slotted cannula through the entry portal to the target tissue; visualizing the target tissue with an endoscope; and making a desired cut on the target tissue with the blade.

7. The method of claim 6, wherein establishing an entry portal comprises making an incision.

8. The method of claim 6, wherein the uniportal endoscopic surgical procedure is selected from a group consisting of trigger finger release, Guyon's canal release, carpal tunnel release, cubital tunnel release, fascia release, lateral release for patella realignment, release of extensor tendons, release of a posterior or other compartments of a leg, fascia release and blood vessel harvesting.

9. The method of claim 6, wherein the uniportal endoscopic surgical procedure is fascia release.

10. The method of claim 9, wherein the fascia release is selected from a group consisting of forearm fasciotomy, plantar fasciotomy, fasciotomy for compartment syndrome, leg fasciotomy and hand fasciotomy.

11. The method of claim 6, wherein the target tissue is selected from a group consisting of A1 pulley, carpal transverse ligament, cubital tunnel, Guyon's canal, fascia and blood vessel.

12. The method of claim 6, wherein the target tissue is a vein or artery.

* * * * *